US007914780B1

(12) United States Patent
Arap et al.

(10) Patent No.: US 7,914,780 B1
(45) Date of Patent: Mar. 29, 2011

(54) AMINOPEPTIDASE A (APA) TARGETING PEPTIDES FOR THE TREATMENT OF CANCER

(75) Inventors: Wadih Arap, Houston, TX (US); Renata Pasqualini, Houston, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 93 days.

(21) Appl. No.: 12/186,208

(22) Filed: Aug. 5, 2008

Related U.S. Application Data

(60) Division of application No. 10/784,537, filed on Feb. 23, 2004, now Pat. No. 7,420,030, which is a continuation-in-part of application No. PCT/US02/27836, filed on Aug. 30, 2002, which is a continuation-in-part of application No. PCT/US01/27692, filed on Sep. 7, 2001.

(60) Provisional application No. 60/231,266, filed on Sep. 8, 2000, provisional application No. 60/367,381, filed on Jan. 17, 2001.

(51) Int. Cl.
*A61K 48/00* (2006.01)
*C07K 5/00* (2006.01)

(52) U.S. Cl. ..................... 424/93.1; 530/300

(58) Field of Classification Search .................. None
See application file for complete search history.

(56) References Cited

U.S. PATENT DOCUMENTS

| | | | |
|---|---|---|---|
| 4,472,509 A | 9/1984 | Gansow et al. | 436/548 |
| 4,912,040 A | 3/1990 | Kaufman et al. | 435/69.6 |
| 4,931,053 A | 6/1990 | L'Esperance, Jr. | 606/2 |
| 5,021,236 A | 6/1991 | Gries et al. | 424/9 |
| 5,081,034 A | 1/1992 | Bevilasqua et al. | 435/252.33 |
| 5,098,833 A | 3/1992 | Lasky et al. | 435/69.1 |
| 5,188,964 A | 2/1993 | McGuire et al. | 436/64 |
| 5,206,347 A | 4/1993 | Ruoslahti et al. | 530/413 |
| 5,216,131 A | 6/1993 | Lasky et al. | 435/69.1 |
| 5,223,409 A | 6/1993 | Ladner et al. | 435/69.7 |
| 5,225,538 A | 7/1993 | Capon et al. | 530/387.3 |
| 5,259,380 A | 11/1993 | Mendes et al. | 607/115 |
| 5,270,163 A | 12/1993 | Gold et al. | 435/6 |
| 5,288,846 A | 2/1994 | Quertermous et al. | 435/172.3 |
| 5,304,640 A | 4/1994 | Lasky et al. | 536/23.5 |
| 5,336,248 A | 8/1994 | Good et al. | 607/90 |
| 5,415,874 A | 5/1995 | Bender et al. | 424/520 |
| 5,428,130 A | 6/1995 | Capon et al. | 530/350 |
| 5,453,362 A | 9/1995 | Lamarco et al. | 435/69.1 |
| 5,463,026 A | 10/1995 | Nakamura et al. | 530/387.3 |
| 5,464,436 A | 11/1995 | Smith | 607/89 |
| 5,492,807 A | 2/1996 | Santi | 435/5 |
| 5,506,126 A | 4/1996 | Seed et al. | 435/172.3 |
| 5,536,814 A | 7/1996 | Ruoslahti et al. | 530/329 |
| 5,585,277 A | 12/1996 | Bowie et al. | 436/518 |
| 5,622,699 A | 4/1997 | Ruoslahti et al. | 424/93.6 |
| 5,624,962 A | 4/1997 | Takeuchi et al. | 514/772.2 |
| 5,670,312 A | 9/1997 | Santi | 435/5 |
| 5,688,692 A | 11/1997 | Jat et al. | 435/354 |
| 5,688,935 A | 11/1997 | Stephens et al. | 536/23.1 |
| 5,705,610 A | 1/1998 | Zuckermann et al. | 530/338 |
| 5,750,344 A | 5/1998 | Doyle | 435/6 |
| 5,840,841 A | 11/1998 | Zuckermann et al. | 530/338 |
| 5,866,759 A | 2/1999 | Jat et al. | 800/3 |
| 5,902,598 A | 5/1999 | Chen et al. | 424/423 |
| 5,955,572 A | 9/1999 | Ruoslahti et al. | 530/317 |
| 6,057,098 A | 5/2000 | Buechler et al. | 435/6 |
| 6,068,829 A | 5/2000 | Ruoslahti et al. | 242/9.1 |
| 6,174,861 B1 | 1/2001 | O'Reilly et al. | 514/12 |
| 6,184,973 B1 | 2/2001 | Baer et al. | 356/36 |
| 6,215,550 B1 | 4/2001 | Baer et al. | 356/36 |
| 6,232,440 B1 | 5/2001 | Hillman et al. | 530/350 |
| 6,271,196 B1 | 8/2001 | O'Brien | 514/2 |
| 6,300,064 B1 | 10/2001 | Knappik et al. | 435/6 |
| 6,350,855 B1 | 2/2002 | Tobin | 530/350 |
| 6,399,384 B1 | 6/2002 | Jat | 435/456 |
| 6,458,381 B1 | 10/2002 | Sourovoi et al. | 424/450 |
| 6,528,281 B1 | 3/2003 | Tobin | 435/69.1 |
| 6,576,239 B1 | 6/2003 | Ruoslahti et al. | 424/185.1 |
| 6,881,825 B1 | 4/2005 | Robbins et al. | 530/327 |
| 2001/0046498 A1 | 11/2001 | Rouslahti et al. | 424/178.1 |
| 2003/0113320 A1 | 6/2003 | Ruoslahti et al. | 424/143.1 |
| 2005/0191294 A1 | 9/2005 | Arap et al. | 424/143.1 |

FOREIGN PATENT DOCUMENTS

| | | |
|---|---|---|
| DE | 19605175 | 8/1997 |
| EP | 0639584 | 4/1998 |
| JP | 4026631 | 1/1992 |
| WO | WO 92/00091 | 7/1991 |
| WO | WO 92/03461 | 3/1992 |
| WO | WO 92/06191 | 4/1992 |
| WO | WO 94/28424 | 12/1994 |
| WO | WO 95/14714 | 6/1995 |
| WO | WO 96/34874 | 11/1996 |
| WO | WO 96/34875 | 11/1996 |
| WO | WO 97/10507 | 3/1997 |
| WO | WO 97/19954 | 5/1997 |

(Continued)

OTHER PUBLICATIONS

Wu et al. J. Virology 2006, vol. 80, No. 22, pp. 11393-11397.*
Miki et al. J. Biolog. Chemist. 1999, vol. 274, No. 41, pp. 29057-29062.*
Deshayes et al. Biochemistry 2004, vol. 43, pp. 7698-7706.*
Aiello et al., "Suppression of retinal neovascularization in vivo by inhibition of vascular endothelial growth factor (VEGF) using soluble VEGF-receptor chimeric proteins," *Proc. Natl. Acad. Sci., USA*, 92(23):10457-10461, 1995.
Aiello et al., "Vascular endothelial growth factor in ocular fluid of patients with diabetic retinopathy and other retinal disorders," *N. Eng. J. Med.*, 331(22):1480-1487, 1994.

(Continued)

*Primary Examiner* — Bao Li
(74) *Attorney, Agent, or Firm* — Fulbright & Jaworski L.L.P.

(57) ABSTRACT

The present invention concerns compositions and methods for the treatment of cancer. More specifically, the present invention relates to identification of aminopeptidase A (APA) as a functional target in neo-vasculature, e.g., tumor vasculature; the present invention also relates to targeting peptides and antibodies specific for APA which may be used for cancer therapies.

38 Claims, 7 Drawing Sheets

FOREIGN PATENT DOCUMENTS

| | | |
|---|---|---|
| WO | WO 97/39021 | 10/1997 |
| WO | WO 98/10795 | 3/1998 |
| WO | WO 98/39469 | 9/1998 |
| WO | WO 99/04813 | 2/1999 |
| WO | WO 97/30024 | 9/1999 |
| WO | WO 99/46284 | 9/1999 |
| WO | WO 99/57311 | 11/1999 |
| WO | WO 00/14215 | 3/2000 |
| WO | WO 01/13114 | 8/2000 |
| WO | WO 01/42276 | 6/2001 |
| WO | WO 01/53342 | 7/2001 |
| WO | WO 02/02055 | 1/2002 |
| WO | WO 02/20722 | 3/2002 |
| WO | WO 02/20723 | 3/2002 |
| WO | WO 02/20769 | 3/2002 |
| WO | WO 02/20822 | 3/2002 |
| WO | WO 03/022991 | 3/2003 |

OTHER PUBLICATIONS

Alliot et al., "Brain parenchyma vessels and the angiotensin system," *Brain Res.*, 830:101-112, 1999.

Alliot et al., "Pericytes and periendothelial cells of brain parenchyma vessels co-express aminopeptidase N, aminopeptidase A, and nestin," *J. Neurosci. Res.*, 58:367-378, 1999.

Alon et al., "Vascular endothelial growth factor acts as a survival factor for newly formed retinal vessels and has implications for retinopathy of prematurity," *Nat. Med.*, 1:1024-1028, 1995.

Alonso and Maroto, "Plants as 'chemical factories' for the production of polyunsaturated fatty acids," *Biotechnology Advances*, 18:481-497, 200.

Andrade et al., "Angiotensin-Il-induced angiogenesis in sponge implants in mice," *Int. J. Microcirc. Clin. Exp.*, 16(6):302-307, 1996.

Arap et al., Steps toward mapping the human vasculature by phage display, *Nature Med.*, 8(2):121-127, 2002.

Arap et al., "Cancer treatment by targeted drug delivery to tumor vasculature in a mouse model," *Science*, 279:377-380, 1998.

Arap et al., "Cell surface expression of the stress response chaperone GRP78 enables tumor targeting by circulating ligands," *Cancer Cell*, 6:275-284, 2004.

Arap et al., "Chemotherapy targeted to tumor vasculature ," *Curr. Opin. Onclol.*, 10(6):560-565, 1998.

Arap et al., "Targeting the prostate for destruction through a vascular address," *Proc. Natl. Acad. Sci., USA*, 99:1527-1531, 2002.

Arden, "The absence of diabetic retinopathy in patients with retinitis pigmentosa: implications for pathophysiology and possible treatment.," *Br. J. Ophthalmol.*, 85:366-370, 2001.

Asako et al., "Organic solvent tolerance and antibiotic resistance increased by overexpression of marA in *Escherichia coli*," *Applied Environmental Microbiology*, 63(4):1428-1433, 1997.

Assmann et al., "A nephritogenic rat monoclonal antibody to mouse aminopeptidase A. Induction of massive albuminuria after a single intravenous injection," *J. Exp. Med.*, 175:623-635, 1992.

Atkins et al., "Coordinated cytokine expression by stromal and hematopoietic cells during human osteoclast formation," *Bone*, 26(6):653-661, 2000.

Baillie et al., "Tumor vasculature-A potential therapeutic target," *British J. Cancer*, 72:257-267, 1995.

Baringa, "Peptide-guided cancer drugs show promise in mice," *Science*, 279:323-324, 1998.

Baumann et al., "Complex of the soluble IL-11 receptor and IL-11 acts as IL-6-type cytokine in hepatic and nonhepatic cells," *J. Immunol.*, 157(1):284-290, 1996.

Beckman et al., "Experimental manipulation of the rodent visceral yolk sac," *Teratology*, 41(4):395-404, 1990.

Behm et al., "Human homologue of the rat chondroitin sulfate proteoglycan, NG2, detected by monoclonal antibody 7.1, identifies childhood acute lymphoblastic leukemias with t(4;11)(q21;q23) or t(11;19)(q23;13) and MLL gene rearrangements," *Blood*, 87:1134-1139, 1996.

Bergelson et al., "Isolation of a common receptor for Coxsackie B viruses and adenoviruses 2 and 5," *Science*, 275:1320-1322, 1997.

Bergers et al., "Benefits of targeting both pericytes and endothelial cells in the tumor vasculature with kinase inhibitors," *J. Clin. Invest.*, 111(9):1287-1295, 2003.

Bicknell, "Vascular targeting and the inhibition of angiogenesis," *Annals of Oncology*, 5(Suppl 4):S45-S50, 1994.

Bigner et al., "Phase I studies of treatment of malignant gliomas and neoplastic meningitis with 131I-radiolabeled monoclonal antibodies anti-tenascin 81C6 and anti-chondrotin sulfate proteoglycan Mel-14F(ab1)2-a preliminary report," *J. Neuro-Oncol.*, 24:109-122, 1995.

Bogenreider et al., "Expression and localization of aminopeptidase A, aminopeptidase N, and dipeptidyl peptidase IV in benign and malignant human prostate tissue," *Prostate*, 33:225-232, 1997.

Brooks et al., "Anti integrin alpha v beta 3 blocks human breast cancer growth and angiogenesis in human skin," *J. Clin. Invest.*, 96:1815-1822, 1995.

Brooks et al., "Integrin alpha v beta 3 antagonists promote tumor regression by inducing apoptosis of angiogenic blood vessels," *Cell*, 79(7):1157-1164, 1994.

Brooks et al., "Requirement of vascular integrin $\alpha v \beta 3$ for angiogenesis," *Science*, 264:569-571, 1994.

Bumol et al., "Monoclonal antibody and antibody-toxin conjugate to a cell surface proteoglycan of melanoma cells suppress in vivo tumor growth," *Proc. Natl. Acad. Sci., USA*, 80:529-533, 1983.

Burg et al., "A central segment of the NG2 proteoglycan is critical for the ability of glioma cells to bind and migrate toward type VI collagen," *Exp. Cell Res.*, 235:254-264, 1997.

Burg et al., "Binding of the NG2 proteoglycan to type VI collagen and other extracellular matrix molecules," *J. Biol. Chem.*, 271(42):26110-26116, 1996.

Burg et al., "Expression of the NG2 proteoglycan enhances the growth and metastatic properties of melanoma cells," *J. Cell. Physiol.*, 177:299-312, 1998.

Burg et al., "NG2 proteoglycan-binding peptides target tumor neovasculature," *Cancer Res.*, 59(12):2869-2874, 1999.

Burioni et al., "Recombinant human Fab to glycoprotein D neutralizes infectivity and prevents cell-to-cell transmission of herpes simplex viruses 1 and 2 in vitro," *Proc. Natl. Acad. Sci., USA*, 91:355-359, 1994.

Burrows and Thorpe, "Vascular targeting-A new approach to the therapy of solid tumors," *Pharmac. Ther.*, 64:155-174, 1994.

Burton et al., "A large array of human monoclonal antibodies to type 1 human immunodeficiency virus from combinatorial libraries of asymptomatic seropositive individuals," *Proc. Natl. Acad. Sci., USA*, 88:10134-10137, 1991.

Butner, "Retinitis pigmentosa and retinal neovascularization: a case report," *Ann. Ophthalmol.*, 16:861-865, 1984.

Cai et al., "Induction of glucose regulated proteins during growth of a murine tumor," *J. Cell Physiol.*, 154(2):229-237, 1993.

Campbell et al., "Prohibitin 3' untranslated region polymorphism and breast cancer risk," *Cancer Epidemiol. Biomarkers Prev.*, 12(11 pt1):1273-1274, 2003.

Campfield and Smith, "Overview: neurobiology of OB protein (leptin)," Proceedings of the Nutrition Society, 57:429-440, 1998.

Campfield et al., "Strategies and potential molecular targets for obesity treatment," *Science*, 280:1383-1387, 1998.

Cao et al., "Expression of angiostatin cDNA in a murine fibrosarcoma suppresses primary tumor growth and produces long-term dormancy of metastases," *J. Clin. Invest.*, 101:1055-1063, 1998.

Cattani et al., "Cloning and characterization of human recombinant antibody Fab fragments specific for types 1 and 2 herpes simplex virus," *Microbiologica*, 18:135-142, 1995.

Chaveroche et al., "A rapid method for efficient gene replacement in the filamentous fungus *Aspergillus nidulans* ," *Nucleic Acids Research*, 28(22):E97, 2000.

Chen et al., "Thapsigargin-induced grp78 expression is mediated by the increase of cytosolic free calcium in 9L rat brain tumor cells," *J. Cell. Biochem.*, 78:404-416, 2000.

Chinni et al., "Humoral immune responses to cathepsin D and glucose-regulated protein 78 in ovarian cancer patients," *Clin. Cancer Res.*, 3:1557-1564, 1997.

Choongkittaworn et al., "Expression of prohibitin in rat seminiferous epithelium," *Biol. Reprod.*, 49(2):300-310, 1993.

Costantini et al., "Mitochondrion as a novel target of anticancer chemotherapy," *J. Natl. Cancer Inst.*, 92(13):1042-1053, 2000.
Curnis et al., "Enhancement of tumor necrosis factor alpha antitumor immunotherapeutic properties by targeted delivery to aminopeptidase N (CD13)," *Nat Biotechnol.*,(11):1185-90, 2000.
D'Amato et al., "Thalidomide is an inhibitor of angiogenesis," *Proc. Natl. Acad. Sci., USA*, 91:4082-4085, 1994.
Daniels and Lane, "Phage Peptide Libraries," *Methods*, 9:494-507, 1996.
Davis et al., "Use of a high affinity DNA ligand in flow cytometry," *Nucleic Acids Research*, 24:702-706, 1996.
De Rosa et al., "Poly(lactide-co-glycolide) microspheres for the controlled release of oligonucleotide/polyethylenimine complexes ," *J Pharm Sci*, 91(3):790-799, 2002.
Delpino et al., "Cell surface localization of the 78 kD glucose regulated protein (GRP 78) induced by thapsigargin," *Mol. Membr. Biol.*, 15(1):21-26, 1998.
Deo et al., "Bispecific molecules directed to the Fc receptor for IgA (FcαRI, CD89) and tumor antigens efficiently promote cell-mediated cytotoxicity of tumor targets in whole blood," J. Immunology, 160:1677-1686, 1998.
Dmitriev et al., "An adenovirus vector with genetically modified fibers demonstrates expanded tropism via utilization of a coxsackievirus and adenovirus receptor-independent cell entry mechanism," *J. Virol.*, 72(12):9706-9713, 1998.
Douglas et al., "Targeted gene delivery by tropism-modified adenoviral vectors," *Nature Biotech.*, 14:1574-1578, 1996.
Drolet et al., "An enzyme-linked oligonucleotide assay," *Nat. Biotech.*, 14:1021-1025, 1996.
Duh et al., "Vascular endothelial growth factor and diabetes," *Diabetes*, 48:1899-1906, 1997.
Dvorak et al., "Structure of solid tumors and their vasculature: implications for therapy with monoclonal antibodies," *Cancer Cells*, 3:77-85, 1991.
Egeblad and Werb, "New functions for the matrix metalloproteinases in cancer progression," *Nat. Rev. Cancer*, 2:161-174, 2002.
Ellerby et al., "Anti-cancer activity of targeted pro-apoptotic peptides," *Nature Med.*, 5(9):1032-8, 1999.
European Office Action, issued in European Application No. 02 757 531.5, mailed Mar. 27, 2008.
Fairbrother et al., "Novel Peptides Selected to Bind Vascular Endothelial Growth Factor Target Receptor-Binding Site," *Biochemistry*, 37:17754-17764, 1998.
Finnell, "Teratology: general considerations and principles," *J. Allergy Clin. Immunol.*, 103(2 Pt 2):S337-42, 1999.
Folkman, "Addressing tumor blood vessels," *Nature Biotechnology*, 15:510, 1997.
Folkman, "Angiogenesis in cancer, vascular, rheumatoid and other disease," *Nature Biotechnol.*, 1:27-31, 1995.
Fujimura et al., "Aminopeptidase A expression in cervical neoplasia and its relationship to neoplastic transformation and progression," *Oncology*, 58:342-352, 2000.
Furuya et al., "The role of calcium, pH, and cell proliferation in the programmed (apoptotic) death of androgen-independent prostatic cancer cells induced by thapsigargin," *Cancer Res.*, 54(23):6167-6175, 1994.
Fusaro et al., "Prohibitin induces the transcriptional acivity of p53 and is exported from the nucleus upon apoptotic signaling," *J. Biol. Chem.*, 278(48):47853-47861, 2003.
Geng et al., "Expression of the kidney-associated differentiation glycoprotein gp160 and resistance to the antitumor effects of interferon alpha in renal cell carcinomas," *Anticancer Res.*, 18:1-7, 1998.
Giordano et al., "Biopanning and rapid analysis of selective interactive ligands," *Nat. Med.*, 7(11):1249-1253, 2001.
Girod et al., "Genetic capsid modifications allow efficient re-targeting of adeno-associated virus type 2," *Nature Med.*, 5:1052-1056, 1999.
Goetz et al., "Lu-ECAM-1-mediated adhesion of melanoma cells to endothelium under conditions of flow," *Int. J. Cancer*, 65:192-199, 1996.
Gold et al., "Diversity of oligonucleotide functions," *Annu. Rev. Biochem.*, 64:763-797, 1995.

Goldman et al., "Targeted gene delivery to Kaposi's sarcoma cells via the fibroblast growth factor receptor," *Cancer Res.*, 57(8):1447-51, 1997.
Gong et al., "Prostrate-specific membrane antigen (PMSA)-specific monoclonal antibodies in the treatment of prostrate and other cancers," *Cancer and Metastasis Reviews*, 18:483-490,1999.
Goodson et al., "High-affinity urokinase receptor antagonists identified with bacteriophage peptide display," *Proc. Natl. Acad. Sci., USA*, 91:7129-7133, 1994.
Grako and Stallcup, "Participation of the NG2 proteoglycan in rat aortic smooth muscle cell responses to platelet-derived growth factor," *Exp. Cell Res.*, 221:231-240, 1995.
Grasso et al., "In vivo effects of leptin-related synthetic peptides on body weight and food intake in female ob/ob mice: localization of leptin activity to domains between amino acid residues 106-140," *Endocrinology*, 138(4):1413-1418, 1997.
Grifman et al., "Incorporation of tumor-targeting peptides into recombinant adeno-associated virus capsids," *Mol. Ther.*, 3(6):964-75, 2001.
Griscelli et al., "Angiostatin gene transfer: inhibition of tumor growth in vivo by blockage of endothelial cell proliferation associated with a mitosis arrest," *Proc. Natl. Acad. Sci., USA*, 95:6367-6372, 1998.
Hadigan et al., "Metformin in the treatment of HIV lipodystrophy syndrome: A randomized controlled trial," *J. Amer. Med. Assn.*, 284:472-477, 2000.
Hammes et al., "Subcutaneous injection of a cyclic peptide antagonist of vitronectin receptor-type integrins inhibits retinal neovascularization," *Nature Med.*, 2:529-533, 1996.
Hanahan, "Signaling vascular morphogenesis and maintenance," *Science*, 277:48-50, 1997.
Harper and Reisfeld, "Cell-associated proteoglycans in human malignant melanoma," *Biology of Proteoglycans*, Acad. Press, 345-366, 1987.
Harper and Reisfeld, "Inhibition of anchorage independent growth of human melanoma cells by a monoclonal antibody to a chondrotin sulfate proteoglycan," *J. Natl. Cancer Inst.*, 71:259-263, 1983.
Hart et al., "Cell binding and internalization by filamentous phage displaying a cyclic Arg-Gly-Asp-containing peptide," *J. Biol. Chem.*, 269:12468-12474, 1994.
Hashizume et al., "Openings between defective endothelial cells explain tumor vessel leakiness," *Am. J. Pathol.*, 156(4):1363-1380, 2000.
Hayakawa et al., "Clinical features of autosomal dominant retinitis pigmentosa with rhodopsin gene codon 17 mutation and retinal neovascularization in a Japanese patient," *Am. J. Ophthalmol.*, 115:168-173, 1993.
Hicke et al., "DNA aptamers block L-selectin function in vivo," *J. Clin. Invest.*, 98:2688-2692, 1996.
Hong et al., "Adenovirus type 5 fiber knob binds to MHC class I alpha2 domain at the surface of human epithelial and B lymphoblastoid cells," *EMBO J.*, 16:2294-2306, 1997.
Huang et al., "Tumor infarction in mice by antibody-directed targeting of tissue factor to tumor vasculature," *Science*, 275:547-550, 1997.
Hussain et al., "Nasal mucosal metabolism and absorption of pentapeptide enkephalin analogs having varying N-terminal amino acids," *J. Pharm. Sci.*, 84(1):62-64, 1995.
Iida et al., "Spreading and focal contact formation of human melanoma cells in response to the stimulation of both NG2 α4β1 integrin," *Cancer Res.*, 55:2177-2185, 1995.
Ikonen et al., "Prohibitin, an antiproliferative protein, is localized to mitochondria," *FEBS Letters*, 358(3):273-277, 1995.
Ino et al., "Expression of aminopeptidase A in human gestational choriocarcinoma cell lines and tissues," *Placenta*, 21:63-72, 2000.
Jackson, In: Goodman and Gilman's *The Pharmacological Basis of Therapeutics*, Hardman (eds.), McGraw-Hill Medical Publishing Division, 809-841, 2001.
Jain et al., "Metabolic complications associated with antiretroviral therapy," *Antiviral Res.*, 51:151-177, 2001.
Javadpour et al., "De novo antimicrobial peptides with low mammalian cell toxicity," *J. Med. Chem.*, 39:3107-3113, 1996.
Johnson et al., In: *Biotechnology and Pharmacy*, Pezzuto et al. eds., Chapman and Hall, NY, 1993.

Joliot et al., "alpha-2,8-Polysialic acid is the neuronal surface receptor of antenna pedia homeobox peptide," *New Biol.*, 3:1121-1131, 1991.

Joliot et al., "Antenna pedia homeobox peptide regulates neural morphogenesis," *Proc. Natl. Acad. Sci., USA*, 88:1864-1868, 1991.

Juillerat-Jeanneret et al., "Regulation of aminopeptidase A in human brain tumor vasculature: evidence for a role of transforming growth factor-beta," *Lab. Invest.*, 80(6):973-980, 2000.

Juillerat-Jeanneret et al., "Regulation of peptidase activity in a three-dimensional aggregate model of brain tumor vasculature," *Cell Tissue Res.*, 311:53-59, 2003.

Jupe et al., "The 3' untranslated region of prohibitin and cellular immortalization," *Exp. Cell Res.*, 224(1):128-135, 1996.

Kahler et al., "Chronic administration of OB protein decreases food intake by selectively reducing meal size in male rats," *Am J Physiol*, 275(1 Pt 2):R180-R185, 1998.

Kerbel, "Inhibition of tumor angiogenesis as a strategy to circumvent acquired resistance to anti-cancer therapeutic agents," *BioEssays*, 13(1):31-36, 1991.

Kiang et al., "17 beta-estradiol-induced increases in glucose-related protein 78kD and 94kD protect human breast cancer T47-D cells from thermal injury," *Chin. J. Physiol.*, 40(4):213-219, 1997.

Kifor and Dzau, "Endothelial renin-angiotensin pathway: evidence for intracellular synthesis and secretion of angiotensins," *Circ. Res.*, 60:422-428, 1987.

Kiovunen et al., "Identification of receptor ligands with phage display peptide libraries," *J. Nuclear Medicine*, 40(5):883-888, 1999.

Koivunen et al., "Integrin-binding peptides derived from phage display libraries," *Methods Mol. Biol.*, 129:3-17, 1999.

Koivunen et al., "Phage libraries displaying cyclic peptides with different ring sizes: ligand specificities of the RGD-directed integrins," *Biotechnology*, 13(3):265-270, 1995.

Koivunen et al., "Selection of peptides binding to the alpha5 beta1 integrin from phage display library," *J. Biol. Chem.*, 268:20205-20210, 1993.

Koivunen et al., "Tumor targeting with a selective gelatinase inhibitor," *Nat. Biotechnol.*, 17:768-774, 1999.

Kolonin et al., "Molecular addresses in blood vessels as targets for therapy," *Curr. Opin. Chem. Biol.*, 5:308-313, 2001.

Kolonin et al., "Reversal of obesity by targeted ablation of adipose tissue," *Nature Medicine*, 10: 625-632, 2004.

Kolonin et al., "Targeting physiological and pathological blood vessel formation with in vivo phage display," *Proc. Am. Assoc. Cancer Res.*, 42:822-823, 2001.

Kolonin et al., "Teratogenicity induced by targeting a placental immunoglobulin transporter," *Proc. Natl. Acad. Sci., USA*, 99(20):13055-13060, 2002.

Lahdenranta et al., "An anti-angiogenic state in mice and humans with retinal photoreceptor cell degeneration," *Proc. Natl. Acad. Sci., USA*, 98(18):10368-10373, 2001.

Lamers and Bacher, "Prohibitin and prohibitone, ubiquitous and abundant proteins that are reluctant to reveal their real identity," *Int. Arch. Allergy Immunol.*, 113(1-3):146-149, 1997.

Lappi, "Tumor targeting through fibroblast growth factor receptors," *Cancer Biology*, 6:279-288, 1995.

Larocca et al., "Gene transfer to mammalian cells using genetically targeted filamentous bacteriophage," *FEBS J.*, 13:727-734, 1999.

Le Noble et al., "The role of angiotensin II and prostaglandins in arcade formation in a developing microvascular network," *J. Vasc. Res.*, 33(6):480-488, 1996.

Le Roux et al., "Neurotrophic activity of the Antenna pedia homeodomain depends on its specific DNA-binding properties," *Proc. Natl. Acad. Sci., USA*, 90:9120-9124, 1993.

Leff, "NeXstar previews 'PASS' for downstream synthesis of therapeutic oligos," *Bioworld Today*, 8:2&4, 1997.

Leger et al., "The chondroitin sulfate proteoglycan NG2 is a tumor specific antigen on the chemically induced rat chondrosarcoma HSN," *Int. J. Cancer*, 58:700-705, 1994.

Li et al., "Widespread tissue distribution of aminopeptidase A, an evolutionarily conserved ectoenzyme recognized by the BP-1 antibody," *Tissue Antigens*, 42:488-496, 1993.

Lin et al., "T and B cell development in BP-1/6C3/aminopeptidase A-deficient mice," *J. Immunol.*, 160(10):4681-4687, 1998.

Look et al., "Human myeloid plasma membrane glycoprotein CD13 (gp150) is identical to aminopeptidase N," *J. Clin. Invest.*, 83:1299-1307, 1999.

Makinen et al., "Differential binding of vascular endothelial growth factor B splice and proteolytic isoforms to neuropilin-1 ," 274(30):21217-22, 1999.

Mandecki et al., "A mathematical model for biopanning (affinity selection) using peptide libraries on filamentous phage," *J. Theor. Biol.*, 176:523-530, 1995.

Manjeshwar et al., "Tumor suppression by the prohibitin gene 3'untranslated region RNA in human breast cancer," *Cancer Res.*, 63(17):5251-5256, 2003.

Maranghi et al., "Evaluation of the placenta: suggestions for a greater role in developmental toxicology," *Adv. Exp. Med. Biol.*, 444:129-136, 1998.

Marchio et al., "Aminopeptidase A-Binding Peptides Regulate Endothelial Cell Function and Inhibit Angiogenesis," *Tumori*, 86 (4) Supp. 1: 13, 2000.

Martin et al., "Retrovirus targeting by tropism restriction to melanoma cells," *J. Virol.*, 73:6923-6929, 1999.

Martiny-Baron and Marmé, VEGF-mediated tumor angiogenesis: a new target for cancer therapy, *Curr. Opin. Biotech.*, 6:675-680, 1995.

McCarty et al., "Quantitative and qualitative in vivo angiogenesis assay," *Int. J. Oncol.*, 21(1):5-10, 2002.

McClung et al., "Prohibitin: potential role in senescence, development, and tumor suppression," *Exp. Gerontol.*, 30(2):99-124, 1995.

McConnell et al., "Biopanning phage display libraries using magnetic beads vs. polystyrene plates," *BioTechniques*, 26(2):208-209, 1999.

Mentzel et al., "Induction of albuminuria in mice: Synergistic effect of two monoclonal antibodies directed to different domains of aminopeptidase A," *Kidney International*, 55:1335-1347, 1999.

Mentzel et al., "Induction of albuminuria in mice: synergistic effect of two monoclonal antibodies directed to different domains of aminopeptidase A," *Kidney Int.*, 55(4):1335-1347, 1999.

Miller et al., "Differential susceptibility of primary and established human glioma cells to adenovirus infection: targeting via the epidermal growth factor receptor achieves fiber receptor-independent gene transfer," *Cancer Res.*, 58:5738, 5748, 1998.

Miner et al., "Clonal drift of cell surface, melanogenic and experimental metastatic properties of in vivo-selected, brain meninges-colonizing murine B16 melanoma," *Cancer Research*, 42:4631-4638, 1982.

Mintz et al.,"Fingerprinting the circulating repertoire of antibodies from cancer patients," *Nature Biotechnology*, 21:57-63, 2003.

Misra et al., "The role of Grp 78 in alpha 2-macroglobulin-induced signal transduction. Evidence from RNA interference that the low density lipoprotein receptor-related protein is associated with, but not necessary for, GRP 78-mediated signal transduction," *J Biol Chem.*, 277(44):42082-7, 2002.

Monton et al., "Effects of angiotensin II on endothelial cell growth: role of AT-1 and AT-2 receptors," *J. Am. Soc. Nephrol.*, 9(6):969-974, 1998.

Morikawa et al., "Abnormalities in pericytes on blood vessels and endothelial sprouts in tumors," *Am. J. Pathol.*, 160(3):985-1000, 2002.

Muller et al., "Effect of concentration on the cytotoxic mechanism of doxorubicin—apoptosis and oxidative DNA damage," *Biochem. Biophys. Res. Comm.*, 23:254-257, 1997.

Murphy et al., "Tissue inhibitor of metalloproteinases-2 inhibits bFGF-induced human microvascular endothelial cell proliferation," *J. Cell Physiol.*, 157(2):351-358, 1993.

Mustonen and Alitalo, "Endothelial receptor tyrosine kinases involved in angiogenesis ," *J. Cell Biol.*, 129:895-898, 1995.

Nadal et al., "Angiotensin II stimulates migration of retinal microvascular pericytes: involvement of TGF-β and BDGF-BB," *Am. J. Physiol. Heart Circ. Physiol.*, 282:739-748, 2002.

Nagan et al., "Modulation of lysyl oxidase activity toward peptidyl lysine by vicinal dicarboxylic amino acid residues. Implications for collagen cross-linking," *J. Biol. Chem.*, 269(35):22366-22371, 1994.

Nagy et al., "Cytotoxic analogs of luteinizing hormone-releasing hormone containing doxorubicin or 2-pyrrolinodoxorubicin, a derivative 500-1000 times more potent," *Proc. Natl. Acad. Sci., USA*, 93:7269-7273, 1996.

Nagy et al., "Synthesis and biological evaluation of cytotoxic analogs of somatostatin containing doxorubicin or its intesely potent derivative, 2-pyrrolinodoxorubicin," *Proc. Natl. Acad. Sci., USA*, 95:1794-1799, 1998.

Nanus et al., "Molecular cloning of the human kidney differentiation antigen gp160: human aminopeptidase A," *Proc. Natl. Acad. Sci., USA*, 90:7069-7073, 1993.

Napier and Michaelson, "Genomic and Functional Characterization of Polyunsaturated Fatty Acid Biosynthesis in *Caenorhabditis elegans*," *Lipids*, 36:761-766, 2001.

Nelson, "Parenting of therapeutics for obesity and nutritional disease," Exp Opin Ther Patents, 9(9):1185-1196, 1999.

Nicklin et al., "Selective argeting of gene transfer to vascular endothelial cells by use of peptides isolated by phage display," *Circulation*, 102:231-237, 2000.

Nishiyama and Stallcup, "Expression of NG2 proteoglycan causes retention of type VI collagen on the cell surface," *Mol. Biol. Cell*, 4:1097-1108, 1993.

Nishiyama et al., "Interaction between NG2 proteoglycan and PDGF α receptor is required for optimal response to PDGF," *J. Neurosci. Res.*, 43:315-330, 1996.

Nishiyama et al., "The primary structure of NG2, a novel membrane-spanning proteoglycan," *J. Cell. Biol.*, 114:359-371, 1991.

Nomizu et al., "Cell binding sequences in mouse laminin alphal chain," *J. Biol. Chem.*, 273(46):32491-32499, 1998.

Nuell et al., "Prohibitin, an evolutionary conserved intracellular protein that blocks DNA synthesis in normal fibroblasts and HeLa cells," *Mol. Cell Biol.*, 11(3):1372-1381, 1991.

Office Action, issued in U.S. Appl. No. 10/784,537, mailed Jan. 12, 2006.

Office Action, issued in U.S. Appl. No. 10/784,537, mailed Mar. 30, 2007.

Office Action, issued in U.S. Appl. No. 10/784,537, mailed Sep. 14, 2007.

Office Action, issued in U.S. Appl. No. 10/784,537, mailed Sep. 22, 2006.

Oike et al., "Angiopoietin-related growth factors antagonizes obesity and insulin resistence," *Nature Medicine*, 11:400-408, 2005.

Okamoto et al., "Transgenic mice with increased expression of vascular endothelial growth factor in the retina," *Am. J. Pathol.*, 151(1):281-291, 1997.

Oloffson et al., "Phage viability in organic media: insights into phage stability," *J Mol Recognit*, 11(1-6):91-93, abstract, 1998.

Olofsson et al., "Current biology of VEGF-B and VEGF-C," *Curr. Op. Biotechnol.*, 10:528-535, 1999.

Owens et al., "Cloning the antibody response in humans with chronic inflammatory disease: immunopanning of subacute sclerosing panencephalitis (SSPE) brain sections with antibody phage libraries prepared from SSPE brain enriches for antibody recognizing measles virus antigens in situ," *J. Virol.*, 74(3):1533-1537, 2000.

Ozata et al., "Human Leptin Deficiency caused by a missense Mutation: Multiple Endocrine Defects, Decreased sympathetic tone, and immune system dysfunction indicate new targets for leptin action, greater centralthan peripheral resistance to the effects of leptin, and spontaneous correction of leptin-mediated defec," *Jounral of Clinical Endocrinology and Metabolism*, 84:3686-3695, 1999.

Pasqualini and Ruoslahti, "Organ targeting in vivo using phage display peptide libraries," *Nature*, 380:364-366, 1996.

Pasqualini et al., "A peptide isolated from phage display libraries is a structural and functional mimic of an RGD-binding site on integrins," *J. Cell Biol.*, 130:1189-1196, 1995.

Pasqualini et al., "Aminopeptidase N is a receptor for tumor-homing peptides and a target for inhibiting angiogenesis," *Cancer Res.*, 60(3):722-727, 2000.

Pasqualini et al., "αv integrins as receptors for tumor targeting by circulating ligands," *Nature Biotechnology*, 15:542-546, 1997.

Pasqualini et al., In: *Phage Display: A Laboratory Manual*, eds. Barbas et al., Cold Spring Harbor Laboratory Press, New York, NY, 22.1-24, 2000.

Pasqualini, "Vascular targeting with phage peptide libraries," *J. Nucl. Med.*, 43(2):159-162, 1999.

Pauli et al., "Organ-preference of metastasis," *Cancer and Metastasis Reviews*, 9:175-189, 1990.

Pereboeva et al., "Hepatitis C epitopes from phage-displayed cDNA libraries and improved diagnosis with a chimeric antigen," *J. Med. Virol.*, 60:144-151, 2000.

Pereboeva et al., "Identification of antigenic sites on three hepatitis C virus proteins using phage-displayed peptide libraries," *J. Med. Virol.*, 56:105-111, 1998.

Pierce et al., "Regulation of vascular endothelial growth factor by oxygen in a model of retinopathy of prematurity," *Arch. Ohpthlamol.*, 114:1219-1228, 1996.

Pierce et al., "Vascular endothelial growth factor/vascular permeability factor expression in a mouse model of retinal neovascularization.," *Proc. Natl. Acad. Sci., USA*, 92(3):905-909, 1995.

Pluschke et al., "Molecular cloning of a human melanoma-associated chondroitin sulfate proteoglycan," *Proc. Natl. Acad. Sci., USA*, 93:9710-9715, 1996.

Polgren et al., "Identification of muscle homing sequences by using phage display libraries of peptides," *Tumor Biology*, 18:77, 1997.

Prezzi et al., "Selection of antigenic and immunogenic mimics of hepatitis C virus using sera from patients," *J. Immunol.*, 156:4504-4513, 1996.

Pruett, "Retinitis pigmentosa: clinical observations and correlations," *Trans. Am. Ophthamol. Soc.*, 81:693-735, 1983.

Rajotte and Ruoslahti, "Membrane dipeptidase is the receptor for a lung-targeting peptide identified by in vivo phage display," *J. Biol. Chem.*, 274:11593-11598, 1999.

Rajotte et al., "Membrane dipeptidase is the receptor for a lung-targeting peptide identified by in vivo phage display," *J. Biol. Chem.*, 274(17):11593-11598, 1999.

Rajotte et al., "Molecular heterogeneity of the vascular endothelium revealed by in vivo phage display," *J. Clin. Invest.*, 102(2):430-437, 1998.

Rak et al., "Consequences of angiogenesis for tumor progression, metastasis and cancer therapy," *Anti-Cancer Drugs*, 6:3-18, 1995.

Raulin et al., "Human immunodeficiency virus and host cell lipid. Interesting pathways in research for a new HIV therapy," *Prog. Lipid Res.*, 41:27-65, 2002.

Real et al., "Surface antigens of melanomas and melanocytes defined by mouse monoclonal antibodies: specificity, analysis, and comparison of antigen expression in cultured cells and tissues," *Cancer Res.*, 45:4401-4411, 1985.

Riordan, "Patents," *The New York Times*, Monday, Sep. 15, 1997.

Roof and Makino, "Structure and function of retinal photoreceptors," *Principles and Practice of Ophthalmology*, W.B. Saunders Company, Philadelphia, 2000.

Roux et al., "Human cord blood monocytes undergo terminal osteoclast differentiation in vitro in the presence of culture medium conditioned by giant cell tumor of bone," *J. Cell Physiol.*, 168(3):489-498, 1996.

Rugh, *The Mouse: Its Reproduction and Development*, Oxford Science Publications, Oxford, 1990.

Sang, "Complex role of matrix metalloproteinase in angiogenesis," *Cell Res.*, 8(3):171-177, 1998.

Schindler, "Select, microdissect, adneject." *Nature Biotechnology*, 16:719-720,1998.

Schlingemann et al., "Aminopeptidase a is a constituent of activated pericytes in angiogenesis," *J. Pathol.*, 179(4):436-442, 1996.

Schlingemann et al., "Differential expression of markers for endothelial cells, pericytes, and basal lamina in the microvasculature of tumors and granulation tissues," *Amer. J. Path.*, 138:1335-1347, 1991.

Schlingemann et al., "Expression of the high molecular weight melanoma-associated antigen by pericytes during angiogenesis in tumors and in healing wounds," *Amer. J. Path.*, 136:1393-1405, 1990.

Schrappe et al., "Correlation of chondroitin sulfate proteoglycan expression on proliferating brain capillary endothelial cells with the malignant phenotype of astroglial cells," *Cancer Res.*, 51:4986-4993, 1991.

Scott and Smith, "Searching for peptide ligands with an epitope library," *Science*, 249:386-390, 1990.

Smith and Scott, "Libraries of peptides and proteins displayed in filamentous phage," *Meth. Enzymol.*, 21:228-257, 1993.

Smith et al., "Oxygen-induced retinopathy in the mouse," *Invest. Ohpthlamol.*, 35(1):101-111, 1994.

Smith, "Filamentous fusion phage: novel expression vectors that display cloned antigens on the virion surface," *Science*, 228:1315-1317, 1985.

Spitler et al., "Therapy of patients with malignant melanoma using a monoclonal anti-melanoma antibody-ricin immunotoxin," *Cancer Res.*, 47:1717-1723, 1987.

Spurdle et al., "The prohibitin 3'untranslated region polymorphism is not associated with risk of ovarian cancer," *Gynecol. Oncol.*, 90(1):145-149, 2003.

St. Croix et al., "Genes expressed in human tumor endothelium ," *Science*, 289(5482):1197-1202, 2000.

St. Hilaire et al., "The Substrate specificity of a recombinant cystein protease from *Leishmania mexicana*: application of a combinatorial peptide library approach," *Chembiochem: A European Journal of Chemical Biology*, 1:115-122, 2000.

Stone et al., "Development of retinal vasculature is mediated by hypoxia-induced vascular endothelial growth factor (VEGF) expression by neuroglia," *J. Neurosci.*, 15(7):4738-4747, 1995.

Tanaka et al., "Viral vector-targeted antiangiogenic gene therapy utilizing an angiostatin complementary DNA," *Cancer Res.*, 58(15):3362-9, 1998.

Tillet et al., "The membrane-spanning proteoglycan NG2 binds to collagen V and VI through central non-helical portion of the ectodomain," *J. Biol. Chem.*, 272:10769-10776, 1997.

Trepel et al., "Molecular adaptors for vascular-targeted adenoviral gene delivery," *Hum Gene Ther.*, 11(14):1971-81, 2000.

Triantafilou et al., "Major histocompatibility class one molecule associates with glucose regulated protein (GRP) 78 on the cell surface," *Hum. Immunol.*, 62(8):764-770, 2001.

Tsimanis et al., "Over-expression of the functional interleukin-11 alpha receptor in the development of B-cell chronic lymphocytic leukemia," *Leuk. Lymphoma*, 42(1-2):195-205, 2001.

Uliss et al., "Retinitis pigmentosa and retinal neovascularization," *Ophthalmology*, 93:1599-1603, 1986.

Verma and Somia, "Gene therapy-promises, problems, and prospects," *Nature*, 389:239-242, 1997.

Volpert et al., "Captopril inhibits angiogenesis and slows the growth of experimental tumors in rats ," *J. Clin. Invest.*, 98(3):671-679, 1996.

Walsh et al., "Sequential development of angiotensin receptors and angiotensin I converting enzyme during angiogenesis in the rat subcutaneous sponge granuloma ," *Br. J. Pharmacol.*, 120(7):1302-1311, 1997.

Wang et al., "Prohibitin, a potential tumor suppressor, interacts with RB and regulates E2F function," *Oncogene*, 18(23):3501-3510, 1999.

Wang et al., "Rapid antibody responses by low-dose, single-step, dendritic cell-target immunization," *Proceedings of the National Academy of Sciences of the United States of America*, 97:847-852, 2000.

Watkins et al., "The 'adenobody' approach to viral targeting: specific and enhanced adenoviral gene delivery," *Gene Ther.*, 4:1004-1012, 1997.

Watson et al., "Variability among human umbilical vein endothelial cultures," *Science*, 268:447-448, 1995.

Weitzman et al., "Adenovirus vectors in cancer gene therapy," In: *Gene TherapyTechnology and Vector Systems*, 2:17-25, 1997.

Whaley et al., "Selection of peptides with semiconductor binding specificity for directed nanocrystal assembly," *Nature*, 405:665-668, 2000.

Wickham et al., "Targeted adenovirus gene transfer to endothelial and smooth muscle cells by using bispecific antibodies," *J. Virol.*, 70:6831-6838, 1996.

Wickham et al., "Targeted adenovirus-mediated gene delivery to T cells via CD3," *J. Virol.*, 71(10):7663-7669, 1997.

Wickham et al., "Targeting adenovirus," *Gene Ther.*, 7:110-114, 2000.

Wickham et al., "Targeting endothelium for gene therapy via receptors up-regulated during angiogenesis and inflammation," *Cancer Immunol. Immunother.*, 45:149-151, 1997.

Wu et al., "Molecular cloning of the murine BP-1/6C3 antigen: a member of the zinc-dependent metallopeptidase family ," *Proc. Natl. Acad. Sci., USA*, 87(3):993-997, 1990.

Wu, "In vivo veritas: live phage display panning," *Nature Biotechnology*, 14:429-431, 1996.

Yang and Reisfeld, "Doxorubicin conjugated with a monoclonal antibody directed to a human melanoma-associated proteoglycan suppresses the growth of established tumor xenografts in nude mice," *Proc. Natl. Acad. Sci., USA*, 85:1189-1193, 1988.

Yanovski et al., "Endocrine and metabolic evaluation of human immunodeficiency virus-infected patients with evidence of protease inhibitor-associated lipodystrophy," *J. Clin. Endocrin. Metab.*, 84(6):1925-1931, 1999.

Yao et al. "Targeting pancreatic islets with phage display assisted by laser pressure catapult microdissection," *The American Journal of Pathology*, 166:625-636, 2005.

Yoshiji et al., "The angiotensin-I-converting enzyme inhibitor perindopril suppresses tumor growth and angiogenesis: possible role of the vascular endothelial growth factor ," *Clin. Cancer Res.*, 7(4):1073-1078, 2001.

Zempo et al., "Regulation of vascular smooth muscle cell migration and proliferation in vitro and in injured rat arteries by a synthetic matrix metalloproteinase inhibitor ," *Arterioscler. Thromb. Vasc. Biol.*, 16:28-33, 1996.

Zhang et al., "Crystal structure of the obese protein leptin-E100," *Nature*, 387:206-209, 1997.

Zhang et al., "Development and application of adenoviral vectors for gene therapy of cancer," *Cancer Gene Therapy*, 6:113-138, 1999.

Zhang et al., "Inhibition of adipocyte differentiation by HIV protease inhibitors," *J. Clin. Endocrin. Metab.*, 84:4274-4277, 1999.

Zhang et al., "Positional cloning of the mouse obese gene and its human homologue," *Nature*, 372:425-432, 1994.

Zhu et al., "Mediation of lung metastasis of muring melanomas by a lung-specific endothelial cell adhesion molecule," *Proc. Natl. Acad. Sci., USA*, 88:9568-9572, 1991.

* cited by examiner

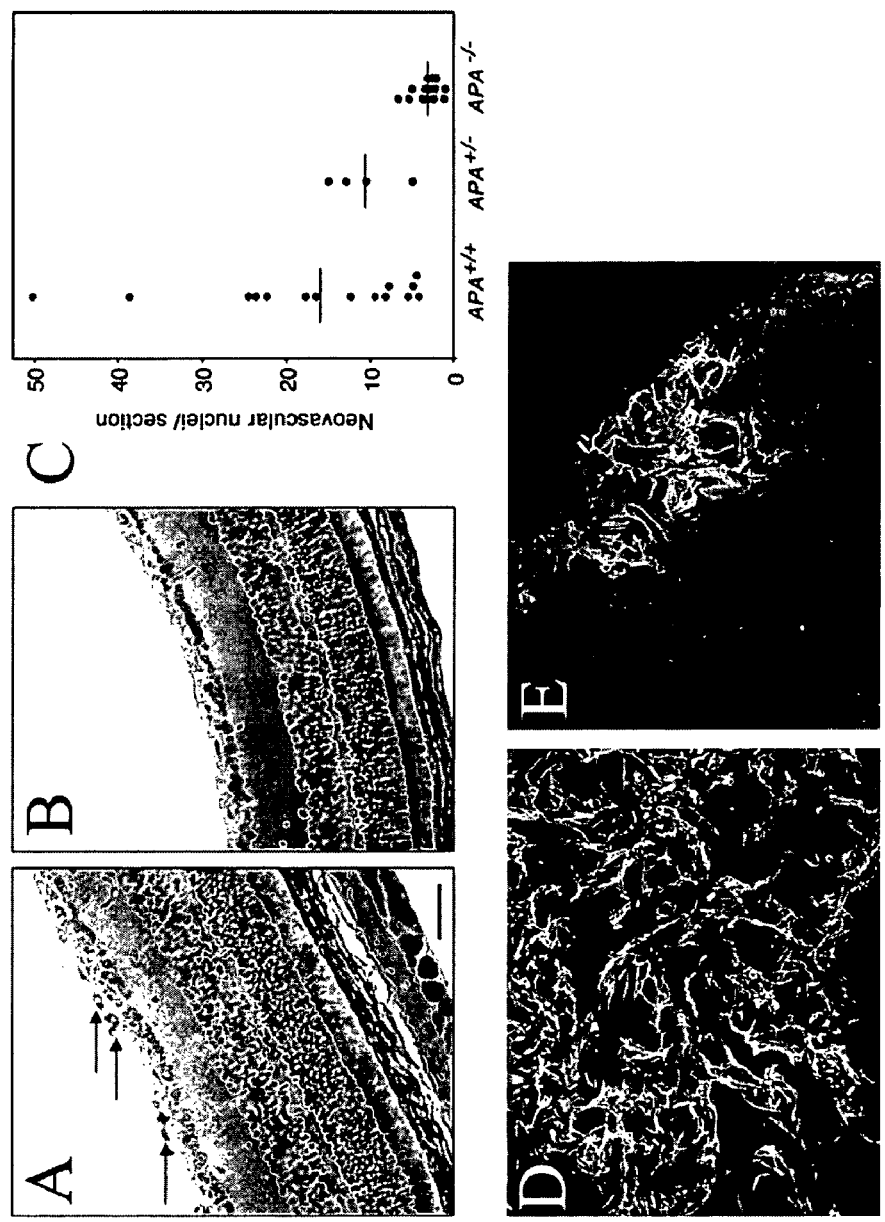
FIG. 1A-E

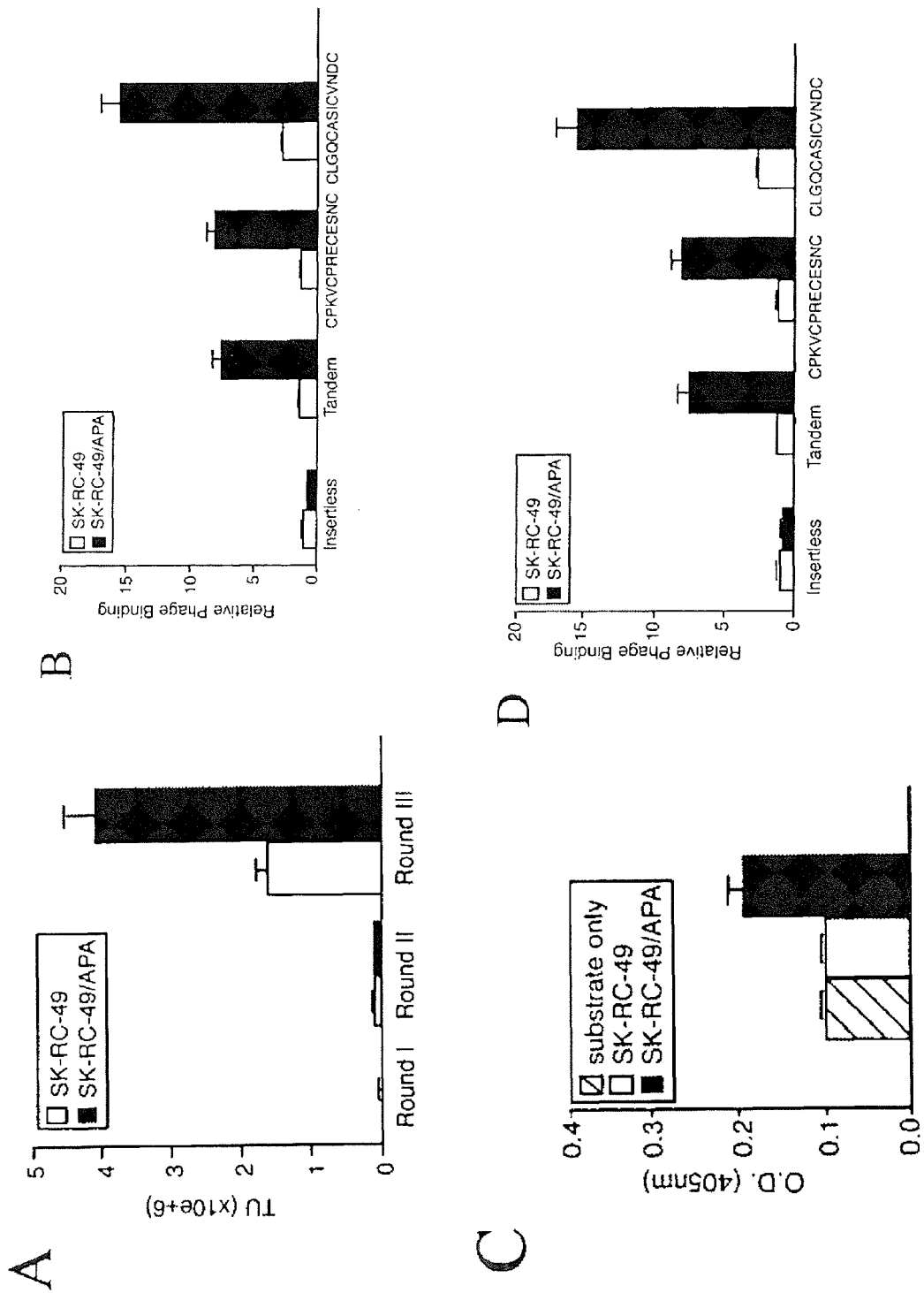
FIG. 2A-D

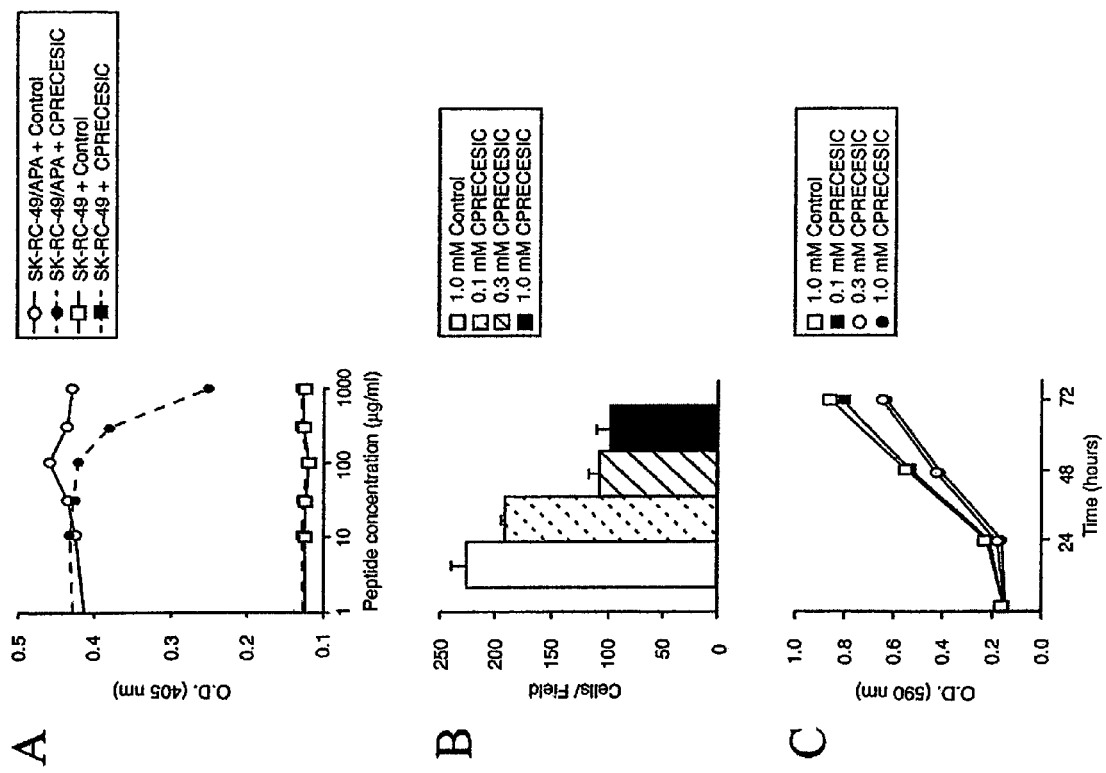
FIG. 3A-C

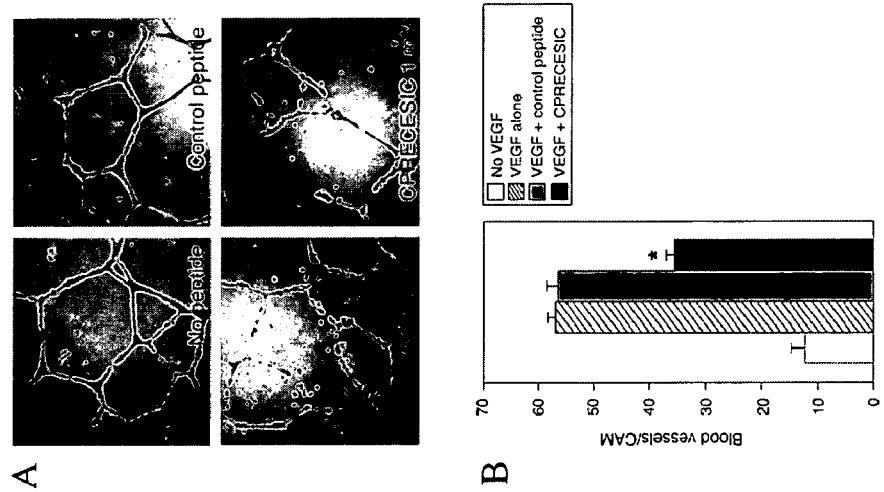
FIG. 4A-B

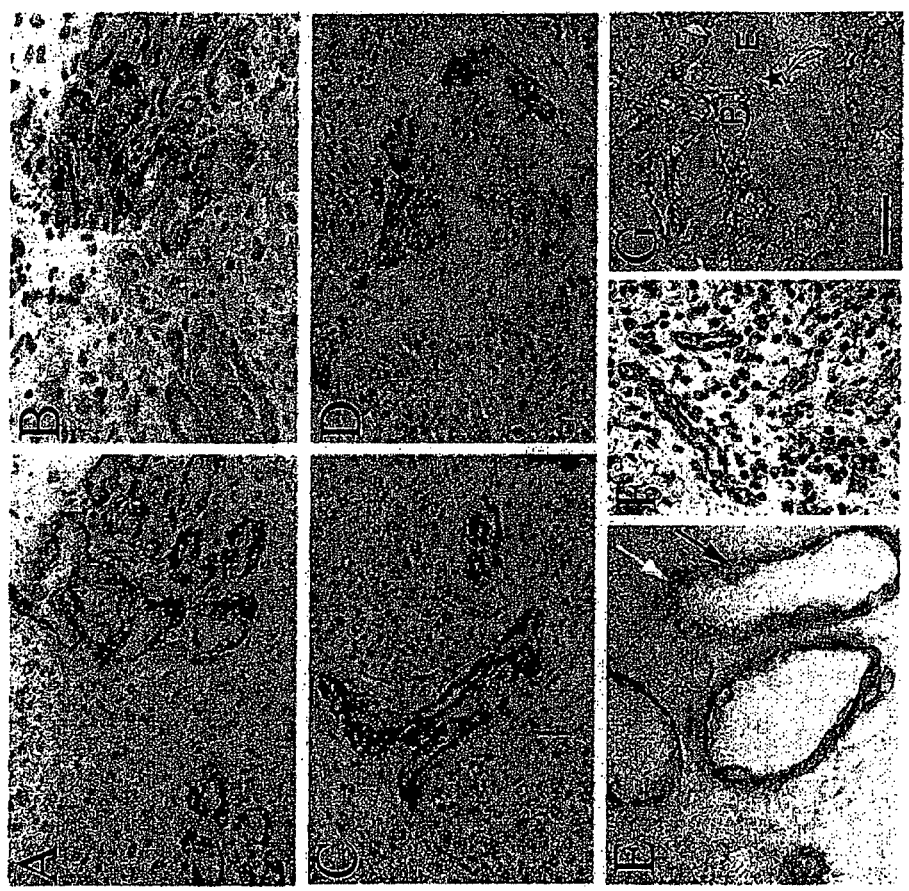
FIG. 5A-G

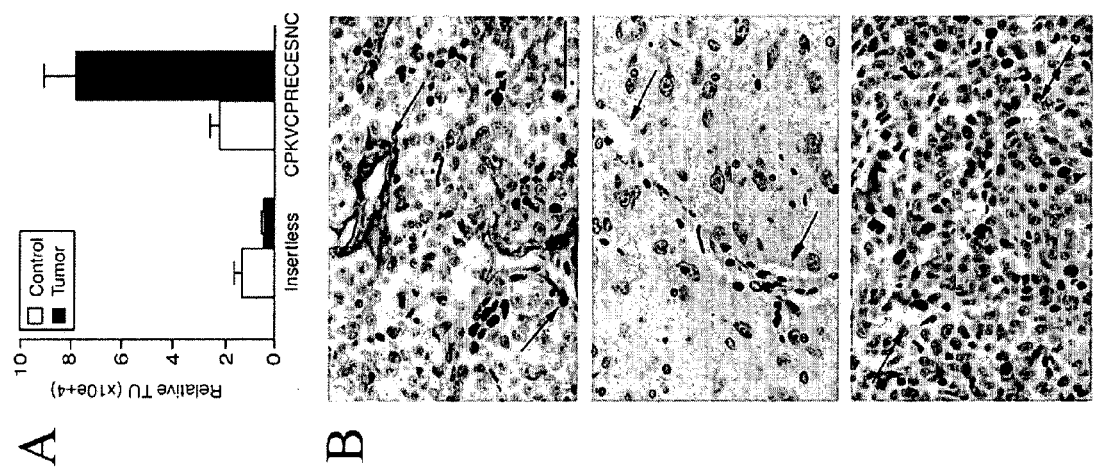
FIG. 6A-B

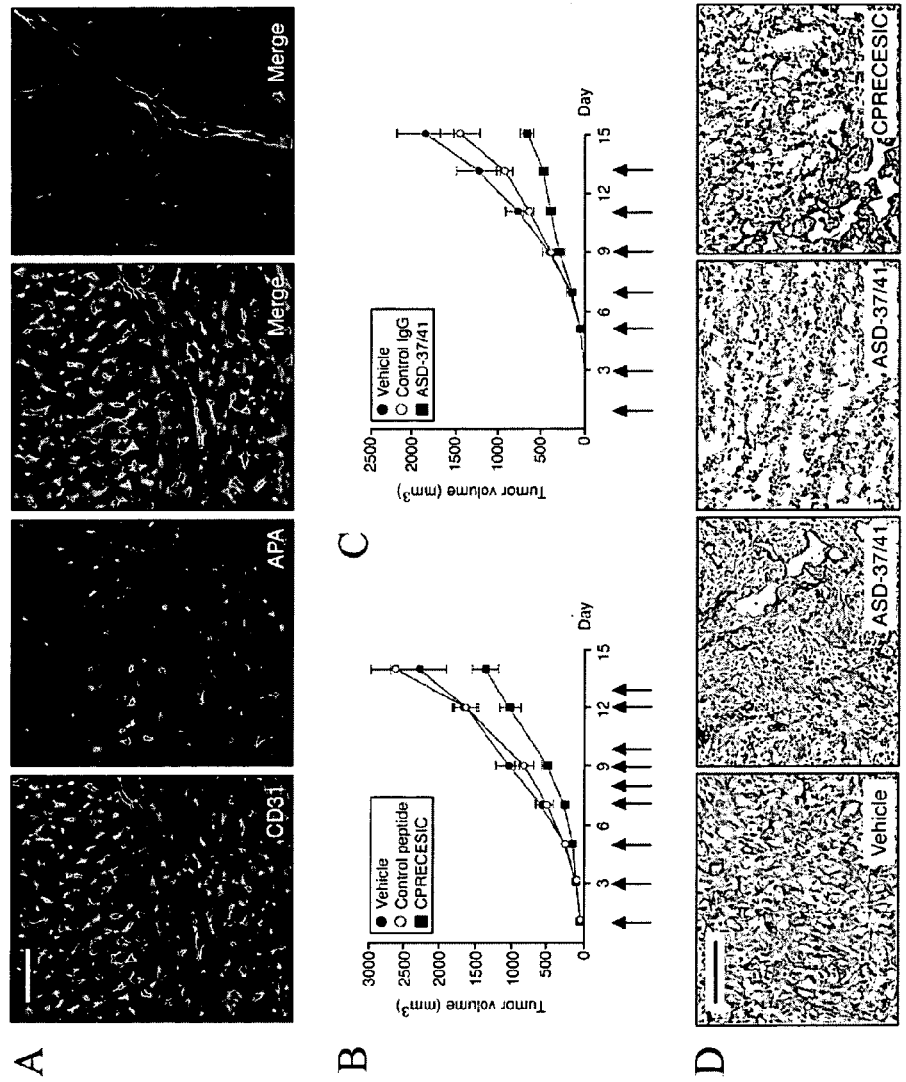
FIG. 7A-D

SEQUENCE LISTING

<160> NUMBER OF SEQ ID NOS: 19

<210> SEQ ID NO 1
<211> LENGTH: 31
<212> TYPE: PRT

```
<213> ORGANISM: Artificial Sequence
<220> FEATURE:
<223> OTHER INFORMATION: Description of Artificial Sequence:
      Synthetic Peptide

<400> SEQUENCE: 1

Cys Tyr Asn Leu Cys Ile Arg Glu Cys Glu Ser Ile Cys Gly Ala Asp
  1               5                  10                  15

Gly Ala Cys Trp Thr Trp Cys Ala Asp Gly Cys Ser Arg Ser Cys
             20                  25                  30

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 2

Cys Pro Arg Glu Cys Glu Ser Ile Cys
  1               5

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 3

Cys Pro Lys Val Cys Pro Arg Glu Cys Glu Ser Asn Cys
  1               5                  10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 4

Cys Leu Gly Gln Cys Ala Ser Ile Cys Val Asn Asp Cys
  1               5                  10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 5

Cys Pro Arg Glu Cys Glu Ser
  1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 6
```

```
Cys Pro Arg Glu Cys Glu Ser Asn
  1               5

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 7

Gly Ala Cys Val Arg Leu Ser Ala Cys Gly Ala
  1               5                  10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 8

Cys Pro Lys Val Cys Pro Arg Glu Cys Ser Asn Cys
  1               5                  10

<210> SEQ ID NO 9
<211> LENGTH: 31
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 9

Cys Tyr Asn Leu Cys Ile Arg Glu Cys Glu Ser Ile Cys Gly Ala Asp
  1               5                  10                  15

Gly Ala Cys Trp Thr Trp Cys Ala Asp Gly Cys Ser Arg Ser Cys
              20                  25                  30

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 10

Cys Gly Thr Gly Cys Ala Val Glu Cys Glu Val Val Cys
  1               5                  10

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 11

Cys Ala Val Ala Cys Trp Ala Asp Cys Gln Leu Gly Cys
  1               5                  10

<210> SEQ ID NO 12
<211> LENGTH: 13
<212> TYPE: PRT
```

```
<213> ORGANISM: Artificial Sequence
<220> FEATURE:
<223> OTHER INFORMATION: Description of Artificial Sequence:
      Synthetic Peptide

<400> SEQUENCE: 12

Cys Ser Gly Leu Cys Thr Val Gln Cys Leu Glu Gly Cys
 1               5                  10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 13

Cys Ser Met Met Cys Leu Glu Gly Cys Asp Asp Trp Cys
 1               5                  10

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence:
      Synthetic Peptide
<220> FEATURE:
<221> NAME/KEY: modified_res
<222> LOCATION: (2)..(12)
<223> OTHER INFORMATION: xaa = can be any naturally occurring amino
      acid

<400> SEQUENCE: 14

Cys Xaa Xaa Xaa Cys Xaa Xaa Xaa Cys Xaa Xaa Xaa Cys
 1               5                  10

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 15

Lys Leu Ala Lys Leu Ala Lys
 1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 16

Lys Leu Ala Lys Lys Leu Ala
 1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence:
      Synthetic Peptide
```

```
<400> SEQUENCE: 17

Lys Ala Ala Lys Ala Ala
 1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 18

Lys Leu Gly Lys Lys Leu Gly
 1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence:
      Synthetic Peptide

<400> SEQUENCE: 19

Gly Ala Asp Gly Ala
 1               5
```

AMINOPEPTIDASE A (APA) TARGETING PEPTIDES FOR THE TREATMENT OF CANCER

This application is a divisional of U.S. Ser. No. 10/784,537, filed on Feb. 23, 2004, now U.S. Pat. No. 7,420,030 which is a continuation in part of PCT application PCT/US02/27836, filed on Aug. 30, 2002, which is a continuation in part of PCT application PCT/US01/27692, filed on Sep. 7, 2001, and the entire texts of each application is incorporated herein by reference. The PCT/US01/27692 application claims priority from U.S. Provisional Patent Application No. 60/231,266 filed Sep. 8, 2000, and U.S. Provisional Patent Application No. 60/367,381 converted from U.S. patent application Ser. No. 09/765,101, filed Jan. 17, 2001.

This invention was made with U.S. government support under grants CA90270 and CA82976 to R.P.; CA90270 and CA90810 to W.A. from the National Institutes of Health. The U.S. government has certain rights in the present invention.

BACKGROUND OF THE INVENTION

Field of the Invention

The present invention concerns the fields of molecular medicine and targeted delivery of therapeutic agents. More specifically, the present invention relates to the identification of aminopeptidase A (APA) as a therapeutic target in angiogenic blood vessels, and the present invention provides methods and compositions relating to targeting aminopeptidase A for the treatment of cancer.

DESCRIPTION OF RELATED ART

Phage display or biopanning is a technique which can be used to identify specific peptide sequences that can bind to a target molecule, cell, tissue, or organ. Phage display is a technique in which a phage library expresses, for example, a set of random peptide sequences of defined length, incorporated into a phage coat protein (e.g., Smith and Scott, 1985; Smith and Scott, 1993). Peptide sequences that bind to a target molecule, cell, tissue or organ may be identified by incubating a phage display library with the target and selecting for bound peptides (biopanning) (e.g., Pasqualini and Ruoslahti, 1996; Arap et al., 1998a). Unbound phage may be washed away and bound phage eluted and collected. The collected phage may be amplified and taken through further binding/amplification cycles to enrich the pool of peptides for those that selectively and/or specifically bind to the target. With each cycle, the proportion of phage in the pool that contain targeting peptides for the target of interest is enriched. After several cycles, individual phage clones may be characterized by DNA sequencing to identify the targeting peptide sequences.

Biopanning may be used to select or identify peptides that can be used in developing new therapies or therapeutic compositions or enhancing existing therapies. For instance, cancer continues to be a serious problem in society, resulting in significant mortality rates. The realization that angiogenic vasculature is a target for intervention in cancer has long led to an interest in endothelial cell receptors associated with tumor blood vessels and their corresponding ligands. However, so far only a few such receptors have been identified. Even less is known about the function and physiologic significance of these receptors, which include aminopeptidase A.

Aminopeptidase A (glutamyl-aminopeptidase, EC 3.4.11.7, APA) is a homodimeric type II membrane-spanning cell surface protein with zinc metallopeptidase activity that hydrolyzes N-terminal glutamyl or aspartyl residues from oligopeptide substrates (Nanus et al., 1993; Wu et al., 1990). Upregulation of APA has been reported in perivascular cells (termed "pericytes") of tumor blood vessels (Alliot et al., 1999a; Schlingemann et al., 1996; Juillerat-Jeanneret et al., 2003; Juillerat-Jeanneret et al., 2000; Bogenreider et al., 1997; Alliot et al., 1999b); however, no role or physiologic function has been established for APA in tumor blood vessels.

Targeting peptides that exhibit selective and/or specific binding for aminopeptidase A have not been previously reported in the literature. Further characterization of APA is needed.

SUMMARY OF THE INVENTION

The present invention overcomes deficiencies in the prior art by both identifying aminopeptidase A as a functional target in tumor vasculature and providing methods and compositions for targeting and modulating aminopeptidase A. Targeting and modulation of APA may be used, for example, in the treatment of cancer or other disease states associate with angiogenesis or vascular growth. In certain embodiments, the invention concerns APA targeting moieties, which include peptides and antibodies, selective and/or specific for aminopeptidase A. Exemplary targeting peptides include, but are not limited to SEQ ID NO:1, SEQ ID NO:2 and SEQ ID NO:3. Other embodiments concern such targeting peptides attached to therapeutic or diagnostic agents. In certain embodiments, the therapeutic agent may be a virus. Viruses can be produced that express or incorporate APA targeting peptides; these viruses can then be used for targeted gene therapy for the treatment of cancer or other disease states that are associated with angiogenesis or vascularization. The ability to selectively target APA in the vasculature in and/or near tumors with peptides, modified peptides, antibodies, diagnostic agents, and/or therapeutic agents, such as viruses, provides a significant advantage for the increased efficacy and potency of treatments.

Embodiments of the invention concern isolated peptides, preferably of 100 amino acids or less, comprising at least three contiguous amino acids of a targeting peptide sequence identified by the biopanning methods described herein. An APA targeting peptide of the invention may, even more preferably be 50, 30, 20, 10 or 5 amino acids or less including all intervening peptide lengths. The peptide may comprise 4, 5, 6, 7, 8, 9, 10, 11, 12, 13, 14, 15, 16, 17, or 18 contiguous amino acids of one or more targeting peptide sequences identified by the methods described herein. An APA targeting peptide may include, but is not limited to one or more of the amino acid sequences provided in SEQ ID NO:1, SEQ ID NO:2 and SEQ ID NO:3. One or more of the isolated peptides can be administered to a subject for the treatment of disease. In certain embodiments the disease may be cancer. The peptides may be administered to a subject, which include humans, but also may include other animals as well. The isolated peptide may be in a pharmaceutically acceptable carrier.

In still further embodiments of the invention, antibodies that bind to APA may be used. Antibodies may be derived that bind APA or anti-idiotopes of APA targeting peptides. An antibody specific for APA may be administered to a subject for the treatment of a disease state associated with angiogenesis or vascularization, including cancer. In certain embodiments a virus may be engineered to express the isolated peptide.

In certain embodiments, an APA targeting moiety may be operatively coupled to a second molecule or substance. In preferred embodiments, the attachment is a covalent attachment. In various embodiments, the second molecule or substance is a diagnostic agent, a drug, a chemotherapeutic agent, a radioisotope, a pro-apoptosis agent, a cytotoxic agent, a peptide, a protein, an antibiotic, an antibody, a Fab fragment of an antibody, or an anti-angiogenic factor. These molecules or substances are representative only and virtually any molecule that may yield a therapeutic or diagnostic benefit for the treatment of cancer may be attached to an APA targeting moiety and/or administered to a subject within the scope of the invention. In preferred embodiments, the pro-apoptotic agent is etoposide, ceramide sphingomyelin, Bax, Bid, Bik, Bad, caspase-3, caspase-8, caspase-9, fas, fas ligand, fadd, fap-1, tradd, faf, rip, reaper, apoptin, interleukin-2 converting enzyme or annexin V.

In other preferred embodiments, the anti-angiogenic agent is angiostatin5, pigment epithelium-derived factor, angiotensin, laminin peptides, fibronectin peptides, plasminogen activator inhibitors, tissue metalloproteinase inhibitors, interferons, a cytokine such as interleukin 12, platelet factor 4, IP-10, Gro-β, thrombospondin, 2-methoxyoestradiol, proliferin-related protein, carboxiamidotriazole, CM101, Marimastat, pentosan polysulphate, angiopoietin 2 (Regeneron), interferon-alpha, herbimycin A, PNU145156E, 16K prolactin fragment, Linomide, thalidomide, pentoxifylline, genistein, TNP-470, endostatin, paclitaxel, docetaxel, polyamines, a proteasome inhibitor, a kinase inhibitor, a signaling inhibitor (SU5416, SU6668, Sugen, South San Francisco, Calif.), accutin, cidofovir, vincristine, bleomycin, AGM-1470, platelet factor 4 or minocycline. In further preferred embodiments, the cytokine is interleukin 1 (IL-1), IL-2, IL-5, IL-10, IL-11, IL-12, IL-18, interferon-γ (IF-γ), IF-α, IF-β, tumor necrosis factor-α (TNF-α), or GM-CSF (granulocyte macrophage colony stimulating factor). Such examples are representative only and are not intended to exclude other pro-apoptosis agents, anti-angiogenic agents or cytokines known in the art.

In other embodiments of the invention, the isolated peptide may be attached to a macromolecular complex. In preferred embodiments, the macromolecular complex is a virus, a bacteriophage, a bacterium, a liposome, a microparticle, a nanoparticle (e.g., a gold nanoparticle), a magnetic bead, a yeast cell, a mammalian cell, a cell or a microdevice. These are representative examples only and macromolecular complexes within the scope of the present invention may include virtually any complex that may be attached to a targeting peptide and administered to a subject. In other preferred embodiments, the isolated peptide may be attached to a eukaryotic expression vector, more preferably a gene therapy vector.

In a further embodiment, the isolated peptide may be attached to a solid support, preferably magnetic beads, Sepharose beads, agarose beads, a nitrocellulose membrane, a nylon membrane, a column chromatography matrix, a high performance liquid chromatogaphy (HPLC) matrix or a fast performance liquid chromatography (FPLC) matrix.

Certain embodiments of the invention concern isolated nucleic acids. In certain aspects the nucleic acids may be 300 nucleotides or less in length. In still further embodiments the nucleic acids may be 270, 240, 210, 180, 150, 120, 90, 60, 30 or even 9 nucleotides in length. Exemplary non-limiting nucleic acid sequences include those that encode the APA targeting peptides provided in SEQ ID NO:1, SEQ ID NO:2 or SEQ ID NO:3. In preferred embodiments, one or more isolated nucleic acid is incorporated into a eukaryotic or a prokaryotic expression vector. In even more preferred embodiments, the vector is a plasmid, a cosmid, a yeast artificial chromosome (YAC), a bacterial artificial chromosome (BAC), a virus or a bacteriophage. In other preferred embodiments, the isolated nucleic acid is operatively linked to a leader sequence that localizes the expressed peptide to the extracellular surface of a host cell.

In certain embodiments, the isolated peptide inhibits either aminopeptidase A activity, angiogenesis or both. The isolated peptide may be a therapeutic for disease states with associated angiogenesis, for example cancer or diabetic retinopathy.

In still further embodiments, the invention include pharmaceutical compositions comprising a targeting moiety that selectively binds aminopeptidase A, including peptides and antibodies.

Certain embodiments include methods for the treatment of cancer comprising administering an anti-aminopeptidase A antibody to a subject. The subject may be a mammal and inparticular a human. The antibody may be a monoclonal antibody. The antibody is typically administered in a pharmaceutically acceptable carrier. In further embodiments, the method may further comprise administering a second therapeutic agent to said human.

Further embodiments include methods of treating a disease associated with neo-vascularization comprising administering a peptide that selectively binds aminopeptidase A. The peptide may inhibit aminopeptidase A. The peptide may be selected from the group consisting of SEQ ID NO:1, SEQ ID NO:2, or SEQ ID NO:3. The subject may be a mammal and is typically a human. The peptide is administered in a pharmaceutically acceptable carrier. The method may further comprise administering a second therapeutic agent to said human. The peptide may be operatively coupled and in particular covalently coupled to a therapeutic agent. A therapeutic agent may be a drug, a chemotherapeutic agent, a radioisotope, a pro-apoptosis agent, an anti-angiogenic agent, a hormone, a cytokine, a cytotoxic agent, a cytocidal agent, a cytostatic agent, a peptide, a protein, an antibiotic, an antibody, a Fab fragment of an antibody, a hormone antagonist, a nucleic acid or an antigen. The anti-angiogenic agent is selected from the group consisting of thrombospondin, angiostatin5, pigment epithelium-derived factor, angiotensin, laminin peptides, fibronectin peptides, plasminogen activator inhibitors, tissue metalloproteinase inhibitors, interferons, interleukin 12, platelet factor 4, IP-10, Gro-β, thrombospondin, 2-methoxyoestradiol, proliferin-related protein, carboxiamidotriazole, CM101, Marimastat, pentosan polysulphate, angiopoietin 2 (Regeneron), interferon-alpha, herbimycin A, PNU145156E, 16K prolactin fragment, Linomide, thalidomide, pentoxifylline, genistein, TNP-470, endostatin, paclitaxel, Docetaxel, polyamines, a proteasome inhibitor, a kinase inhibitor, a signaling peptide, accutin, cidofovir, vincristine, bleomycin, AGM-1470, platelet factor 4 and minocycline. Whereas, the pro-apoptosis agent is selected from the group consisting of etoposide, ceramide sphingomyelin, Bax, Bid, Bik, Bad, caspase-3, caspase-8, caspase-9, fas, fas ligand, fadd, fap-1, tradd, faf, rip, reaper, apoptin, interleukin-2 converting enzyme or annexin V. Additional apoptotic agents include gramicidin, magainin, mellitin, defensin, cecropin, (KLAKLAK)2 (SEQ ID NO:15), (KLAKKLA)2 (SEQ ID NO:16), (KAAKKAA)2 (SEQ ID NO:17) or (KLGKKLG)3 (SEQ ID NO:18). Furthermore, a cytokine may be selected from the group consisting of interleukin 1 (IL-1), IL-2, IL-5, IL-10, IL-11, IL-12, IL-18, interferon-γ (IF-γ), IF-α, IF-β, tumor necrosis factor-α (TNF-α), or GM-CSF (granulocyte macrophage colony stimulating factor).

In yet further embodiments of the invention include methods for imaging cells expressing aminopeptidase A comprising exposing a sample to an isolated peptide that selectively binds aminopeptidase A, wherein said peptide is coupled to a second agent. The agent may be a radioisotope or an imaging agent. The cells may comprise vasculature, in particular vasculature associated with a disease state, such as a tumor. Isolated peptide may comprise SEQ ID NO:1, SEQ ID NO:2, or SEQ ID NO:3.

In still further embodiments include a peptide that selectively binds aminopeptidase A isolated by the method comprising: a) contacting a cell or tissue expressing APA with a plurality of phage, wherein each phage comprises heterologous peptide sequences incorporated into a fiber protein, b) removing the phage that do not bind to the cell or tissue expressing APA, and c) isolating the phage that bind the cell or tissue expressing APA. The method may be repeated at least twice and can be conducted 3, 4, 5, 6, 7, 8, 9, 10 times or more. The method may further comprising isolating and sequencing the isolated phage nucleic acid. APA expression in a cell ro tissue may be endogenous or exogenous expression.

BRIEF DESCRIPTION OF THE DRAWINGS

FIGS. 1A-E. APA-deficient mice have an impaired angiogenesis phenotype. $APA^{-/-}$, $APA^{+/-}$ and $APA^{+/+}$ mouse pups were exposed to 75% oxygen (from P7 to P12) and eyes were enucleated on P19. Paraffin sections were stained with H&E. FIG. 1A, A large number of new blood vessels are seen protruding from the retina into the vitreous space in wild type ($APA^{+/+}$) eyes (arrows point to endothelial cell nuclei), while no neovasculature is present in $APA^{-/-}$ eyes (FIG. 1B). Scale bar: 50 µm. FIG. 1C, The number of neovascular nuclei protruding into the vitreous space was quantified by evaluating several serial sections of multiple eyes. Each circle represents the mean of at least ten eye sections. A horizontal bar represents the mean of the group. FIG. 1D and FIG. 1E, Gelfoam sponges impregnated with VEGF, bFGF, and TGF-α were implanted in the subcutaneous tissue of $APA^{-/-}$ and $APA^{+/+}$ mice. Sponges were removed 14 days later and sections were stained with anti-CD31 antibody to visualize the endothelial cells. A large number of endothelial cells (2.55±0.08 area units) are seen protruding to the sponges in $APA^{+/+}$ mice (FIG. 1D) while the number of new blood vessels is smaller (0.73±0.01 area units, P<0.001) in the sponge implanted in $APA^{-/-}$ mice (FIG. 1E). Scale bar: 250 µm.

FIGS. 2A-D. Selection and identification of APA-binding peptides. FIG. 2A, A phage peptide library was pre-absorbed on APA negative SK-RC-49 cell line and incubated with stably APA-transfected SK-RC-49 cells. Cell-bound phage were recovered by infection and used for further rounds of panning on SK-RC-49/APA cells. By the third round of selection, strong enrichment was observed in phage binding to APA-transfected SK-RC-49 cells. Shown are mean±standard error of the means (SEM) from triplicate samples. FIG. 2B, Binding of the selected phage clones to SK-RC-49/APA cells was compared to binding to SK-RC-49 cells. Insertless fd-tet phage was used as a negative control. The designation tandem refers to the peptide sequence CYNLCIRECESICGADGACWTWCADGCSRSC (SEQ ID NO:1). Phage binding to the cells is shown relative to the negative control phage binding to the parental SK-RC-49 cells (value was set to be 1). Shown are mean±SEM from triplicate samples. FIG. 2C, APA was immobilized on RC38-coated microwells from SK-RC-49/APA cell lysates, and APA enzyme activity was evaluated with the specific substrate α-glutamyl-p-nitroanilide by measuring absorbance. RC38-immobilized SK-RC-49 cell lysate showed no activity above background from the substrate alone. Shown are mean±SEM from triplicate samples. FIG. 2D: Binding of the selected phage clones to RC38-immunocaptured APA was compared to the binding to RC38-immunocaptured SK-RC-49 cell lysate. The individual wells were then incubated with equal amounts of each individual phage. Insertless fd-tet phage was used as a negative control for the phage binding. Phage binding to immunocaptured APA is shown relative to the negative control phage binding to immunocaptured SK-RC-49 cell lysate (value was set to be 1). Shown are mean±SEM from triplicate samples.

FIGS. 3A-C. CPRECESIC (SEQ ID NO:2) is a specific inhibitor of APA activity and blocks endothelial cell migration and proliferation. FIG. 3A, APA enzymatic activity in SK-RC-49/APA cells was measured in the presence of increasing concentrations of either targeting or control peptide. SK-RC-49 cells served as a negative control. FIG. 3B, human microvascular endothelial cell (HMECs) were stimulated with complete M199 culture medium. Migration assay was performed in a Boyden microchemotaxis chamber. Cells were allowed to migrate through an 8 µm pore filter for 5 h at 37° C. in the presence of increasing concentrations of CPRECESIC (SEQ ID NO:2) or control peptides. Cells migrating through the membrane were stained and five high-power fields for each microwell were counted. Shown are means±SEM from triplicate wells. FIG. 3C, HMECs were stimulated with complete M199 culture medium in the presence of increasing concentrations of APA-binding or control peptides. Cell proliferation was measured at 24, 48 and 72 hours by a colorimetric assay based on crystal violet staining.

FIGS. 4A-B. Inhibition of angiogenesis by CPRECESIC (SEQ ID NO:2). FIG. 4A, HMECs were plated on Matrigel in the presence of increasing concentrations of APA-binding or control peptides and photographed after 24 hours (magnification: 40×). FIG. 4B, Eight-day-old chicken egg chorioallantoic membranes (CAMs) were implanted with PBS- or VEGF-adsorbed sponges. CPRECESIC (SEQ ID NO:2) or control peptides were tested at 1 mM concentration in the VEGF-adsorbed sponge. At day 12, CAMs were evaluated and the number of neovessels quantified. There were significantly fewer blood vessels in the CAMs treated with APA-binding peptides (*t test, P<0.01). Shown are means±SEM from triplicate samples.

FIGS. 5A-G. APA expression and activity in human brain tumor blood vessels. RC38 immunohistochemistry (FIG. 5A and FIG. 5C) and APA enzyme activity (FIG. 5B and FIG. 5D) of an area of glomeruloid vascular proliferation in glioblastoma multiforme (FIG. 5A and FIG. 5B) and in brain metastases from squamous cell carcinoma of the lung (FIG. 5C and FIG. 5D). Note the similar distribution of reaction products in both primary (FIG. 5A and FIG. 5B) and metastatic tumors (FIG. 5C and FIG. 5D), and the absence of staining of endothelial cells lining the vascular lumina, findings consistent with a localization of APA in the perivascular cells of these microvessels. Scale bar: 50 µm. FIG. 5E, Double staining of human adenocarcinoma metastasis to the brain with anti-APA antibody (RC38) and the anti endothelial cell antibody (PAL-E). RC38 was detected by using DAB as the substrate producing brown staining of perivascular cells (white arrow) and PAL-E was detected by using 4-chloro-1-naphtol as the substrate producing blue-gray staining of endothelial cells (black arrow). Note the absence of the RC38 staining in PAL-E positive cells. Scale bar: 50 µm. FIG. 5F, RC38 immunohistochemistry of an area of human granulation tissue. Scale bar: 50 µm. FIG. 5G, RC38 immuno-electron microscopy of an area of glomeruloid vascular proliferation in human glioblastoma multiforme. Perivascular cells (P) are positive for RC38 staining whereas endothelial cells (E) are negative. Asterisk indicates the lumen. Scale bar: 5 µm.

FIGS. 6A-B. CPKVCPRECESNC (SEQ ID NO:3)-displaying phage targets tumor vasculature. FIG. 6A, The ability of the APA-binding phage to home to tumors was evaluated after intravenous administration into mice bearing human MDA-MB-435 breast carcinoma-derived tumor xenografts. Phage were recovered from tumor and control tissues after perfusion. Shown are mean±SEM of TU from triplicate platings. Brain was used as a control tissue. FIG. 6B, Phage displaying the peptide CPKVCPRECESNC (SEQ ID NO:3) or insertless negative control phage were injected intravenously into MDA-MB-435-derived tumor-bearing mice. An anti-phage antibody was used for staining. Arrows indicate blood vessels. The upper panel shows the tumor from the mouse that received the CPKVCPRECESNC (SEQ ID NO:3) phage; the middle panel shows the brain from the same mouse; the lower panel shows the tumor from the mouse that received the insertless control phage. Scale bar: 70 µm.

FIGS. 7A-D. Treatment of tumor-bearing mice with APA-binding peptides or anti-APA blocking monoclonal antibodies can suppress tumor growth. FIG. 7A, Immunofluorescence staining of EF43-fgf4-derived tumors shows APA expression on tumor blood vessels. Frozen tumor sections were stained for CD31 and APA. CD31 was detected with a FITC-conjugated secondary antibody and APA was detected with a Cy3-conjugated secondary antibody; merged images indicate that APA expression is vascular and not detectable on EF43-fgf4 cells. Scale bar: 125 µm (or 250 µm, far right panel). FIG. 7B, Balb/c mice bearing EF43-fgf4-derived tumors were divided in 3 size-matched cohorts (n=7 mice per group) that received vehicle (DMEM), CPRECESIC (SEQ ID NO:2) peptide or control (CARAC) peptide. Peptides were administered at 250 µg/mouse/dose (indicated by arrows). Shown are mean tumor volumes±SEM. FIG. 7C, Balb/c mice bearing EF43-fgf4-derived tumors were divided in 3 size-matched cohorts (n=7 mice per group) that received vehicle (DMEM), ASD-37/41 antibodies, or isotype control (rat IgG). Antibodies were administered at 200 µg/mouse/dose (indicated by arrows). Shown are mean tumor volumes±SEM. FIG. 7D, after treatments (FIG. 7B and FIG. 7C) were terminated at two weeks, tumor sections were immunostained for CD31 and counterstained by hematoxylin. Representative histopathological panels are shown as indicated. Relatively to controls (far left panel), ASD-37/41-treated tumors (middle panels) contained co-dominant areas of disrupted vascular structure next to islands of viable tissue (middle left panel) as well as large areas tumor destruction with extensive cell death (middle right panel); inhibitory peptides also had an evident effect on treated tumors (far right panel). Scale bar: 100 µm.

DESCRIPTION OF ILLUSTRATIVE EMBODIMENTS

The present invention overcomes deficiencies in the prior art by both identifying aminopeptidase A (APA) as a molecular marker and mediator of vasculature development, as well as providing methods and compositions for targeting APA with therapeutic and/or diagnostic agents, e.g., for the treatment of cancer. In certain embodiments, the invention concerns particular targeting moieties, e.g., peptides or antibodies, selective or specific for APA, including but not limited to the peptides set forth in SEQ ID NO:1, SEQ ID NO:2 and SEQ ID NO:3. Other embodiments concern APA targeting moieties that are operatively coupled to therapeutic or diagnostic agents. In certain embodiments, a therapeutic agent is a virus that can be engineered to express or has incorporated in or associated with its viral envelope or fiber proteins APA targeting peptides. Targeted viruses may then be used for gene therapy for the treatment of various disease states, including cancer. The ability to selectively target APA in the vasculature in and/or near tumors with peptides, modified peptides, antibodies, viruses, and/or other affinity reagents provides a significant advantage for the treatment of cancer that may result in an increased efficacy and potency.

A. DEFINITIONS

As used herein in the specification, "a" or "an" may mean one or more. As used herein in the claim(s), in conjunction with the word "comprising," the words "a" or "an" may mean one or more than one. As used herein "another" may mean at least a second or more of an item.

A "targeting moiety" is a term that encompasses various types of affinity reagents that may be used to enhance the localization or binding of a substance to a particular location in an animal, including organs, tissues, particular cell types, diseased tissues or tumors. Targeting moieties may include peptides, peptide mimetics, polypeptides, antibodies, antibody-like molecules, nucleic acids, aptamers, and fragments thereof. In certain embodiments, a targeting moiety will enhance the localization of a substance to cells expressing APA extracellularly, i.e., APA being associated with the cell surface or associated with surrounding extracellular matrix. Selective binding of a targeting moiety of the present invention, e.g., an targeting peptide or antibody, as well as variants and fragments thereof is when the targeting moiety binds a target (e.g., APA) and does not significantly bind to unrelated proteins. A targeting moiety is still considered to selectively bind even if it also binds to other proteins that are not substantially homologous with the target so long as such proteins share homology with a fragment or domain of the peptide target of the antibody. In this case, it would be understood that target moiety binding to the target is still selective despite some degree of cross-reactivity. Typically, the degree of cross-reactivity can be determined and differentiated from binding to the target.

A "targeting peptide" is a peptide comprising a contiguous sequence of amino acids, which is characterized by selective localization to an organ, tissue or cell type, which includes specific binding with an extracellular protein or molecule that is specifically expressed or produced in a specific tissue or cell type(s). Selective localization may be determined, for example, by methods disclosed below, wherein the putative targeting peptide sequence is incorporated into a protein that is displayed on the outer surface of a phage.

An exemplary method of identifying targeting peptides includes administrating to a subject a library of phage that have been genetically engineered to express a multitude of targeting peptides on their outer surface. Administration of the phage is followed by collection of one or more organs, tissues or cell types from the subject and identification of phage found in that organ, tissue or cell type. A phage expressing a targeting peptide sequence is considered to be selectively localized to a tissue or organ if it exhibits greater binding in that tissue or organ compared to a control tissue or organ. Preferably, selective localization of a targeting peptide should result in a two-fold or higher enrichment of the phage in the target organ, tissue or cell type, compared to a control organ, tissue or cell type. Selective localization resulting in at least a three-fold, four-fold, five-fold, six-fold, seven-fold, eight-fold, nine-fold, ten-fold or higher enrichment in the target organ compared to a control organ, tissue or cell type is more preferred. Alternatively, a phage expressing a targeting peptide sequence that exhibits selective localization preferably shows an increased enrichment in the target organ compared to a control organ when phage recovered from the target organ are reinjected into a second host for another round of screening. Further enrichment may be exhibited following a third round of screening. Another alternative means to determine selective localization is that phage expressing the putative target peptide preferably exhibit a two-fold, more preferably a three-fold or higher enrichment in the target organ compared to control phage that express a non-specific peptide or that have not been genetically engineered to express any putative target peptides. Another means to determine selective localization is that localization to the target organ of phage expressing the target peptide is at least partially blocked by the co-administration of a synthetic peptide containing the target peptide sequence. "Targeting peptide" and "homing peptide" are used synonymously herein.

An exemplary method of identifying a targeting peptides includes administrating to a subject a library of phage that have been genetically engineered to express a multitude of targeting peptides on their outer surface. Administration of the phage is followed by collection of one or more organs, tissues or cell types from the subject and identification of phage found in that organ, tissue or cell type. A phage expressing a targeting peptide sequence is considered to be selectively localized to a tissue or organ if it exhibits greater binding in that tissue or organ compared to a control tissue or organ. Preferably, selective localization of a targeting peptide should result in a two-fold or higher enrichment of the phage in the target organ, tissue or cell type, compared to a control organ, tissue or cell type. Selective localization resulting in at least a three-fold, four-fold, five-fold, six-fold, seven-fold, eight-fold, nine-fold, ten-fold or higher enrichment in the target organ compared to a control organ, tissue or cell type is more preferred. Alternatively, a phage expressing a targeting peptide sequence that exhibits selective localization preferably shows an increased enrichment in the target organ compared to a control organ when phage recovered from the target organ are reinjected into a second host for another round of screening. Further enrichment may be exhibited following a third round of screening. Another alternative means to determine selective localization is that phage expressing the putative target peptide preferably exhibit a two-fold, more preferably a three-fold or higher enrichment in the target organ compared to control phage that express a non-specific peptide or that have not been genetically engineered to express any putative target peptides. Another means to determine selective localization is that localization to the target organ of phage expressing the target peptide is at least partially blocked by the co-administration of a synthetic peptide containing the target peptide sequence. "Targeting peptide" and "homing peptide" are used synonymously herein. An exemplary method of identifying a targeting peptides includes administrating to a subject a library of phage that have been genetically engineered to express a multitude of targeting peptides on their outer surface. Administration of the phage is followed by collection of one or more organs, tissues or cell types from the subject and identification of phage found in that organ, tissue or cell type. A phage expressing a targeting peptide sequence is considered to be selectively localized to a tissue or organ if it exhibits greater binding in that tissue or organ compared to a control tissue or organ. Preferably, selective localization of a targeting peptide should result in a two-fold or higher enrichment of the phage in the target organ, tissue or cell type, compared to a control organ, tissue or cell type. Selective localization resulting in at least a three-fold, four-fold, five-fold, six-fold, seven-fold, eight-fold, nine-fold, ten-fold or higher enrichment in the target organ compared to a control organ, tissue or cell type is more preferred. Alternatively, a phage expressing a targeting peptide sequence that exhibits selective localization preferably shows an increased enrichment in the target organ compared to a control organ when phage recovered from the target organ are reinjected into a second host for another round of screening. Further enrichment may be exhibited following a third round of screening.

Another alternative means to determine selective localization is that phage expressing the putative target peptide preferably exhibit a two-fold, more preferably a three-fold or higher enrichment in the target organ compared to control phage that express a non-specific peptide or that have not been genetically engineered to express any putative target peptides. Another means to determine selective localization is that localization to the target organ of phage expressing the target peptide is at least partially blocked by the co-administration of a synthetic peptide containing the target peptide sequence. "Targeting peptide" and "homing peptide" are used synonymously herein.

A "phage display library" means a collection of phage that have been genetically engineered to express a set of putative targeting peptides on their outer surface. In preferred embodiments, DNA sequences encoding the putative targeting peptides are inserted in frame into a gene encoding a phage capsule protein. In other preferred embodiments, the putative targeting peptide sequences are in part random mixtures of all twenty amino acids and in part non-random. In certain preferred embodiments the putative targeting peptides of the phage display library exhibit one or more cysteine residues at fixed locations within the targeting peptide sequence. Cysteines may be used, for example, to create a cyclic peptide, which may provide a some structure to portions of the peptide.

A "receptor" for a targeting peptide includes but is not limited to any molecule or molecular complex that binds to a targeting peptide. Non-limiting examples of receptors include peptides, proteins, glycoproteins, lipoproteins, epitopes, lipids, carbohydrates, multi-molecular structures, and specific conformation of one or more molecules. In preferred embodiments, a "receptor" is a naturally occurring molecule or complex of molecules that is present on the lumenal surface of cells forming blood vessels within a target organ, tissue or cell type.

A "subject" refers generally to a mammal. In certain preferred embodiments, the subject is a mouse or rabbit. In even more preferred embodiments, the subject is a human.

B. AMINOPEPTIDASE A (APA) AND ANGIOGENESIS

Angiogenesis is a complex multi-step process that can occur in tumors or in response to various stimuli. Many lines of evidence indicate that tumor growth and angiogenesis depend on proteolytic activity. Angiogenic blood vessels express biochemical markers that are differentially expressed and whose functional importance has just begun to be uncovered. While only a few markers associated with angiogenic blood vessels have thus far been reported, it is remarkable that several are cell membrane-associated proteinases. By using genetic elimination and biochemical inhibition, the studies described herein demonstrate an as yet unrecognized mechanistic role for aminopeptidase A (APA) in pathological angiogenesis. Thus, specific APA inhibitors—such as peptidomimetics or anti-APA antibodies—may prove useful for targeting tumor vasculature.

The inventors have identified APA as a functional target for molecular agents that can inhibit angiogenesis. A decrease in neovascularization in APA $^{-/-}$ mice has been observed following induction of angiogenesis by hypoxia and by growth factors. Also, mice treated with APA inhibitors demonstrate reduced tumor growth. The data presented are reminiscent of those showing a stimulatory effect of angiotensins on endothelial cell migration (Kifor and Dzau, 1987) and proliferation (Monton et al., 1998). Angiotensin receptors are expressed in the CAM, suggesting that angiotensins might play a role in angiogenesis and capillary branching (Le Noble et al., 1996). The results, however, could also reflect a more general effect of APA on angiogenic mechanisms such as a role in degradation of extracellular matrix by processing other unknown substrates (Sang, 1998). Natural and synthetic inhibitors of other metalloproteases inhibit not only in vivo angiogenesis (Egeblad and Werb, 2002; Koivunen et al., 1999; Pasqualini et al., 2000; Sang, 1998) but also migration and proliferation of microvascular cells in vitro (Murphy et al., 1993; Zempo et al., 1996). Also, knockout mice in which other metalloproteases have been eliminated (such as MMP-2 or -9) show a defect in angiogenesis (reviewed in Egeblad and Werb, 2002).

Several approaches indicate that the vascular endothelium of angiogenic blood vessels express surface markers that are accessible from the circulation in tumors but are undetectable, inactive, or inaccessible in normal blood vessels. Such cell markers include growth factor receptors, cell adhesion molecules, proteoglycans, and proteases. Membrane-associated proteases such as gelatinases and aminopeptidases have been found to be molecular targets in tumor blood vessels (Koivunen et al., 1999; Pasqualini et al., 2000).

Here the inventors set out to determine the role of APA as a functional target for inhibition of angiogenesis. The genetic elimination of APA or biochemical inhibition of its enzymatic activity has lead to insights into the mechanisms of abnormal blood vessel formation. As describe herein, knockout APA $^{-/-}$ mice develop normally (Lin et al., 1998), but demonstrate a severely impaired angiogenic response to oxygen-induced retinopathy in a mouse model of retinopathy of prematurity. They also failed, compared to APA $^{+/+}$ mice, to sprout new blood vessels into subcutaneously implanted angiogenic factor-containing sponges (McCarty et al., 2002). The fact that APA $^{-/-}$ mice develop normally with no gross phenotypic abnormalities suggests that while APA may participate in embryonic angiogenesis, it is not an essential participant. The molecular events associated with de novo formation of blood vessels ("vasculogenesis") during early development may be redundant or compensated by other proteases. Data indicate a functional role for APA in the formation of new blood vessels from a preformed vascular bed ("angiogenesis"). These data support the candidacy of APA as a specific vascular target to inhibit abnormal angiogenesis associated with tumor formation and retinal neovascularization.

A combinatorial peptide library was screened to gain insights into the role of APA activity in angiogenesis, described below. Given the molecular diversity of the vasculature (St. Croix et al., 2000; Arap et al., 2002), this approach identifies probes to study APA function in endothelium-derived cells, and provides putative ligands to target tumor blood vessels in vivo. APA-binding phage displaying the sequences CYNLCIRECESICGADGACWTWCADGC-SRSC (SEQ ID NO:1), CPKVCPRECESNC (SEQ ID NO:3), and CLGQCASICVNDC (SEQ ID NO:4) were selected from initial screens. The first two phage clones bound specifically to APA and their binding was specifically inhibited by the cognate synthetic CPRECESIC (SEQ ID NO:2) motif. Binding of the CLGQCASICVNDC (SEQ ID NO:4) phage to APA was not inhibited by CPRECESIC peptide (SEQ ID NO:2), possibly due to the short sequence shared with the other isolated peptides leading to a low-affinity interaction; this result suggests that the sequence CPRECES (SEQ ID NO:5) alone is sufficient to promote inhibition. Functionally, the peptide CPRECES (SEQ ID NO:5) is the dominant sequence of the motif since another APA-binding peptide (CPRECESN; SEQ ID NO:6) was effective in vitro and also yielded therapeutic effects in vivo. A search of human databases for sequences homologous to the selected peptides did not yield matches consistent with potential APA-ligands. The biological substrate responsible for APA inhibition by the consensus motif CPRECESIC (SEQ ID NO:2) may remain unidentified until three-dimensional structure of the interaction of ligand peptides and the APA active site has been solved.

In vitro and in vivo angiogenesis assays are used define the functional basis for the role of APA in blood vessel formation. Evaluation of APA enzyme activity in freshly isolated endothelial cells led to the observation of high enzyme activity in human microvascular endothelial cell (HMECs) and in some tumor-derived endothelial cells (unpublished data), thus HMECs were employed in in vitro angiogenesis assays. The synthetic CPRECESIC (SEQ ID NO:2) peptide inhibited VEGF-induced migration and proliferation of HMECs and also inhibited cord/tube formation of microvascular endothelial cells in a Matrigel assay, as well as inhibiting angiogenesis in VEGF-stimulated CAMs. The consensus motif CPRECESIC (SEQ ID NO:2) is an inhibitor of APA enzymatic activity and a suppressor of migration and proliferation of endothelial cells. In addition, the inhibition of APA enzymatic activity leads to a dose-dependent decrease in cord/tube formation during angiogenesis.

Thus, APA is one of the many molecules that have been shown to play different roles, according to the organ and time period examined. A broad spectrum of tissues express APA (Li et al., 1993), but its only well understood role, prior to this disclosure, is the conversion of angiotensin II to angiotensin III in the renin-angiotensin system (Jackson, 2001). In vivo, angiotensin II remains the sole characterized substrate for APA. While angiotensins are usually investigated in relation to mechanisms of arterial hypertension, several studies suggest a possible role for angiotensins in blood vessel formation (Le Noble et al., 1996; Monton et al., 1998; Nadal et al., 2002; Walsh et al., 1997). Furthermore, inhibition of angiotensin-1-converting enzyme suppresses angiogenesis (Volpert et al., 1996; Yoshiji et al., 2001).

While APA is strongly expressed by angiogenic microvessels (Schlingemann et al., 1996) the inventors have confirmed that it is undetectable or barely detectable in normal vasculature. The involvement of angiotensins in angiogenesis referenced above and the overexpression of APA in angiogenic blood vessels suggest a mechanism for APA in neovascularization.

In addition to mouse models, the inventors evaluate whether abnormal angiogenesis associated with certain human diseases is related to APA in the vasculature. The expression and activity of APA in malignant gliomas and metastatic carcinomas to the brain were evaluated. APA is not only present in angiogenic blood vessels of human malignant gliomas, but the protein is overexpressed in the perivascular cells and is enzymatically active. In contrast, the presence of the enzyme and its corresponding proteolytic activity were undetectable in the blood vessels and adjacent normal brain.

Pericytes, which were once seen merely as the contractile microvessel equivalent of smooth muscle cells surrounding larger blood vessels, also play an active role in neovascularization and maturation, remodeling and maintenance of the vascular system (Morikawa et al., 2002; Schlingemann et al., 1991). Similarly to endothelial cells, perivascular cells also exhibit molecular, functional and structural heterogeneity (Morikawa et al., 2002), of which APA overexpression in tumor blood vessels is one example. APA may play a significant role in several functions of perivascular cells, such as secretion of growth factors, modulation of the extracellular matrix and regulation of vascular permeability.

The overexpression of APA in activated blood vessels has been associated with perivascular cells in human tumors here and elsewhere (Schlingemann et al., 1996) but the exact cellular location of active APA in the vascular endothelium of blood vessels during tumorigenesis is still not entirely clear. A further level of complexity arises because tumor cells express APA in several human cancers (Fujimura et al., 2000; Geng et al., 1998; Ino et al., 2000) making it difficult to differentiate the origin of APA enzymatic activity. In the studies described herein, the inventors show that APA expression and activity are strongly increased in tumor blood vessels during late stages of human malignant glioma progression. The inventors have also observed, that endothelial cells derived from mature macrovessels like human umbilical vein endothelial cells (HUVECs), express little or no APA, while HMECs, extracted from small, immature blood vessels show much higher APA expression (unpublished data). Once tumor blood vessels mature to the stage at which they are covered with perivascular cells, APA expression is reduced in the endothelial cells. In turn, activated perivascular cells covering more mature tumor blood vessels express high levels of APA. Due to its specific expression and accessibility to tumor blood vessels APA in the cell membranes of activated endothelial cells or perivascular cells can be systemically targeted, which makes it a suitable candidate for targeted imaging or therapy. Openings between defective endothelial cells of tumor blood vessels (Hashizume et al., 2000) enable access to the perivascular cell layer of the vasculature; other cell surface receptors of activated perivascular cells (such as the proteoglycan NG2) have been targeted by in vivo phage display (Burg et al., 1999). Combinatorial strategies targeting both the endothelial and perivascular cell compartments will provide improved efficacy for antiangiogenic therapies in multiple stages of tumorigenesis (Bergers et al., 2003).

Given that the selected APA-binding phage home to tumor vasculature, and the consensus motif deduced from APA-binding peptides specifically inhibit APA enzymatic activity, the inventors evaluated whether APA-binding peptides can be used as targeted inhibitory carriers. Although APA is also expressed in many cell types in normal tissues (Alliot et al., 1999; Li et al., 1993), studies show that APA is exposed, active, and available for binding to circulating ligands from the luminal side of the vascular endothelium because APA-binding phage selectively target tumor vasculature. Based on the phage recovery from tissues and phage immunohistochemistry, the inventors showed that the CPKVCPRECESNC (SEQ ID NO:3) phage targets angiogenic blood vessels in human breast carcinoma-derived tumor xenografts.

Finally, after documenting the expression of the target in the tumor vasculature, in a mouse model of mammary carcinoma (Deroarme et al., 1997, Hajitou et al., 2001), the inventors successfully targeted this tumor with the same APA-binding phage. The inventors show that APA-inhibitory ligands—such as the APA-binding peptides described herein or anti-APA monoclonal antibodies (Assmann et al. 1992)— specifically target angiogenic vasculature and can suppress tumor growth in vivo. The inventors determined the $IC_{50}$ of the ASD-37 monoclonal antibody for the APA enzyme activity and found it to be ~60 nM. The apparently superior inhibitory ability of anti-APA monoclonal antibodies is commensurate with and one likely explanation for the more evident histopathological findings observed after treatment with such antibodies relative to our APA-binding peptides. Considering these promising pre-clinical results, and the fact that antibody-related toxicity occurred only when mice received over 20-fold the doses that yielded the anti-tumor activity observed here (Assmann et al., 1992, Mentzel et al., 1999), anti-APA inhibitory antibodies are good drug development candidates.

In sum, a new role for APA and its targeted ligands in angiogenesis has been identified and exploited. The interaction between APA and its ligands has a functional role in abnormal angiogenesis. APA-binding peptides inhibit its proteolytic activity and affect endothelial cell functions and angiogenesis. The ligand motifs described herein may therefore serve as a targeting moiety, an antigen for the derivation of anti-idiotopic antibodies, and a template for peptidomimetic drug that modulate angiogenic mechanisms. The studies described herein show that APA is a specific vascular target for the modulation of pathologic angiogenesis.

II. APA TARGETING PEPTIDE IDENTIFICATION—PHAGE DISPLAY AND BIOPANNING

Targeting peptides selective for a given organ, tissue or cell type can be isolated by "biopanning" (Pasqualini and Ruoslahti, 1996; Pasqualini, 1999). In brief, a library of phage containing putative targeting peptides is administered to an animal or human and samples of organs, tissues or cell types containing phage are collected. In preferred embodiments utilizing filamentous phage, the phage may be propagated in vitro between rounds of biopanning in pilus-positive bacteria. The bacteria are not lysed by the phage but rather secrete multiple copies of phage that display a particular insert. Phage that bind to a target molecule can be eluted from the target organ, tissue or cell type and then amplified by growing them in host bacteria. If desired, the amplified phage can be administered to a host and samples of organs, tissues or cell types again collected. Multiple rounds of biopanning can be performed until a population of selective binders is obtained. The amino acid sequence of the peptides is determined by sequencing the DNA corresponding to the targeting peptide insert in the phage genome. The identified targeting peptide can then be produced as a synthetic peptide by standard protein chemistry techniques (Arap et al., 1998, Smith and Scott, 1985). This approach allows circulating targeting peptides to be detected in an unbiased functional assay, without any preconceived notions about the nature of their target. Once a candidate target is identified as the receptor of a targeting peptide, it can be isolated, purified and cloned by using standard biochemical methods (Pasqualini, 1999; Rajotte and Ruoslahti, 1999).

In certain embodiments, a subtraction protocol is used to further reduce background phage binding. The purpose of subtraction is to remove phage from the library that bind to cells other than the cell of interest, or that bind to inactivated cells. In alternative embodiments, the phage library may be prescreened against a subject who does not possess the targeted cell, tissue or organ. For example, placenta-binding peptides may be identified after prescreening a library against a male or non-pregnant female subject. After subtraction the library may be screened against the cell, tissue or organ of interest. In another alternative embodiment, an unstimulated, quiescent cell type, tissue or organ may be screened against the library and binding phage removed. The cell line, tissue or organ is then activated, for example by administration of a hormone, growth factor, cytokine or chemokine and the activated cell type, tissue or organ screened against the subtracted phage library. Other methods of subtraction protocols are known and may be used in the practice of the present invention, for example as disclosed in U.S. Pat. Nos. 5,840,841, 5,705,610, 5,670,312 and 5,492,807.

The methods described herein for identification of targeting peptides involve the in vivo administration of phage display libraries. Various methods of phage display and methods for producing diverse populations of peptides are well known in the art. For example, U.S. Pat. Nos. 5,223,409; 5,622,699 and 6,068,829 disclose methods for preparing a phage library. The potential range of applications for this technique is quite broad, and the past decade has seen considerable progress in the construction of phage-displayed peptide libraries and in the development of screening methods in which the libraries are used to isolate peptide ligands. For example, the use of peptide libraries has made it possible to characterize interacting sites and receptor-ligand binding motifs within many proteins, such as antibodies involved in inflammatory reactions or integrins that mediate cellular adherence. This method has also been used to identify novel peptide ligands that serve as leads to the development of peptidomimetic drugs or imaging agents (Arap et al., 1998). In addition to peptides, larger protein domains such as single-chain antibodies can also be displayed on the surface of phage particles (Arap et al., 1998).

Briefly, $10^{10}$ transducing units (TU) of a $CX_3CX_3CX_3C$ (SEQ ID NO:14; C, cysteine; X, any amino acid residue) phage display random library are pre-absorbed on SK-RC-49 parental cells. The pre-cleared $CX_3CX_3CX_3C$ phage library (~$10^{10}$ TU) is added to 106 detached APA-transfected SK-RC-49 cells in binding medium (20 mM HEPES, 2% FCS in DMEM). Cell panning was performed at 4° C. to minimize post-binding events such as receptor-mediated internalization (Giordano et al., 2001). Cells were washed with binding medium and cell bound phage were recovered and amplified by infection of K91Kan E. coli. Serial dilutions were plated on Luria-Bertani (LB) agar plates with tetracycline and kanamycin. The number of TU was determined by bacterial colony counting.

A. Choice of Phage Display System.

In vivo selection studies performed in mice preferentially employ libraries of random peptides expressed as fusion proteins with the gene III capsule protein in the fUSE5 vector (Pasqualini and Ruoslahti, 1996). The number and diversity of individual clones present in a given library is a significant factor for the success of in vivo selection. It is preferred to use primary libraries, which are less likely to have an over-representation of defective phage clones (Koivunen et al., 1999b). The preparation of a library should be optimized to between $10^8$-$10^9$ transducing units (TU)/ml. In certain embodiments, a bulk amplification strategy is applied between each round of selection.

Phage libraries displaying linear, cyclic, or double cyclic peptides may be used within the scope of the present invention. However, phage libraries displaying 3 to 10 random residues in a cyclic insert ($CX_3$-10C) are preferred, since single cyclic peptides tend to have a higher affinity for the target organ than linear peptides. Libraries displaying double-cyclic peptides (such as $CX_3CX_3CX_3C$; SEQ ID NO:014; Rojotte et al., 1998) may also be used. However, the production of the cognate synthetic peptides, although possible, can be complex due to the multiple conformers with different disulfide bridge arrangements. APA targeting peptides typically will bind APA, subsequent to binding the APA and targeting moiety are internalized by endocytosis.

B. Identification of Homing Peptides and Receptors by In Vivo Phage Display in Mice.

In vivo selection of peptides from phage-display peptide libraries administered to mice has been used to identify targeting peptides selective for normal mouse brain, kidney, lung, skin, pancreas, retina, intestine, uterus, prostate, and adrenal gland (Pasqualini and Ruoslahti, 1996; Pasqualini, 1999; Rajotte et al., 1998). These results show that the vascular endothelium of normal organs is sufficiently heterogeneous to allow differential targeting with peptide probes (Pasqualini and Ruoslahti, 1996; Rajotte et al., 1998). A means of identifying peptides that home to the angiogenic vasculature of tumors has been devised, as described below. A panel of peptide motifs that target the blood vessels of tumor xenografts in nude mice has been assembled (Arap et al., 1998; reviewed in Pasqualini, 1999). These motifs include the sequences RGD-4C, NGR, and GSL. The RGD-4C peptide has previously been identified as selectively binding αv integrins and has been shown to home to the vasculature of tumor xenografts in nude mice (Arap et al., 1998; Pasqualini et al., 1997).

The receptors for the tumor homing RGD4C targeting peptide has been identified as αv integrins (Pasqualini et al., 1997). The αv integrins play an important role in angiogenesis. The αvβ3 and αvβ5 integrins are absent or expressed at low levels in normal endothelial cells but are induced in angiogenic vasculature of tumors (Brooks et al., 1994; Hammes et al., 1996.). Aminopeptidase N/CD13 has recently been identified as an angiogenic receptor for the NGR motif (Burg et al., 1999). Aminopeptidase N/CD13 is strongly expressed not only in the angiogenic blood vessels of prostate cancer in TRAMP mice but also in the normal epithelial prostate tissue.

Tumor-homing phage co-localize with their receptors in the angiogenic vasculature of tumors but not in non-angiogenic blood vessels in normal tissues (Arap et al., 1998). Immunohistochemical evidence shows that vascular targeting phage bind to human tumor blood vessels in tissue sections (Pasqualini et al., 2000) but not to normal blood vessels. A negative control phage with no insert (fd phage) did not bind to normal or tumor tissue sections. The expression of the angiogenic receptors was evaluated in cell lines, in non-proliferating blood vessels and in activated blood vessels of tumors and other angiogenic tissues such as corpus luteum. Flow cytometry and immunohistochemistry showed that these receptors are expressed in a number of tumor cells and in activated HUVECs. The angiogenic receptors were not detected in the vasculature of normal organs of mouse or human tissues.

The distribution of these receptors was analyzed by immunohistochemistry in tumor cells, tumor vasculature, and normal vasculature. Alpha v integrins, CD13, aminopeptidase A, NG2, and MMP-2/MMP-9 (the known receptors in tumor blood vessels) are specifically expressed in angiogenic endothelial cells and pericytes of both human and murine origin. Angiogenic neovasculature expresses markers that are either expressed at very low levels or not at all in non-proliferating endothelial cells.

The markers of angiogenic endothelium include receptors for vascular growth factors, such as specific subtypes of VEGF and basic FGF receptors, and αv integrins, among many others (Mustonen and Alitalo, 1995). Thus far, identification and isolation of novel molecules characteristic of angiogenic vasculature has been slow, mainly because endothelial cells undergo dramatic phenotypic changes when grown in culture (Watson et al., 1995).

Many of these tumor vascular markers are proteases and some of the markers also serve as viral receptors. Alpha v integrins are receptors for adenoviruses (Wickham et al., 1997c) and CD13 is a receptor for coronaviruses (Look et al., 1989). MMP-2 and MMP-9 are receptors for echoviruses (Koivunen et al., 1999a). Aminopeptidase A also appears to be a viral receptor. Bacteriophage may use the same cellular receptors as eukaryotic viruses. These findings suggest that receptors isolated by in vivo phage display will have cell internalization capability, a key feature for utilizing the identified peptide motifs as targeted gene therapy carriers.

Biopanning and Rapid Analysis of Selective Interactive Ligands (BRASIL)

In preferred embodiments, separation of phage bound to the cells of a target organ, tissue or cell type from unbound phage is achieved using the BRASIL technique (PCT Patent Application PCT/US01/28124 by Arap et al., filed Sep. 7, 2001, incorporated herein by reference in its entirety). In BRASIL (Biopanning and Rapid Analysis of Soluble Interactive Ligands), an organ, tissue or cell type is gently separated into cells or small clumps of cells that are suspended in an aqueous phase. The aqueous phase is layered over an organic phase of appropriate density and centrifuged. Cells attached to bound phage are pelleted at the bottom of the centrifuge tube, while unbound phage remain in the aqueous phase. This allows a more efficient separation of bound from unbound phage, while maintaining the binding interaction between phage and cell. BRASIL may be performed in an in vivo protocol, in which organs, tissues or cell types are exposed to a phage display library by intravenous administration, or by an ex vivo protocol, where the cells are exposed to the phage library in the aqueous phase before centrifugation.

C. Preparation of Large Scale Primary Libraries

In certain embodiments, primary phage libraries are amplified before injection into a subject. A phage library is prepared by ligating targeting peptide-encoding sequences into a phage vector, such as fUSE5. The vector is transformed into pilus negative host *E. coli* such as strain MC1061. The bacteria are grown overnight and then aliquots are frozen to provide stock for library production. Use of pilus negative bacteria avoids the bias in libraries that arises from differential infection of pilus positive bacteria by different targeting peptide sequences.

Bacteria may be pelleted from two thirds of a primary library culture (5 liters) at 4000×g for 10 min. Bacteria are resuspended and washed twice with 500 ml of 10% glycerol in water, then frozen in an ethanol/dry ice bath and stored at −80° C.

For amplification, 1.5 ml of frozen bacteria are inoculated into 5 liters of LB medium with 20 μg/ml tetracycline and grown overnight. Thirty minutes after inoculation, a serial dilution is plated on LB/tet plates to verify the viability of the culture. If the number of viable bacteria is less than 5-10 times the number of individual clones in the library ($1-2 \times 10^8$) the culture is discarded.

After growing the bacterial culture overnight, phage are precipitated. About ¼ to ⅓ of the bacterial culture is kept growing overnight in 5 liters of fresh medium and the cycle is repeated up to 5 times. Phage are pooled from all cycles and used for injection into subjects.

Human Subjects

The methods used for phage display biopanning in the mouse model system require substantial improvements for use with humans. Techniques for biopanning in human subjects are disclosed in PCT Patent Application PCT/US01/28044, filed Sep. 7, 2001, the entire text of which is incorporated herein by reference. In general, humans suitable for use with phage display are either brain dead or terminal wean patients. The amount of phage library (preferably primary library) required for administration must be significantly increased, preferably to $10^{14}$ TU or higher, preferably administered intravenously in approximately 200 ml of Ringer lactate solution over about a 10 minute period.

The amount of phage required for use in humans has required substantial improvement of the mouse protocol, increasing the amount of phage available for injection by five orders of magnitude. To produce such large phage libraries, the transformed bacterial pellets recovered from up to 500 to 1000 transformations are amplified up to 10 times in the bacterial host, recovering the phage from each round of amplification and adding LB Tet medium to the bacterial pellet for collection of additional phage. The phage inserts remain stable under these conditions and phage may be pooled to form the large phage display library required for humans.

Samples of various organs and tissues are collected starting approximately 15 minutes after injection of the phage library. Samples are processed as described below and phage collected from each organ, tissue or cell type of interest for DNA sequencing to determine the amino acid sequences of targeting peptides.

With humans, the opportunities for enrichment by multiple rounds of biopanning are severely restricted, compared to the mouse model system. A substantial improvement in the biopanning technique involves polyorgan targeting.

D. Polyorgan Targeting

In the standard protocol for phage display biopanning, phage from a single organ are collected, amplified and injected into a new host, where tissue from the same organ is collected for phage rescue and a new round of biopanning. This protocol is feasible in animal subjects. However, the limited availability and expense of processing samples from humans requires an improvement in the protocol.

It is possible to pool phage collected from multiple organs after a first round of biopanning and inject the pooled sample into a new subject, where each of the multiple organs may be collected again for phage rescue. The polyorgan targeting protocol may be repeated for as many rounds of biopanning as desired. In this manner, it is possible to significantly reduce the number of subjects required for isolation of targeting peptides for multiple organs, while still achieving substantial enrichment of the organ-homing phage.

In preferred embodiments, phage are recovered from human organs, tissues or cell types after injection of a phage display library into a human subject. In certain embodiments, phage may be recovered by exposing a sample of the organ, tissue or cell type to a pilus positive bacterium, such as *E. coli* K91. In alternative embodiments, phage may be recovered by amplifying the phage inserts, ligating the inserts to phage DNA and producing new phage from the ligated DNA.

III. PROTEINS AND PEPTIDES

In certain embodiments, the present invention concerns novel compositions comprising at least one protein or peptide. As used herein, a protein or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide" and "peptide" are used interchangeably herein.

In certain embodiments the size of at least one protein or peptide may comprise, but is not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater amino acid residues.

As used herein, an "amino acid residue" refers to any naturally occurring amino acid, any amino acid derivative or any amino acid mimic known in the art. In certain embodiments, the residues of the protein or peptide are sequential, without any non-amino acid interrupting the sequence of amino acid residues. In other embodiments, the sequence may comprise one or more non-amino acid moiety. In particular embodiments, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid, including but not limited to Aad, 2-Aminoadipic acid; EtAsn, N-Ethylasparagine; Baad, 3-Aminoadipic acid, Hyl, Hydroxylysine; Bala, β-alanine, β-Amino-propionic acid; AHyl, allo-Hydroxylysine; Abu, 2-Aminobutyric acid; 3Hyp, 3-Hydroxyproline; 4Abu, 4-Aminobutyric acid, piperidinic acid; 4Hyp, 4-Hydroxyproline; Acp, 6-Aminocaproic acid, Ide, Isodesmosine; Ahe, 2-Aminoheptanoic acid; AIle, allo-Isoleucine; Aib, 2-Aminoisobutyric acid; MeGly, N-Methylglycine, sarcosine; Baib, 3-Aminoisobutyric acid; MeIle, N-Methylisoleucine; Apm, 2-Aminopimelic acid; MeLys, 6-N-Methyllysine; Dbu, 2,4-Diaminobutyric acid; MeVal, N-Methylvaline; Des, Desmosine; Nva, Norvaline; Dpm, 2,2'-Diaminopimelic acid; Nle, Norleucine; Dpr, 2,3-Diaminopropionic acid; Orn, Ornithine; and EtGly, N-Ethylglycine.

Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed, and may be found at computerized databases known to those of ordinary skill in the art. One such database is the National Center for Biotechnology Information's Genbank and GenPept databases (world wide web at ncbi.nlm.nih.gov). The coding regions for known genes may be amplified and/or expressed using the techniques disclosed herein or as would be know to those of ordinary skill in the art. Alternatively, various commercial preparations of proteins, polypeptides and peptides are known to those of skill in the art.

A. Peptide Mimetics

Another embodiment for the preparation of polypeptides is the use of peptide mimetics. Mimetics are peptide-containing molecules that mimic elements of protein secondary structure. See, for example, Johnson et al., 1993, incorporated herein by reference. The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used to engineer second generation molecules having many of the natural properties of the targeting peptides disclosed herein, but with altered and even improved characteristics.

B. Fusion Proteins

Other embodiments concern fusion proteins. These molecules generally have all or a substantial portion of a targeting peptide (e.g., an APA targeting peptide), linked at the N- or C-terminus, to all or a portion of a second polypeptide or protein. For example, fusions may employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions. In preferred embodiments, the fusion proteins of the instant invention comprise an APA targeting peptide linked to a therapeutic protein or peptide. Examples of proteins or peptides that may be incorporated into a fusion protein include cytostatic proteins, cytocidal proteins, pro-apoptosis agents, anti-angiogenic agents, hormones, cytokines, growth factors, peptide drugs, antibodies, Fab fragments antibodies, antigens, receptor proteins, enzymes, lectins, WIC proteins, cell adhesion proteins and binding proteins. These examples are not meant to be limiting and it is contemplated that within the scope of the present invention virtually any protein or peptide could be incorporated into a fusion protein comprising a targeting peptide. Methods of generating fusion proteins are well known to those of skill in the art. Such proteins can be produced, for example, by chemical attachment using bifunctional cross-linking reagents, by de novo synthesis of the complete fusion protein, or by attachment of a DNA sequence encoding the targeting peptide to a DNA sequence encoding the second peptide or protein, followed by expression of the intact fusion protein.

C. Protein Purification

In certain embodiments a protein or peptide may be isolated or purified. Protein purification techniques are well known to those of skill in the art. These techniques involve, at one level, the homogenization and crude fractionation of the cells, tissue or organ to polypeptide and non-polypeptide fractions. The protein or polypeptide of interest may be further purified using chromatographic and electrophoretic techniques to achieve partial or complete purification (or purification to homogeneity). Analytical methods particularly suited to the preparation of a pure peptide are ion-exchange chromatography, gel exclusion chromatography, polyacrylamide gel electrophoresis, affinity chromatography, immunoaffinity chromatography and isoelectric focusing. An example of receptor protein purification by affinity chromatography is disclosed in U.S. Pat. No. 5,206,347, the entire text of which is incorporated herein by reference. A particularly efficient method of purifying peptides is fast performance liquid chromatography (FPLC) or even high performance liquid chromatography (HPLC).

A purified protein or peptide is intended to refer to a composition, isolatable from other components, wherein the protein or peptide is purified to any degree relative to its naturally-obtainable state. An isolated or purified protein or peptide, therefore, also refers to a protein or peptide free from the environment in which it may naturally occur. Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, or more of the proteins in the composition.

Various methods for quantifying the degree of purification of the protein or peptide are known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity therein, assessed by a "-fold purification number." The actual units used to represent the amount of activity will, of course, be dependent upon the particular assay technique chosen to follow the purification, and whether or not the expressed protein or peptide exhibits a detectable activity.

Various techniques suitable for use in protein purification are well known to those of skill in the art. These include, for example, precipitation with ammonium sulphate, PEG, antibodies and the like, or by heat denaturation, followed by: centrifugation; chromatography steps such as ion exchange, gel filtration, reverse phase, hydroxylapatite and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand.

D. Synthetic Peptides

Because of their relatively small size, the targeting peptides of the invention can be synthesized in solution or on a solid support in accordance with conventional techniques. Various automatic synthesizers are commercially available and can be used in accordance with known protocols. See, for example, Stewart and Young, 1984; Tam et al., 1983; Merrifield, 1986; Barany and Merrifield, 1979, each incorporated herein by reference. Short peptide sequences, usually from about 6 up to about 35 to 50 amino acids, can be readily synthesized by such methods. Alternatively, recombinant DNA technology may be employed wherein a nucleotide sequence which encodes a peptide of the invention is inserted into an expression vector, transformed or transfected into an appropriate host cell, and cultivated under conditions suitable for expression.

E. Antibodies

In certain embodiments, it may be desirable to make antibodies against APA, APA targeting peptides or antibody idiotopes. The appropriate targeting peptide, APA protein or portions thereof, may be coupled, bonded, bound, conjugated, or chemically-linked to one or more agents via linkers, polylinkers, or derivatized amino acids. This may be performed such that a bispecific or multivalent composition or vaccine is produced. It is further envisioned that the methods used in the preparation of these compositions are familiar to those of skill in the art and may be suitable for administration to humans, i.e., pharmaceutically acceptable. Preferred agents are the carriers are keyhole limpet hemocyanin (KLH) or bovine serum albumin (BSA).

Antibodies can be used to therapeutically or diagnostically by inhibiting APA, targeting APA, or detecting APA. These antibodies may be used in various diagnostic or therapeutic applications, described herein below.

As used herein, the term "antibody" is intended to refer broadly to any immunologic binding agent such as IgG, IgM, IgA, IgD and IgE or antibody like molecule. Generally, IgG and/or IgM are preferred because they are the most common antibodies in the physiological situation and because they are most easily made in a laboratory setting. Means for preparing and characterizing antibodies are also well known in the art (See, e.g., Harlow and Lane, 1988; incorporated herein by reference).

Monoclonal antibodies (MAbs) are recognized to have certain advantages (e.g., reproducibility and large-scale production). The invention thus provides for monoclonal antibodies of the human, murine, monkey, rat, hamster, rabbit and even chicken origin. Due to the ease of preparation and ready availability of reagents, murine monoclonal antibodies may be preferred. However, "humanized" antibodies are also contemplated, as are chimeric antibodies from mouse, rat, or other species, bearing human constant and/or variable region domains, bispecific antibodies, recombinant and engineered antibodies and fragments thereof.

The methods for generating monoclonal antibodies (MAbs) and polyclonal antibodies are well known in the art. MAbs may be readily prepared through use of well-known techniques, such as those exemplified in U.S. Pat. No. 4,196, 265, incorporated herein by reference. It is also contemplated that a molecular cloning approach may be used to generate monoclonals. Alternatively, monoclonal antibody fragments encompassed by the present invention can be synthesized using an automated peptide synthesizer, or by expression of full-length gene or of gene fragments in E. coli.

In certain embodiments, compositions comprising a mixture of 2, 3, 4, 5, 6, or more antibodies may be used to treat various pathologic conditions associated with angiogenesis. The antibodies may be polyclonal or monoclonal antibodies selected for either binding of APA, inhibition of APA, or both. These antibodies may also be conjugated to various therapeutic or diagnostic agents.

F. Antibody Conjugates

Certain embodiments of the invention provide antibodies to APA peptides, proteins, polypeptides or antibody idiotypes thereof that are linked to at least one agent to form an antibody conjugate. In order to increase the efficacy of antibody molecules as diagnostic or therapeutic agents, it is conventional to link or covalently bind or complex at least one desired molecule or moiety. A reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired. An example of such a detectable label is gold nanoparticles. Another such example is the formation of a conjugate comprising an antibody linked to a cytotoxic or anti-cellular agent, and may be termed "immunotoxins".

Antibody refers to any antibody-like molecule that has an antigen binding region, and includes antibody fragments such as Fab', Fab, F(ab)$_2$, single domain antibodies (DABs), Fv, scFv (single chain Fv), and the like. Means for preparing and characterizing antibodies are also well known in the art (See, e.g., Harlow and Lane, 1988; incorporated herein by reference).

IV. THERAPEUTIC OR DIAGNOSTIC CONJUGATES

Targeting moieties identified using these methods may be coupled or attached to various substances, including therapeutic or diagnostic agents, for the selective delivery of the conjugate to a desired organ, tissue or cell type in the mouse model system. For example, targeted delivery of chemotherapeutic agents and proapoptotic peptides to receptors located in tumor angiogenic vasculature result in a marked increase in therapeutic efficacy and a decrease in systemic toxicity in tumor bearing mouse models (Arap et al., 1998; Ellerby et al., 1999).

Embodiments of the invention are directed to the treatment of neo-vascularization associated with various disease states. In particular, tumor vasculature. In addition to tumor growth, angiogenesis is important in other diseases. Uncontrolled angiogenesis contributes to the progression of rheumatoid arthritis, diabetic retinopathy, endometriosis, and psoriasis. Growth of blood vessels results in the formation of hemangiomas and arteriovenous malformations that cause a variety of clinical problems ranging from cosmetic complications to life-threatening hemorrhages. Further embodiments of the invention are directed to treatment of these exemplary disease states as well as other associated with neo-vascularization.

Alternatively, the upregulation of APA or the targeting of angiogenesis promoting compounds or substances may be used to promote angiogenesis. Upregulation of APA may be accomplished by delivery of an APA transgene, which in turn may be delivered by various gene therapy vectors known to those of skill in the art.

In further embodiments, a significant homology exist between the APA targeting peptides and the influenza neuraminidase protein. In the case of viral infectious diseases, antibodies can be utilized as immunomodulatory agents include those that are immunospecific for a peptides that bind APA. As used herein, the term "viral antigen" includes, but is not limited to, APA targeting peptides of the invention that are capable of eliciting an immune response or blocking or inhibiting influenza. Antibodies useful in this invention for treatment of a viral infectious disease include, but are not limited to, antibodies against APA targeting peptides with a significant homology to the influenza neuroaminidase protein.

A. Cytokines and Chemokines

In certain embodiments, it may be desirable to couple specific bioactive agents to one or more targeting moieties for targeted delivery to an organ, tissue or cell type. Such agents include, but are not limited to, cytokines, chemokines, pro-apoptosis factors and anti-angiogenic factors. The term "cytokine" is a generic term for proteins released by one cell population that act on another cell as intercellular mediators.

Examples of such cytokines are lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-.alpha. and -.beta.; mullerian-inhibiting substance; mouse gonadotropin-associated peptide; inhibin; activin; vascular endothelial growth factor; integrin; thrombopoietin (TPO); nerve growth factors such as NGF-.beta.; platelet-growth factor; transforming growth factors (TGFs) such as TGF-.alpha. and TGF-.beta.; insulin-like growth factor-I and -II; erythropoietin (EPO); osteoinductive factors; interferons such as interferon-$\alpha$, -.$\beta$, and -$\gamma$; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1.alpha., IL-2, IL-3, IL-4, IL-5, IL-6, IL-7, IL-8, IL-9, IL-10, IL-11, IL-12; IL-13, IL-14, IL-15, IL-16, IL-17, IL-18, LIF, G-CSF, GM-CSF, M-CSF, EPO, kit-ligand or FLT-3, angiostatin, thrombospondin, endostatin, tumor necrosis factor and LT. As used herein, the term cytokine includes proteins from natural sources or from recombinant cell culture and biologically active equivalents of the native sequence cytokines.

Chemokines generally act as chemoattractants to recruit immune effector cells to the site of chemokine expression. It may be advantageous to express a particular chemokine gene in combination with, for example, a cytokine gene, to enhance the recruitment of other immune system components to the site of treatment. Chemokines include, but are not limited to, RANTES, MCAF, MIP1-alpha, MIP1-Beta, and IP-10. The skilled artisan will recognize that certain cytokines are also known to have chemoattractant effects and could also be classified under the term chemokines.

B. Imaging Agents and Radioisotopes

In certain embodiments, the targeting moieties of the present invention may be attached to imaging agents of use for imaging and diagnosis of various diseased organs, tissues or cell types. Many appropriate imaging agents are known in the art, as are methods for their attachment to proteins or peptides (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the protein or peptide (U.S. Pat. No. 4,472,509). Proteins or peptides also may be reacted with an enzyme in the presence of a coupling agent such as glutaraldehyde or periodate. Conjugates with fluorescein markers are prepared in the presence of these coupling agents or by reaction with an isothiocyanate.

Non-limiting examples of paramagnetic ions of potential use as imaging agents include chromium (III), manganese (II), iron (III), iron (II), cobalt (II), nickel (II), copper (II), neodymium (III), samarium (III), ytterbium (III), gadolinium (III), vanadium (II), terbium (H), dysprosium (III), holmium (III) and erbium with gadolinium being particularly preferred. Ions useful in other contexts, such as X-ray imaging, include but are not limited to lanthanum (III), gold (III), lead (II), and especially bismuth (III).

Radioisotopes of potential use as imaging or therapeutic agents include astatine$^{211}$, $^{14}$-carbon, $^{51}$chromium, $^{36}$-chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and yttrium$^{90}$. $^{125}$I is often being preferred for use in certain embodiments, and technicium$^{99m}$ and indium$^{111}$ are also often preferred due to their low energy and suitability for long range detection.

Radioactively labeled proteins or peptides of the present invention may be produced according to well-known methods in the art. For instance, they can be iodinated by contact with sodium or potassium iodide and a chemical oxidizing agent such as sodium hypochlorite, or an enzymatic oxidizing agent, such as lactoperoxidase. Proteins or peptides according to the invention may be labeled with technetium-$^{99m}$ by ligand exchange process, for example, by reducing pertechnate with stannous solution, chelating the reduced technetium onto a Sephadex column and applying the peptide to this column or by direct labeling techniques, e.g., by incubating pertechnate, a reducing agent such as SNCl$_2$, a buffer solution such as sodium-potassium phthalate solution, and the peptide. Intermediary functional groups that are often used to bind radioisotopes that exist as metallic ions to peptides are diethylenetriaminepenta-acetic acid (DTPA) and ethylene diaminetetra-acetic acid (EDTA). Also contemplated for use are fluorescent labels, including rhodamine, fluorescein isothiocyanate and renographin.

In certain embodiments, the claimed proteins or peptides may be linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art in light and is described, for example, in U.S. Pat. Nos. 3,817,837; 3,850,752; 3,939,350; 3,996,345; 4,277,437; 4,275,149 and 4,366,241; each incorporated herein by reference.

In still further embodiments, a targeting moiety may be operatively coupled to a nanoparticle. Nanoparticles include, but are not limited to colloidal gold and silver nanoparticles. Metal nanoparticles exhibit colors in the visible spectral region. It is believed that these colors are the result of excitation of surface plasmon resonances in the metal particles and are extremely sensitive to particles' sizes, shapes, and aggregation state; dielectric properties of the surrounding medium; adsorption of ions on the surface of the particles (For examples see U.S. Patent Application 20040023415, which is incorporated herein by reference).

C. Cross-Linkers

Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, sulthydryl, guanidino, indole, carboxyl specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

Exemplary methods for cross-linking ligands to liposomes are described in U.S. Pat. Nos. 5,603,872 and 5,401,511, each specifically incorporated herein by reference in its entirety. Various ligands can be covalently bound to liposomal surfaces through the cross-linking of amine residues. Liposomes, in particular, multilamellar vesicles (MLV) or unilamellar vesicles such as microemulsified liposomes (MEL) and large lamellar liposomes (LUVET), each containing phosphatidylethanolamine (PE), have been prepared by established procedures. The inclusion of PE in the liposome provides an active functional residue, a primary amine, on the liposomal surface for cross-linking purposes. Ligands such as epidermal growth factor (EGF) have been successfully linked with PE-liposomes. Ligands are bound covalently to discrete sites on the liposome surfaces. The number and surface density of these sites are dictated by the liposome formulation and the liposome type. The liposomal surfaces may also have sites for non-covalent association. To form covalent conjugates of ligands and liposomes, cross-linking reagents have been studied for effectiveness and biocompatibility. Cross-linking reagents include glutaraldehyde (GAD), bifunctional oxirane (OXR), ethylene glycol diglycidyl ether (EGDE), and a water soluble carbodiimide, preferably 1-ethyl-3-(3-dimethylaminopropyl) carbodiimide (EDC). Through the complex chemistry of cross-linking, linkage of the amine residues of the recognizing substance and liposomes is established.

In another example, heterobifunctional cross-linking reagents and methods of using the cross-linking reagents are described (U.S. Pat. No. 5,889,155, specifically incorporated herein by reference in its entirety). The cross-linking reagents combine a nucleophilic hydrazide residue with an electrophilic maleimide residue, allowing coupling in one example, of aldehydes to free thiols. The cross-linking reagent can be modified to cross-link various functional groups.

V. NUCLEIC ACIDS

Nucleic acids according to the present invention may encode a targeting peptide, a targeting antibody, a therapeutic polypeptide a fusion protein or other protein or peptide. The nucleic acid may be derived from genomic DNA, complementary DNA (cDNA) or synthetic DNA.

A "nucleic acid" as used herein includes single-stranded and double-stranded molecules, as well as DNA, RNA, chemically modified nucleic acids and nucleic acid analogs. It is contemplated that a nucleic acid within the scope of the present invention may be of almost any size, determined in part by the length of the encoded protein or peptide.

It is contemplated that targeting peptides, targeting antibodies, and fusion proteins may be encoded by any nucleic acid sequence that encodes the appropriate amino acid sequence. The design and production of nucleic acids encoding a desired amino acid sequence is well known to those of skill in the art, using standardized codon tables. In preferred embodiments, the codons selected for encoding each amino acid may be modified to optimize expression of the nucleic acid in the host cell of interest.

A. Targeted Delivery of Gene Therapy Vectors

There are a number of ways in which gene therapy vectors may introduced into cells. In certain embodiments of the invention, the gene therapy vector comprises a virus. The ability of certain viruses to enter cells via receptor-mediated endocytosis, to integrate into host cell genome or be maintained episomally, and express viral genes stably and efficiently have made them attractive candidates for the transfer of foreign genes into mammalian cells (Ridgeway, 1988; Nicolas and Rubinstein, 1988.; Baichwal and Sugden, 1986; Temin, 1986). Preferred gene therapy vectors are generally viral vectors. DNA viruses used as gene therapy vectors include the papovaviruses (e.g., simian virus 40, bovine papilloma virus, and polyoma) (Ridgeway, 1988; Baichwal and Sugden, 1986) and adenoviruses (Ridgeway, 1988; Baichwal and Sugden, 1986).

One of the preferred methods for in vivo delivery involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include, but is not limited to, constructs containing adenovirus sequences sufficient to (a) support packaging of the construct and (b) to express an antisense or a sense polynucleotide that has been cloned therein.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic innoculation into the brain (Le Gal La Salle et al., 1993).

In preferred embodiments, certain advantages may be gained from coupling therapeutic molecules or substances to targeting moieties, e.g., APA targeting moieties, that target the vasculature of diseased tissues, e.g., tumors or neo-vascular beds. Specifically, moieties that home to tumor vasculature have been coupled to cytotoxic drugs or proapoptotic peptides to yield compounds were more effective and less toxic than the parental compounds in experimental models of mice bearing tumor xenografts (Arap et al., 1998; Ellerby et al, 1999). The insertion of the RGD-4C peptide into a surface protein of an adenovirus has produced an adenoviral vector that may be used for tumor targeted gene therapy (Arap et al., 1998).

A "fiber protein" according to the invention preferably comprises an adenoviral fiber protein. Any one of the serotypes of human or nonhuman adenovirus (e.g., a chimeric fiber protein) can be used as the source of the fiber protein or fiber gene. Optimally, however, the adenovirus is an Ad2 or Ad5 adenovirus. (see, U.S. Pat. No. 6,649,407, which is incorporated herein by reference in its entirety).

The fiber protein is "chimeric" in that it comprises amino acid residues that are not typically found in the protein as isolated from wild-type adenovirus (i.e., comprising the native protein, or wild-type protein). The fiber protein thus comprises a "normative amino acid sequence". "Normative amino acid sequence" means a sequence of any suitable length, preferably from about 3 to about 200 amino acids, optimally from about 3 to about 30 amino acids. Desirably, the normative amino acid sequence is introduced into the fiber protein at the level of gene expression (i.e., by introduction of a "nucleic acid sequence that encodes a normative amino acid sequence"). Such a normative amino acid sequence either is introduced in place of adenoviral sequences, or in addition to adenoviral sequences. Regardless of the nature of the introduction, its integration into an adenoviral fiber protein at the level of either DNA or protein, results in the generation of a peptide motif (i.e., a peptide binding motif) in the resultant chimeric fiber protein.

The peptide motif allows for cell targeting, for instance, by comprising a targeting moiety of the invention, and/or a ligand for a cell surface binding site. The peptide motif optionally can comprise other elements of use in cell targeting (e.g., a single-chain antibody sequence). The peptide binding motif may be generated by the insertion, and may comprise, for instance, native and normative sequences, or may be entirely made up of normative sequences. The peptide motif that results from the insertion of the normative amino acid sequence into the chimeric fiber protein can be either a high affinity peptide (i.e., one that binds its cognate binding site, e.g., APA, when provided at a relatively low concentration) or a low affinity peptide (i.e., one that binds its cognate binding site, e.g., APA, when provided at a relatively high concentration). Preferably, however, the resultant peptide motif is a high affinity motif, particularly one that has a high affinity for its cognate binding site due to its constraint within the adenovirus fiber protein.

Other gene transfer vectors may be constructed from retroviruses. (Coffin, 1990.) In order to construct a retroviral vector, a nucleic acid encoding protein of interest is inserted into the viral genome in the place of certain viral sequences to produce a virus that is replication-defective. In order to produce virions, a packaging cell line containing the gag, pol, and env genes, but without the LTR and packaging components, is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are capable of infecting a broad variety of cell types. However, integration and stable expression require the division of host cells (Paskind et al., 1975).

Other viral vectors may be employed as targeted gene therapy vectors. Vectors derived from viruses such as vaccinia virus (Ridgeway, 1988; Baichwal and Sugden, 1986; Coupar et al., 1988), adeno-associated virus (AAV) (Ridgeway, 1988; Baichwal and Sugden, 1986; Hermonat and Muzycska, 1984), and herpes viruses may be employed.

In a further embodiment of the invention, gene therapy construct may be entrapped in a liposome. Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa, and hepatoma cells. Nicolau et al., (1987.) accomplished successful liposome-mediated gene transfer in rats after intravenous injection.

Gene therapy vectors of the invention may comprise various transgenes, which are typically encoded DNA or RNA of an expression vector. Gene therapy may be used for the expression of a therapeutic gene, expression of APA to enhance neo-vascularization or for the inhibition of APA expression for the treatment of disease states associated with neo-vascularization. DNA may be in form of cDNA, in vitro polymerized DNA, plasmid DNA, parts of a plasmid DNA, genetic material derived from a virus, linear DNA, vectors (P1, PAC, BAC, YAC, artificial chromosomes), expression cassettes, chimeric sequences, recombinant DNA, chromosomal DNA, an oligonucleotide, anti-sense DNA, or derivatives of these groups. RNA may be in the form of oligonucleotide RNA, tRNA (transfer RNA), snRNA (small nuclear RNA), rRNA (ribosomal RNA), mRNA (messenger RNA), in vitro polymerized RNA, recombinant RNA, chimeric sequences, anti-sense RNA, siRNA (small interfering RNA), ribozymes, or derivatives of these groups. An anti-sense polynucleotide is a polynucleotide that interferes with the function of DNA and/or RNA. Antisense polynucleotides include, but are not limited to: morpholinos, 2'-O-methyl polynucleotides, DNA, RNA and the like. SiRNA comprises a double stranded structure typically containing 15-50 base pairs and preferably 21-25 base pairs and having a nucleotide sequence identical or nearly identical to an expressed target gene or RNA within the cell. Interference may result in suppression of expression. The polynucleotide can also be a sequence whose presence or expression in a cell alters the expression or function of cellular genes or RNA, e.g., APA. In addition, DNA and RNA may be single, double, triple, or quadruple stranded.

VI. PHARMACEUTICAL COMPOSITIONS

Pharmaceutical compositions of the present invention comprise an effective amount of one or more compositions including a targeting moiety as described herein dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one composition of the present invention (e.g., APA targeting moieties) or an additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The therapeutic and diagnostic compositions of the present invention may comprise different types of carriers depending on whether it is to be administered in solid, liquid or aerosol form, and whether it need to be sterile for such routes of administration. The present invention can be administered intravenously, intradermally, intraarterially, intraperitoneally, intralesionally, intracranially, intraarticularly, intrapleurally, intratracheally, intratumorally, intramuscularly, intraperitoneally, subcutaneously, intravesicularlly, inhalation (e.g. aerosol inhalation), injection, infusion, continuous infusion, localized perfusion bathing target cells directly, via a catheter, via a lavage, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to a subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 μg/kg/body weight, about 5 μg/kg/body weight, about 10 μg/kg/body weight, about 50 μg/kg/body weight, about 100 μg/kg/body weight, about 200 μg/kg/body weight, about 350 μg/kg/body weight, about 500 μg/kg/body weight, about 1 mg/kg/body weight, about 5 mg/kg/body weight, about 10 mg/kg/body weight, about 50 mg/kg/body weight, about 100 mg/kg/body weight, about 200 mg/kg/body weight, about 350 mg/kg/body weight, about 500 mg/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In embodiments where the composition is in a liquid form, a carrier can be a solvent or dispersion medium comprising but not limited to, water, ethanol, polyol (e.g., glycerol, propylene glycol, liquid polyethylene glycol), lipids (e.g., triglycerides, vegetable oils, liposomes) and combinations thereof. In many cases, it will be preferable to include isotonic agents, such as, for example, sugars, sodium chloride or combinations thereof.

Sterile injectable solutions are prepared by incorporating the APA targeting moiety or conjugate thereof in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

VII. THERAPEUTIC AGENTS

In certain embodiments, therapeutic agents may be operatively coupled to a targeting peptide or fusion protein for selective delivery to, for example, tumor vasculature expressing APA. Agents or factors suitable for use may include any chemical compound that induces apoptosis, cell death, cell stasis and/or anti-angiogenesis.

A. Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins that share in common structural and sequence homologies. These different family members have been shown to either possess similar functions to Bcl-2 (e.g., $Bcl_{XL}$, $Bcl_W$, $Bcl_S$, Mcl-1, A1, Bfl-1) or counteract Bcl-2 function and promote cell death (e.g., Bax, Bak, Bik, Bim, Bid, Bad, Harakiri).

B. Angiogenic Inhibitors

In certain embodiments the present invention may concern administration of targeting moieties operatively coupled to anti-angiogenic agents, such as angiotensin, laminin peptides, fibronectin peptides, plasminogen activator inhibitors, tissue metalloproteinase inhibitors, interferons, interleukin 12, platelet factor 4, IP-10, Gro-β, thrombospondin, 2-methoxyoestradiol, proliferin-related protein, carboxiamidotriazole, CM101, Marimastat, pentosan polysulphate, angiopoietin 2 (Regeneron), interferon-alpha, herbimycin A, PNU145156E, 16K prolactin fragment, Linomide, thalidomide, pentoxifylline, genistein, TNP-470, endostatin, paclitaxel, accutin, angiostatin, cidofovir, vincristine, bleomycin, AGM-1470, platelet factor 4 or minocycline.

Proliferation of tumors cells relies heavily on extensive tumor vascularization, which accompanies cancer progression. Thus, inhibition of new blood vessel formation with anti-angiogenic agents and targeted destruction of existing blood vessels have been introduced as an effective and relatively non-toxic approach to tumor treatment. (Arap et al., 1998; Arap et al., 1998; Ellerby et al., 1999). A variety of anti-angiogenic agents and/or blood vessel inhibitors are known. (e.g., Folkman, 1997; Eliceiri and Cheresh, 2001).

C. Cytotoxic Agents

Chemotherapeutic (cytotoxic) agents may be used to treat various disease states, including cancer. Chemotherapeutic (cytotoxic) agents of potential use include, but are not limited to, 5-fluorouracil, bleomycin, busulfan, camptothecin, carboplatin, chlorambucil, cisplatin (CDDP), cyclophosphamide, dactinomycin, daunorubicin, doxorubicin, estrogen receptor binding agents, etoposide (VP16), farnesyl-protein transferase inhibitors, gemcitabine, ifosfamide, mechlorethamine, melphalan, mitomycin, navelbine, nitrosurea, plicomycin, procarbazine, raloxifene, tamoxifen, taxol, temazolomide (an aqueous form of DTIC), transplatinum, vinblastine and methotrexate, vincristine, or any analog or derivative variant of the foregoing. Most chemotherapeutic agents fall into the categories of alkylating agents, antimetabolites, antitumor antibiotics, corticosteroid hormones, mitotic inhibitors, and nitrosoureas, hormone agents, miscellaneous agents, and any analog or derivative variant thereof.

Chemotherapeutic agents and methods of administration, dosages, etc. are well known to those of skill in the art (see for example, the "Physicians Desk Reference", Goodman & Gilman's "The Pharmacological Basis of Therapeutics" and in "Remington's Pharmaceutical Sciences" $15^{th}$ ed., pp 1035-1038 and 1570-1580, incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject. Of course, all dosages and agents described herein are exemplary rather than limiting, and other doses or agents may be used by a skilled artisan for a specific patient or application. Any dosage in-between these points, or range derivable therein is also expected to be of use in the invention.

D. Alkylating Agents

Alkylating agents are drugs that directly interact with genomic DNA to prevent cells from proliferating. This category of chemotherapeutic drugs represents agents that affect all phases of the cell cycle, that is, they are not phase-specific.

An alkylating agent, may include, but is not limited to, a nitrogen mustard, an ethylenimene, a methylmelamine, an alkyl sulfonate, a nitrosourea or a triazines. They include but are not limited to: busulfan, chlorambucil, cisplatin, cyclophosphamide (cytoxan), dacarbazine, ifosfamide, mechlorethamine (mustargen), and melphalan.

E. Antimetabolites

Antimetabolites disrupt DNA and RNA synthesis. Unlike alkylating agents, they specifically influence the cell cycle during S phase. Antimetabolites can be differentiated into various categories, such as folic acid analogs, pyrimidine analogs and purine analogs and related inhibitory compounds. Antimetabolites include but are not limited to, 5-fluorouracil (5-FU), cytarabine (Ara-C), fludarabine, gemcitabine, and methotrexate.

F. Natural Products

Natural products generally refer to compounds originally isolated from a natural source, and identified as having a pharmacological activity. Such compounds, analogs and derivatives thereof may be, isolated from a natural source, chemically synthesized or recombinantly produced by any technique known to those of skill in the art. Natural products include such categories as mitotic inhibitors, antitumor antibiotics, enzymes and biological response modifiers.

Mitotic inhibitors include plant alkaloids and other natural agents that can inhibit either protein synthesis required for cell division or mitosis. They operate during a specific phase during the cell cycle. Mitotic inhibitors include, for example, docetaxel, etoposide (VP16), teniposide, paclitaxel, taxol, vinblastine, vincristine, and vinorelbine.

Taxoids are a class of related compounds isolated from the bark of the ash tree, *Taxus brevifolia*. Taxoids include but are not limited to compounds such as docetaxel and paclitaxel. Paclitaxel binds to tubulin (at a site distinct from that used by the vinca alkaloids) and promotes the assembly of microtubules.

Vinca alkaloids are a type of plant alkaloid identified to have pharmaceutical activity. They include such compounds as vinblastine (VLB) and vincristine.

G. Antibiotics

Certain antibiotics have both antimicrobial and cytotoxic activity. These drugs also interfere with DNA by chemically inhibiting enzymes and mitosis or altering cellular membranes. These agents are not phase specific so they work in all phases of the cell cycle. Examples of cytotoxic antibiotics include, but are not limited to, bleomycin, dactinomycin, daunorubicin, doxorubicin (Adriamycin), plicamycin (mithramycin) and idarubicin.

H. Miscellaneous Agents

Miscellaneous cytotoxic agents that do not fall into the previous categories include, but are not limited to, platinum coordination complexes, anthracenediones, substituted ureas, methyl hydrazine derivatives, amsacrine, L-asparaginase, and tretinoin. Platinum coordination complexes include such compounds as carboplatin and cisplatin (cis-DDP). An exemplary anthracenedione is mitoxantrone. An exemplary substituted urea is hydroxyurea. An exemplary methyl hydrazine derivative is procarbazine (N-methylhydrazine, MIH). These examples are not limiting and it is contemplated that any known cytotoxic, cytostatic or cytocidal agent may be attached to targeting peptides and administered to a targeted organ, tissue or cell type within the scope of the invention.

VIII. SMALL MOLECULE MODULATORS OF APA

In other aspects, the invention includes compositions and methods for identifying APA modulating compounds, such as, but not limited to peptide mimetics or small molecule modulators of APA. Assays are described that can be used to identify compounds that modulate APA. Molecules identified by the methods may be used to modulate APA activity. The modulation of APA may be used, much like the introduction of certain APA targeting moieties, to regulate the activity of APA and angiogenesis.

APA modulating compounds include compounds which interact with APA such that the activity of the APA is modulated, e.g., enhanced or inhibited. In one embodiment, the APA modulating compounds modulate the activity of a APA as measured by assays known in the art.

The term "activity of a APA" includes the ability of a APA to proteolytically process angiotensin II or induce or promote angiogenesis. In one embodiment, the APA modulating compound inhibits a particular APA by about 10% or greater, about 40% or greater, about 50% or greater, about 60% or greater, about 70% or greater, about 80% or greater, about 90% or greater, about 95% or greater, or about 100% as compared to the activity of the APA without the APA modulating compound. Since APA is a protease the inhibition of its protease activity results in the repression of angiotensin II processing. Screening for modulators of APA activity may be done using APA expressing cells or bacteria containing an APA protein.

Test compounds that can be tested in the subject assays include various small molecules, peptides, peptide like molecules, or libraries thereof. The term "test compound" includes any reagent or test agent which is employed in the assays of the invention and assayed for its ability to influence the activity of a APA protein, by for example, binding to the APA polypeptide and/or to a molecule with which it interacts. More than one compound, e.g., a plurality of compounds, can be tested at the same time for their ability to modulate the activity of APA. Exemplary test compounds which can be screened for activity include, but are not limited to, peptides, non-peptidic compounds, nucleic acids, carbohydrates, small organic molecules (e.g., polyketides), and natural product extract libraries. The term "non-peptidic test compound" includes compounds that are comprised, at least in part, of molecular structures different from naturally-occurring L-amino acid residues linked by natural peptide bonds. However, "non-peptidic test compounds" also include compounds composed, in whole or in part, of peptidomimetic structures, such as D-amino acids, non-naturally-occurring L-amino acids, modified peptide backbones and the like, as well as compounds that are composed, in whole or in part, of molecular structures unrelated to naturally-occurring L-amino acid residues linked by natural peptide bonds. "Non-peptidic test compounds" also are intended to include natural products. The term "antagonist" includes APA modulating compounds, which inhibit the activity of APA by binding to and inactivating APA, or by disrupting a critical protein-protein interaction. APA modulators may include, for example, naturally or chemically synthesized compounds such as small cell permeable organic molecules, peptides, and the like.

Nucleic acids encoding APA can be expressed in cells using vectors. Almost any conventional delivery vector can be used. Such vectors are widely available commercially and it is within the knowledge and discretion of one of ordinary skill in the art to choose a vector which is appropriate for use with a given expression system. Alternatively, a cell expressing endogenous APA may be selected. These nucleic acids can be introduced into cells using standard techniques, for example, by transformation using calcium chloride or electroporation. Such techniques for the introduction of DNA into cells are well known in the art.

In one embodiment, the invention provides for methods of identifying a test compound which modulates the activity of a APA protein by contacting a cell expressing a APA protein (or portion thereof) with a test compound under conditions which allow interaction of the test compound with the cell. The ability of the test compound to modulate an activity of APA can be determined in a variety of ways, including the proteolysis of a substrate molecule. Proteolysis detected by western blotting, SDS-Page gel, mass spectrometry or HPLC, for example.

Candidate compounds for testing in the instant methods can be derived from a variety of different sources and can be known or can be novel. In one embodiment, libraries of compounds are tested in the instant methods to identify APA modulating compounds.

A recent trend in medicinal chemistry includes the production of mixtures of compounds, referred to as libraries. While the use of libraries of peptides is well established in the art, new techniques have been developed which have allowed the production of mixtures of other compounds, such as benzodiazepines (Bunin et al., 1992; DeWitt et al., 1993), peptoids (Zuckermann, 1994), oligocarbamates (Cho et al., 1993), and hydantoins (DeWitt et al., 1993). The synthesis of molecular libraries of small organic molecules with a diversity of $10^4$-$10^5$ have been described (Carell et al. 1994).

The compounds of the present invention may be obtained using any of the numerous approaches in combinatorial library methods known in the art, including: biological libraries, spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, 1997).

Exemplary compounds which can be screened for activity include, but are not limited to, peptides, nucleic acids, carbohydrates, small organic molecules, and natural product extract libraries. In one embodiment, the test compound is a peptide or peptidomimetic. In another, preferred embodiment, the compounds are small, organic non-peptidic compounds. Other exemplary methods for the synthesis of molecular libraries can be found in the art, for example in: Erb et al. (1994); Horwell et al. (1996); and in Gallop et al. (1994).

Libraries of compounds may be presented in solution (e.g., Houghten, 1992), or on beads (Lam, 1991), chips (Fodor, 1993), bacteria (Ladner, U.S. Pat. No. 5,223,409), spores (Ladner U.S. Pat. No. '409), plasmids (Cull et al., 1992), or on phage (Scott and Smith, 1990); (Devlin, 1990); (Cwirla et al., 1990); (Felici, (1991). Other types of peptide libraries may also be expressed, see, for example, U.S. Pat. Nos. 5,270,181 and 5,292,646, which are incorporated herein by reference. In still another embodiment, combinatorial polypeptides can be produced from a cDNA library.

In yet another embodiment, computer programs can be used to identify individual compounds or classes of compounds with an increased likelihood of modulating a APA activity. Such programs can screen for compounds with the proper molecular and chemical complementarities with a chosen APA or APA targeting moiety. In this manner, the efficiency of screening for APA modulating compounds in the assays described above can be enhanced.

Computer modeling techniques may be utilized for identifying APA modulating compounds. Molecular design techniques may be used to design APA modulating compounds, which are capable of binding or interacting with one or more APA polypeptides.

In an embodiment, the invention pertains to a method of identifying APA modulating compounds. The method includes obtaining or modeling the structure of APA or a variant thereof, and using GLIDE to identify a scaffold which has an interaction energy score of −20 or less (e.g., −40 or less, e.g., −60 or less) with a portion of APA.

The invention pertains, at least in part, to a computational screening of small molecule databases for chemical entities or compounds that can bind in whole, or in part, to APA. In this screening, the quality of fit of such entities or compounds to the binding site may be judged either by shape complementarity or by estimated interaction energy (Meng et al., 1992). Such a procedure allows for the screening of a very large library of potential APA modulating compounds for the proper molecular and chemical complementarities with a selected protein or class or proteins. APA modulating compounds identified through computational screening can later be passed through in vitro and in vivo assays as further screens.

A variety of crystal structures are available in the Protein Data Bank (world wide web at rcsb.org/pdb/). These structures may be used as model structures to identify sites on the proteins that could be targeted by small molecule chemical inhibiting compounds.

The GLIDE docking method may then be used to fit combinatorial chemistry scaffolds into these sites and an interaction energy was calculated for each. These scaffolds may then be used to search, for example, the CambridgeSoft ACX-SC database of over 600,000 non-proprietary chemical structures and the number of chemicals similar to the scaffolds. The term "scaffold" includes the compounds identified by the computer modeling program. These compounds may or may not be themselves APA modulating compounds. An ordinarily skilled artisan will be able to analyze a scaffold obtained from the computer modeling program and modify the scaffold such that the resulting compounds have enhanced chemical properties over the initial scaffold compound, e.g., are more stable for administration, less toxic, have enhanced affinity for a particular APA. The invention pertains not only to the scaffolds identified, but also the APA modulating compounds which are developed using the scaffolds.

An APA modulating compound or other binding compound may be computationally evaluated and designed by screening and selecting chemical entities or fragments for their ability to associate with the individual small molecule binding sites or other areas of APA or variant thereof.

Specialized computer programs may also assist in the process of selecting molecules that bind to APA. The programs include, but are not limited to GRID (Goodford, 1985); AUTODOCK (Goodsell and Olsen, 1990); MCSS (Miranker and Karplus, 1991); MACCS-3D (Martin, 1992); DOCK (Kuntz et al., 1982); and/or MCDLNG (Monte Carlo De Novo Ligand Generator) (Gehlhaar et al., 1995).

Once suitable chemical fragments have been selected, they can be assembled into a single compound or inhibiting compound. Assembly may be proceed by visual inspection of the relationship of the fragments to each other on a three-dimensional image display on a computer screen in relation to the structure coordinates of a particular APA or APA model. This may be followed by manual model building using software such as Quanta or Sybyl.

Useful programs to aid one of skill in the art in connecting the individual chemical fragments include: 3D Database systems such as MACCS-3D (MDL Information Systems, San Leandro, Calif.; reviewed in Martin (1992); CAVEAT (Bartlett et al., 1989); and/or HOOK (Molecular Simulations, Burlington, Mass.).

In another embodiment, APA modulating compounds may be designed as a whole or "de novo" using either an empty active site or optionally including some portion(s) of a known inhibiting compound(s). These methods include: LUDI (Bohm, 1992); Biosym Technologies, San Diego, Calif.; LEGEND (Nishibata and Itai, 1991); Molecular Simulations, Burlington, Mass.; CoMFA (Conformational Molecular Field Analysis) (Kaminski. 1994); LeapFrog (Tripos Associates, St. Louis, Mo.); and/or FlexX (© 1993-2002 GMD German National Research Center for Information Technology; Rarey et al., 1999). Other molecular modeling techniques may also be employed in accordance with this invention. See, e.g., Cohen et al. (1990) and Navia and Murcko (1992).

Once a compound has been designed and selected by the above methods, the efficiency with which that compound may bind to a particular APA may be tested and optimized by computational evaluation.

Specific computer software is available in the art to evaluate compound deformation energy and electrostatic interaction. Examples of programs designed for such uses include: Gaussian 92, revision C (M. J. Frisch, Gaussian, Inc., Pittsburgh, Pa. 1992); AMBER, version 4.0 (P. A. Kolhnan, University of California at San Francisco, ©1994); QUANTA/CHARMM (Molecular Simulations, Inc., Burlington, Mass. ©1994); and Insight II/Discover (Biosysm Technologies Inc., San Diego, Calif. ©1994). These programs may be implemented, for instance, using a Silicon Graphics workstation, IRIS 4D/35 or IBM RISC/6000 workstation model 550. Other hardware systems and software packages will be known to those skilled in the art.

Once an APA modulating compound has been optimally selected or designed, as described above, substitutions may then be made in some of its atoms or side groups in order to improve or modify its binding properties. Initial substitutions are preferable conservative, i.e., the replacement group will have approximately the same size, shape, hydrophobicity and charge as the original group. Such substituted chemical compounds may then be analyzed for efficiency of fit to APA by the same computer methods described above.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Reagents

VEGF-A165, bFGF, and TGF-α were from R&D Systems (Minneapolis, Minn.) and anti-CD31 antibody from BD-Pharmingen (San Diego, Calif.). RC38 (Schlingemann et al., 1996), ASD-37, ASD-41 (Assmann et al., 1992) and PAL-E antibody (Schlingemann et al., 1985) have been described. Synthetic peptides were purchased from AnaSpec (San Jose, Calif.). Unless otherwise indicated, an unrelated synthetic peptide (sequence GACVRLSACGA SEQ ID NO:7) was used as a negative control. A phage display random peptide library displaying the insert CX3CX3CX3C(C, cysteine; X, any amino acid residue; SEQ ID NO:14) was constructed as described (Smith and Scott, 1993).

Cell Culture

Renal carcinoma cells SK-RC-49 (Ebert et al., 1990) were stably transfected with a mammalian expression vector encoding the full-length APA cDNA (Geng et al., 1998) and HMECs stably transfected with large T (Ades et al., 1992). EF43-fgf4 cells have been described (Deroanne et al., 1997, Hajitou et al., 2001).

Animals

Institutional animal care and utilization committees approved animal experiments. This study adhered to the Association for Research in Vision and Opthalmology (ARVO) guidelines. The APA −/− strain of inbred C57BL/6 mice has been described (Lin et al., 1998). Nude mice and Balb/c mice were obtained from Jackson Laboratory (Bar Harbor, Me.).

Mouse Model of Retinal Neovascularization

P7 mouse pups were exposed to 75% oxygen for 5 days. Mice were returned to room air (20.8% O2) on P12(Smith et al., 1994). For histological analysis mice were sacrificed on P19, eyes were enucleated, fixed, serially sectioned and stained with hematoxylin and eosin (H&E). Endothelial cell nuclei on the vitreous side of the internal limiting membrane were counted. At least 10H&E-stained sections were evaluated per eye, and the average number of nuclei was counted from 4-16 eyes for each condition.

In Vivo Angiogenesis Assay

The inventors used an angiogenesis assay in which gelfoam sponges (Pharmacia & Upjohn, Kalamazoo, Mich.) impregnated with VEGF, bFGF, and TGF-α (200 ng/ml each) are implanted in vivo as described (McCarty et al., 2002). Sponges were implanted into the subcutaneous tissue of homozygous APA +/+ or APA −/− mice. After 14 days, anesthetized mice were perfused with 4% paraformaldehyde (PAF). Sponges were fixed with 4% PAF, frozen and sectioned at 50 μm. Sections were stained with an anti-CD31 antibody and a Cy3-conjugated secondary antibody. Quantification of CD31+ cells was determined (McCarty et al., 2002).

Cell Surface Panning

The inventors pre adsorbed 1010 transducing units (TU) of a CX3CX3CX3C (C, cysteine; X, any amino acid residue; SEQ ID NO:14) phage display random library on SK-RC-49 parental cells. Next, the pre-cleared CX3CX3CX3C (SEQ ID NO:14) phage library (~1010 TU) was added to 106 detached APA-transfected SK-RC-49 cells in binding medium (20 mM HEPES, 2% FCS in DMEM). Cell panning was performed at 4° C. to minimize post-binding events such as receptor-mediated internalization (Giordano et al., 2001). Cells were washed with binding medium and cell bound phage were recovered and amplified by infection of K91 Kan E. coli. Serial dilutions were plated on Luria-Bertani (LB) agar plates with tetracycline and kanamycin. The number of TU was determined by bacterial colony counting.

APA Immunocapture and Enzymatic Assay

Cells lysates were prepared in ice-cold 100 mM N-octyl-β-glucopyranoside in PBS. Microtiter wells were coated with 2 μg of RC38 and blocked with 3% BSA. Cell lysates (1 mg of protein/ml) were incubated on RC38-coated wells overnight at 4° C. Wells were washed with 0.1% Tween-20 in PBS. The assay for APA enzymatic activity with α-L-glutamyl-p-nitroanilide has been described (Lin et al., 1998). Activity was determined by measuring absorbance at 405 nm.

Binding Assays on APA or on APA-Transfected Cells

Binding assays were performed on cells with 109 TU phage input. Increasing concentrations of synthetic CPRECESIC (SEQ ID NO:2) or control peptides were used to evaluate competitive inhibition of phage binding. APA was immunocaptured on microtiter wells with RC38 and incubated with 109 TU of phage in 3% BSA in PBS. Wells were washed with 1% BSA, 0.01% Tween-20 in PBS and phage were recovered by infection of K91kan E. coli. Serial dilutions were plated on LB agar plates containing tetracycline and kanamycin. The number of TU was determined by bacterial colony counting.

Endothelial Cell Growth Assay

HMECs were seeded (~10,000 cells/well) and allowed to attach for 24 hours in complete M199 medium (Sigma; St. Louis, Mo.). The indicated concentrations of CPRECESIC (SEQ ID NO:2) or 1 mM negative control peptide were added to the cells in complete M199 medium. HMECs were then serially fixed in 2.5% glutaraldehyde, stained with 0.1% crystal violet in 20% methanol, and solubilized in 10% acetic acid. Cell growth was evaluated by measuring absorbance at 590 nm. A calibration curve with linear correlation between absorbance and cell number (103-105 HMECs) was used for the assay.

Chemotaxic Assay

Cell migration assays were performed in a 48-well Boyden chamber (NeuroProbe; Gaithersburg, Md.) as described (Bussolino et al., 1995). Indicated concentrations of CPRECESIC (SEQ ID NO:2) peptide or negative control peptide (1 mM) were placed in the lower chamber compartment in complete M199 medium. Subconfluent HMECs were harvested and 1×105 cells were seeded in the upper chamber compartment in complete M199 medium. Cells were allowed to migrate for 5 h at 37° C. in a humidified 5% CO2 atmosphere. Filter was removed and cells on the upper side were scraped off. Migrated cells were fixed and Giemsa-stained.

Three-Dimensional Cell Culture

Matrigel (BD Biosciences; Bedford, Mass.) was added to 48-well tissue culture plates and allowed to solidify at 37° C. HMECs (~104 cells) were added to the wells and allowed to adhere to the Matrigel for 30 minutes at 37° C. Cell medium was replaced containing the indicated concentrations of CPRECESIC (SEQ ID NO:2) or a negative control peptide (both at 1 mM) in complete medium. Plates were examined and photographed after 16 hours.

Chick Embryo Chorioallantoic Membrane (CAM) Assay

Fertilized chicken eggs were incubated in constant humidity at 37° C. for 3 days. Two to three ml of albumin was removed through a square opening to detach the developing CAM. The opening was sealed with a glass plate and the eggs were incubated for 5 days. One mm3 gelfoam sponges were adsorbed with 20 ng of VEGF, or 20 ng of VEGF plus 1 mM CPRECESIC (SEQ ID NO:2) or negative control peptide, and implanted on top of the growing CAMs. CAMs were examined daily until day 12, photographed in ovo with a stereomicroscope and emerging capillaries were counted (Ribatti et al., 1997).

In Situ Enzyme Histochemistry

Biopsy materials were snap-frozen and serially sectioned at 5 μm. Acetone-fixed tissue sections were incubated at 37° C. with 1.6 mM of the APA-specific substrate N-Glutamyl-4-methoxy-3-naphtylamide (Bachem; Bubendorf, Switzerland) and 1.1 mM Fast Blue B salt in 0.1 M Tris (pH 7.0) containing 2.5 mM CaCl2. Tissue sections were fixed, stained with H&E, and examined with a light microscope.

Immunoperoxidase, Immunofluorescence and Immuno-Electron Microscopy

Frozen sections of colon adenocarcinoma metastases to the brain were immunoperoxidase-stained with RC38 antibody by using diaminobenzidine (DAB) as substrate (brown staining product). Tissue sections were washed with 0.1 M Glycine-HCL, pH 3.0, to block peroxidase activity and then stained in a second round of immunoperoxidase staining with PAL-E antibody by using 4-chloro-1-naphtol as substrate (blue-gray staining product). Sixty μm frozen sections of EF43-fgf4 tumors were double stained with ASD-37 and anti-CD31 antibodies. ASD-37 staining was detected by Cy3-conjugated secondary antibody and CD31 staining was detected by FITC-conjugated secondary antibody.

Immuno-electron microscopy was performed for biopsy materials as described by Schlingemann et al. (1996).

Tumor Homing In Vivo and Therapy Experiments

Nude mice bearing tumor xenografts derived from MDA-MB-435 human breast cancer cells were generated as described (Arap et al., 1998). 109 TU of CPKVCPRECSNC (SEQ ID NO:8)-displaying phage or fd-tet phage were injected intravenously to anesthetized mice. Phage were allowed to circulate for 5 minutes and the animals were perfused through the left ventricle of the heart with DMEM. The tumor and control organs were dissected and equal amounts of tissue were homogenized. Homogenates were washed with ice-cold DMEM containing a protease inhibitor cocktail (Sigma; St. Louis, Mo.) and 0.1% BSA. Tissue-bound phage were recovered as described above the cell panning. Tissue samples from the injected animals were fixed, sectioned at 5 μm and stained with an anti-M13 antibody.

For experimental therapy, Balb/c mice bearing EF43-fgf4-derived tumors were established and tumor volumes determined as described (Deroanne et al., 1997; Hajitou et al., 2001). Treatments in tumor-bearing mice were started 5 (peptides) to 7 days (antibodies) after cell inoculation (105 cells/mouse). Reagents were administered by ip and sc routes.

Statistical Analysis

Student's t-tests were used for statistical analysis.

Example 2

Targeting Peptides Specific for Aminopeptidase A (APA) and Treatments for Cancer The realization that angiogenic vasculature is a target for intervention in cancer has long led to an interest in endothelial cell receptors associated with tumor blood vessels and their corresponding ligands. However, so far only a few such targets have been identified.

A selection system is presented in the present invention in which circulating ligands that home to specific vascular beds in vivo are isolated from a phage display random peptide library; this approach led to the identification of vascular receptors allowing for systemic targeting of blood vessels in mice and more recently in human (Arap et al., 2002; Pasqualini and Ruoslahti, 1996). Some of the targets in tumor blood vessels turned out to be membrane-bound proteinases such as matrix metalloproteinases (Koivunen et al., 1999) or aminopeptidases (Pasqualini et al., 2000) that are upregulated in tumor blood vessels. While the biological relevance of the selective expression of proteinases within the angiogenic tumor blood vessel is not entirely understood, one can exploit such a feature to gain control of angiogenesis.

Aminopeptidase A (glutamyl-aminopeptidase, EC 3.4.11.7, APA) is a homodimeric type II membrane-spanning cell surface protein with zinc metallopeptidase activity that hydrolyzes N-terminal glutamyl or aspartyl residues from oligopeptide substrates (Nanus et al., 1993; Wu et al., 1990). Surprisingly, despite widespread tissue distribution (Li et al., 1993), APA-null mice develop normally (Lin et al., 1998). Since upregulation of APA has been reported in perivascular cells (termed "pericytes") of tumor blood vessels (Alliot et al., 1999; Schlingemann et al., 1996), the inventors set out to identify and analyze the effects of targeted ligands on the possible role of this enzyme in angiogenesis.

To evaluate whether an APA ligand-receptor system would allow functional targeting of tumor blood vessels, experiments were designed to assess both partners of the protein-protein interaction. The results in this example show that (i) APA is strongly upregulated in angiogenic tumor blood vessels but barely detectable in normal blood vessels, (ii) the enzymatic activity of APA co-localizes to its expression pattern in human tumors, and finally (iii) APA-null mice have an impaired angiogenesis phenotype that has been as yet unrecognized. To gain insight into the functional role of APA in angiogenesis, a phage display library was used to select APA-binding peptides and to isolate a novel inhibitory ligand. The consensus motif CPRECESIC (SEQ ID NO:2) (i) specifically binds to APA and inhibits its enzymatic activity, (ii) suppresses migration and proliferation of endothelial cells, (iii) inhibits in vitro and in vivo angiogenesis, (iv) homes to neovasculature, e.g., tumor vasculature, in vivo and (v) inhibits tumor growth in vivo. These genetic and biochemical data show that APA is a functional target in tumor blood vessels.

APA $^{-/-}$ Mice Show Impaired Angiogenesis

The angiogenic response of APA $^{-/-}$ mice was evaluated in two models of angiogenesis. First, the inventors used a mouse model of $O_2$-induced retinopathy (Smith et al., 1994). APA wild type (APA $^{+/+}$), APA heterozygotes (APA$^{+/-}$) and APA-null (APA mice were exposed to 75% $O_2$ from postnatal day 7 (P7) to P12, and then returned to room air. Retinas were analyzed at P17, when neovascularization had supervened on the vitreal surface. Angiogenesis was quantified by counting endothelial cell nuclei protruding into the vitreous space (Landenranta et al., 2001; Smith et al., 1994). Induction of retinal angiogenesis (16.1±3.3 endothelial cell nuclei/section) was seen in wild type mice on P17 (FIG. 1A), but significantly fewer endothelial cell nuclei (3.0±0.4 endothelial cell nuclei/section, t-test, P<0.001) were found in retinas from APA $^{-/-}$ mice (FIG. 1B). An intermediate decrease in retinal angiogenesis was observed in the APA $^{+/-}$ mice (10.1±2.2 endothelial cell nuclei/section) suggesting dose-dependence (FIG. 1C). No endothelial cell nuclei protruding into the vitreous space were found in mice exposed only to room air regardless of their genotype or time of analysis.

As a second model, a quantitative in vivo angiogenesis assay utilizing implanted gelfoam sponges saturated with angiogenic growth factors VEGF, bFGF and TGF-α was also utilized for testing (McCarty et al., 2002). To compare angiogenesis induction from subcutaneous tissue, sponges were implanted into the flanks of wild type (APA $^{+/+}$) or APA-null mice (APA $^{-/-}$). After two weeks, the sponges were harvested and stained with anti-CD31 antibodies to detect the endothelial cells of newly formed blood vessels permeating the sponge. Strong induction of CD31-positive capillary structure formation was observed in the growth factor-absorbed sponges implanted into wild type mice (FIG. 1D) whereas the number of CD31-positive capillary structures was much smaller in APA $^{-/-}$ mice and the only limited capillary formation observed was observed at the outer surface of the sponge (FIG. 1E).

These results suggest a deficient angiogenic response in APA $^{-/-}$ mice to relative hypoxia or to angiogenic growth factors as compared with their otherwise isogenic APA $^{+/+}$ counterparts.

Selection and Identification of APA-Binding Peptide Motifs

To identify peptides capable of binding to APA, the inventors screened APA-transfected cells with a phage display library (Smith and Scott, 1993). The inventors stably transfected SK-RC-49 renal carcinoma cells with a vector expressing full-length APA cDNA. APA functionality was verified in transfected cells by an enzyme activity assay specific for APA. Parental SK-RC-49 cells showed neither APA expression nor activity. An increase in phage binding to SK-RC-49/APA cells relative to SK-RC-49 cells was observed in the third round of selection (FIG. 2A). DNA sequencing revealed an enrichment of the sequence CYNLCIRECESIC-GADGA-CWTWCADGCSRSC (SEQ ID NO:9) containing tandem repeats of the general library sequence $CX_3CX_3CX_3C$ (SEQ ID NO:14) on each side of the pIII peptide linker GADGA (SEQ ID NO:19) sequence. 50% of randomly selected phage clones displayed such tandem repeat after the second round and 100% displayed it after the third round (Table 1).

TABLE 1

APA-binding peptide sequences.

| Peptide sequences | Round 2 (%) | Round 3 (%) | SEQ ID NO: |
|---|---|---|---|
| CYNLCIRECESICGADGACWTWCADGCSRSC | 50 | 100 | 1 |
| CPKVCPRECESNC | 5 | — | 3 |
| CLGQCASICVNDC | 5 | — | 4 |
| CGTGCAVECEVVC | 5 | — | 10 |
| CAVACWADCQLGC | 5 | — | 11 |
| CSGLCTVQCLEGC | 5 | — | 12 |
| CSMMCLEGCDDWC | 5 | — | 13 |
| Other | 20 | — | |

Validation of APA-Specific Phage Ligand Binding

Phage displaying enriched peptide motifs were tested individually for APA binding. Phage displaying the inserts CPKVCPRECESNC (SEQ ID NO:3), CYNLCIRECESIC-GADGACWTWCADGCSRSC (SEQ ID NO:1) or CLGQ-CASICVNDC (SEQ ID NO:4) preferentially bound to SK-RC-49/APA cells relative to SK-RC-49 cells; control insertless phage (fd-tet) showed no binding preference (FIG. 2B). The inventors synthesized peptides containing APA-binding motifs (consensus sequence CPRECESIC (SEQ ID NO:2); Table 1). Binding of phage displaying CPKVCPRE-CESNC (SEQ ID NO:3) or CYNLCIRECESICGAD-GACWTWCADGCSRSC (SEQ ID NO:1) peptides to SK-RC-49/APA cells was specific because it was inhibited by the synthetic peptide; several negative control peptides had no inhibitory effect. Binding of CLGQCASICVNDC (SEQ ID NO:4) phage to SK-RC-49/APA cells was not affected by the synthetic peptide suggesting that the SIC sequence in the consensus motif is not critical for binding. Whether the selected peptides would bind to the isolated APA protein was also evaluated. APA was immunocaptured from SK-RC-49/APA lysate with the RC38 antibody and showed, that the immunocaptured APA remained enzymatically active (FIG. 2C). The inventors used phage displaying CPKVCPRE-CESNC (SEQ ID NO:3), CLGQCASICVNDC (SEQ ID NO:4), or CYNLCIRECESICGADGACWTWCADGC-SRSC (SEQ ID NO:1) in binding assays to the immunocaptured APA. The inventors found up to 12-fold enrichment of phage binding to APA compared to immunocaptured cell lysates from the SK-RC-49 cells; control insertless phage (fd-tet) showed no binding preference (FIG. 2D).

These data support the specific binding of the selected peptides to isolated functional APA enzyme and to cell membrane-bound APA in vitro.

CPRECESIC (SEQ ID NO:2) is an Inhibitor of APA Enzymatic Activity

To evaluate the effect of synthetic CPRECESIC (SEQ ID NO:2) peptide on APA enzyme activity, APA-transfected cells were incubated with the APA-specific substrate α-glutamyl-p-nitroanilide with increasing concentrations of APA-binding or control peptides. The APA-binding peptide inhibited APA enzyme activity (colorimetric assay) while the control peptide had no effect (FIG. 3A). The inventors calculated the $IC_{50}$ of the peptide for APA enzyme inhibition to be ~800 μM. The inhibition was specific to APA because the peptide did not affect the enzymatic activity of aminopeptidase N, a related protein with homology to APA (Nanus et al., 1993; Wu et al., 1990).

CPRECESIC (SEQ ID NO:2) Suppresses Endothelial Cell Function

Because of the enzymatic inhibitory activity of APA-binding peptides, the inventors reasoned that they might affect endothelial cell function. The inventors correlated the effect of APA inhibition by the CPRECESIC (SEQ ID NO:2) peptide on the migration and proliferation of endothelial cells. The inventors used human dermal microvascular endothelial cells (HMEC) in which the APA expression was verified by immunostaining with RC38 and the APA activity by its specific enzyme assay. CPRECESIC (SEQ ID NO:2) peptide suppressed the migration of HMECs in the Boyden chamber assay (FIG. 3B). Suppression in cell migration was dose-dependent and commensurate with inhibition of APA enzymatic activity. Up to 60% suppression in cell migration was observed at 1 mM of peptide but significant inhibition was detected at concentrations as low as 100 μM (FIG. 3B). Similarly, proliferation of HMECs was suppressed by CPRECESIC (SEQ ID NO:2) (~40% at 1 mM) in a dose-dependent manner (FIG. 3C). Inhibition of cell proliferation was also observed at 0.3 mM but lower peptide concentrations had no significant effect. A negative control peptide affected neither cell migration nor proliferation.

These data indicate that an APA-binding peptide functions as a specific inhibitor of enzymatic activity and that inhibition of APA enzymatic activity is associated with suppression of migration and proliferation in human endothelial cells in vitro.

CPRECESIC (SEQ ID NO:2) Inhibits Capillary Tube Formation and Angiogenesis

To determine whether inhibition of APA enzyme activity with CPRECESIC (SEQ ID NO:2) peptide would affect angiogenesis, the effect of the peptide was tested in vitro and in vivo. First, the inventors evaluated the ability of HMECs to differentiate into capillary-like structures characteristic of angiogenesis in the presence of CPRECESIC (SEQ ID NO:2) on a gel of reconstituted basement membrane matrix (Matrigel). The formation of cord/tube-like structures was progressively impaired by increasing concentrations of CPRECESIC (SEQ ID NO:2) peptide, relative to the network formation in controls without peptide (FIG. 4A, upper left panel) or with an unrelated control peptide at 1 mM concentration (FIG. 4A, upper right panel). The number and length of capillary-like branching structures was reduced at 0.3 mM CPRECESIC (SEQ ID NO:2) peptide (FIG. 4A, lower left panel), whereas cell interconnections and the capillary network organization were severely lost at a peptide concentration of 1 mM (FIG. 4A, lower right panel).

Next, CPRECESIC (SEQ ID NO:2) activity was tested in a CAM assay. In this in vivo model, neovascularization is stimulated with VEGF adsorbed on to a gelatin sponge placed on the CAM. CAMs were stimulated on embryonic day 8 (E8) with sponges containing VEGF only, VEGF plus CPRECESIC (SEQ ID NO:2), or VEGF plus control peptides. CAMs were examined on E12 and neovascularization was quantified by counting the number of emerging capillaries (FIG. 4B). Significant induction of neovascularization (57.0±1.41 blood vessels) was found when a sponge with VEGF was placed on the CAM compared to a sponge with no growth factors (12.0±2.8 blood vessels; t-test, P<0.01). CPRECESIC (SEQ ID NO:2) peptide (1 mM) inhibited VEGF-induced CAM neovascularization by 40% (35.5±1.4 blood vessels; t-test, P<0.01). Equimolar concentrations of a negative control peptide (56.5±2.12 blood vessels; t-test, P<0.01, compared to the active CPECESIC (SEQ ID NO:2) peptide) or lower CPRECESIC (SEQ ID NO:2) peptide concentrations (0.1 mM and 0.3 mM) did not affect the number or branching of the growing blood vessels.

These data show that the CPRECESIC motif (SEQ ID NO: 2) inhibits blood vessel formation in standard models of angiogenesis.

APA Expressed in Blood Vessels of Human Tumors is Active

The extensive proliferation of blood vessels in malignant gliomas suggests an early role of angiogenesis in brain tumors (Wesseling et al., 1995). To investigate the expression of APA in brain tumor vasculature, the localization of APA expression was compared by immunostaining to the localization of APA activity by enzyme histochemistry in a panel (n=14) of primary and metastatic human brain tumors and in the incidental normal tissue adjacent to the tumors. APA enzyme activity in tissue sections co-localized with APA expression detected by an RC38 antibody. The staining pattern was consistent with APA localization to perivascular cells in the tumor microvasculature (FIG. 5A and FIG. 5B, glioblastoma multiforme; FIG. 5C and FIG. 5D, squamous cell carcinoma of the lung metastatic to the brain). Staining and enzymatic activity were apparent in sites of glomerular vascular proliferation in malignant gliomas and metastatic carcinomas. In contrast, APA expression and activity were barely detectable in capillaries in normal brain parenchyma (data not shown). By double-staining with RC38 and with PAL-E antibody, a general endothelial marker (Schlingemann et al., 1985), APA expression in colon adenocarcinoma metastatic to the brain appears to be restricted to perivascular cells (FIG. 5E). The inventors also showed by immunostaining that blood vessels in human non-malignant granulation tissue express APA (FIG. 5F). Finally, the inventors localized APA staining to perivascular cells by immuno-electron microscopy (FIG. 5G).

These results show that the APA present in blood vessels during the progression of malignant tumors is enzymatically active and therefore may contribute to the angiogenic process associated with human brain tumors.

APA-Binding Phage Targets Tumor Vasculature

The inventors next evaluated the ability of APA binding peptides to home to tumor blood vessels in vivo. Phage were administered intravenously to nude mice bearing human breast carcinoma MDA-MB-435-derived xenografts. Phage homing was quantified by recovery from tissue homogenates by bacterial infection. CPKVCPRECESNC (SEQ II) NO:3)

phage were enriched in tumors compared to control organs; in contrast, negative control phage (without a peptide insert) did not enrich in tumors (FIG. 6A). Homing of CPKVCPRECESNC (SEQ ID NO:3) phage to tumor vasculature was confirmed by immunohistochemical staining of phage on tissue sections. Strong phage staining was observed in tumor blood vessels—but not in normal brain blood vessels—of mice that received CPKVCPRECESNC (SEQ ID NO:3) phage; in contrast, negative control phage without insert did not home to tumor blood vessels (FIG. 6B). These results show that APA-binding phage target tumor blood vessels in vivo.

APA-Binding Peptides or Anti-APA Antibodies can Suppress Tumor Growth

To evaluate whether APA inhibitory ligands (APA-binding peptides or anti-APA blocking antibodies) suppress tumor growth in vivo, the inventors used EF43-fgf4-derived tumors, an established mouse mammary carcinoma model (Deroanne et al., 1997, Hajitou et al., 2001). The inventors have chosen this model because APA expression is undetectable in EF43-fgf4 cells but strongly induced in the tumor blood vessels associated with EF43-fgf4-derived tumors (FIG. 7A) and homing of APA-binding phage to tumor vasculature was experimentally validated (data not shown). Tumor-bearing mice received vehicle, CPRECESIC (SEQ ID NO:2) or control peptides and tumors were monitored (FIG. 7B). The inventors observed differences in tumor growth as early as 5 days after treatment initiation and when the experiment was terminated at the end of two weeks, CPRECESIC-treated mice (SEQ ID NO:2) had significantly smaller tumors (1,366±190 mm$^3$). relative to tumor-bearing control mice that received control peptide (2,626±335 mm$^3$; P=0.006); tumors in mice treated by control peptide behaved similarly to those tumors in mice receiving vehicle alone (2,295±381 mm$^3$; P=0.53) indicating that the control peptide had no measurable effect. Of note, another synthetic APA-binding peptide (sequence CPRECESN (SEQ ID NO:6)) also showed efficacy in vivo.

However, because the APA-inhibitory peptides may require a relatively high molar range (~250 nanomoles/mouse/dose) to be effective, the inventors also evaluated the effects of anti-APA antibodies on tumor growth. The inventors used an established regimen of two anti-APA monoclonal antibodies (ASD-37/41) with synergistic APA inhibitory properties (Assmann et al., 1992, Mentzel et al., 1999) on the same animal model. Tumor-bearing mice received vehicle, ASD-37/41, or isotype control IgG and tumors were monitored (FIG. 7C). Again, the inventors noticed clear differences in tumor growth. By the end of two weeks when the experiment was terminated, ASD-37/41-treated mice had significantly smaller tumor volumes (663±77 mm$^3$) relative to tumor-bearing control mice that received isotype negative control IgG (1,441±231 mm$^3$, P=0.013); tumors in mice treated by control IgG behaved similarly to those tumors in mice receiving vehicle only (1,845±313 mm$^3$, P=0.38) indicating that control IgG had no detectable effect on tumor growth. Finally, to analyze post-treatment effects of APA-inhibitory antibodies in tumors and their angiogenic blood vessels, the inventors examined tissue sections of all groups by CD31-immunostaining (FIG. 7D). In contrast to the recognized (Deroanne et al., 1997, Hajitou et al., 2001) extensive blood vessel network typically observed in EF43-fgf4-derived tumors, ASD-37/41-treated tumors exhibited a mixture of viable tissue (towards the outer rim of the tumors) and neighboring regions of disrupted vascular structure along with large areas of widespread cell death and destruction of the tumor architecture; inhibitory peptides had similar but less pronounced effect on treated tumors (FIG. 7D).

Taken together, these results indicate that APA-inhibitory ligands can specifically target angiogenic vasculature and suppress tumor growth in vivo.

All of the COMPOSITIONS and METHODS disclosed and claimed herein can be made and executed without undue experimentation in light of the present disclosure. While the compositions and methods of this invention have been described in terms of preferred embodiments, it are apparent to those of skill in the art that variations maybe applied to the COMPOSITIONS and METHODS and in the steps or in the sequence of steps of the methods described herein without departing from the concept, spirit and scope of the invention. More specifically, it are apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 5,021,236
U.S. Pat. No. 5,206,347
U.S. Pat. No. 5,223,409
U.S. Pat. No. 5,401,511
U.S. Pat. No. 5,492,807
U.S. Pat. No. 5,603,872
U.S. Pat. No. 5,622,699
U.S. Pat. No. 5,670,312
U.S. Pat. No. 5,705,610
U.S. Pat. No. 5,840,841
U.S. Pat. No. 5,889,155
U.S. Pat. No. 6,068,829
U.S. Pat. No. 6,649,407
U.S. Patent Appln 20040023415
Ades et al., *J. Invest. Dermatol.,* 99:683-690, 1992.
Alliot et al., *Brain Res.,* 830:101-112, 1999a.
Alliot et al., *J. Neurosci. Res.,* 58:367-378, 1999b.
Arap et al., *Science,* 279:377-80, 1998.
Assmann et al., *J. Exp. Med.,* 175:623-635, 1992.
Baichwal and Sugden, In: *Gene Transfer*, Kucherlapati R, ed., New York, Plenum Press, pp. 117-148, 1986.
Bakhshi et al., *Cell,* 41(3):899-906, 1985.
Barany and Merrifield, *The Peptides*, Gross and Meienhofer, eds., Academic Press, NY, 1-284, 1979.
Bergers et al, *J. Clin. Invest.,* 111:1287-1295, 2003.
Bogenreider et al., *Prostate,* 33:225-232, 1997.
Brooks et al. *Cell,* 79:1157-1164, 1994.
Burg et al., *Cancer Res.,* 58:2869-2874, 1999.
Bussolino et al., *J. Clin. Invest.,* 96:940-952, 1995.

Cleary and Sklar, *Proc. Natl. Acad. Sci. USA*, (21):7439-7443, 1985.
Cleary et al., *J. Exp. Med.*, 164(1):315-320, 1986.
Coffin, In: *Virology*, Fields et al., eds., Raven Press, NY, 1437-1500, 1990.
Deroanne et al., *Cancer Res.*, 57:5590-5597, 1997.
Egeblad and Werb, *Nat. Rev. Cancer*, 2:161-174, 2002.
Eliceiri and Cheresh, *Curr. Opin. Cell Biol.*, 13(5):563-568, 2001.
Ellerby et al., *Nature Med.*, 9:1032-1038, 1999.
Folkman, *Nature Biotechnol.*, 15:510, 1997.
Fujimura et al., *Oncology*, 58:342-352, 2000.
Geng et al., *Anticancer Res.*, 18:1-7, 1998.
Giordano et al., *Nat. Med.*, 7:1249-1253, 2001.
Gomez-Foix et al., *J. Biol. Chem.*, 267:25129-25134, 1992.
Graham and Prevec, In: *Methods in Molecular Biology: Gene Transfer and Expression Protocol*, Murray (Ed.), Humana Press, Clifton, N.J., 7:109-128, 1991.
Grunhaus and Horwitz, *Seminar in Virology*, 3:237-252, 1992.
Hajitou, et al. *Cancer Res.*, 61:3450-3457, 2001.
Hammes et al., *Nature Med.*, 2:529-533, 1996.
Harlow and Lane *Antibodies: A Laboratory Manual* (Cold Spring Harbor Laboratory Press, New York, N.Y.), 1988.
Hashizume et al., *Am. J. Pathol.*, 156:1363-1380, 2000.
Hermonat and Muzycska, *Proc. Natl. Acad. Sci. USA*, 81:6466-6470, 1984.
Herz and Gerard, *Proc. Natl. Acad. Sci. USA*, 90:2812-2816, 1993.
Ino et al., *Placenta*, 21:63-72, 2000.
Jackson et al., In: *Goodman and Gilman's The Pharmacological basis of therapeutics*, Hardman (Eds.), McGraw-Hill Medical Publishing Division, 809-841, 2001.
Johnson et al., Biotechnology and Pharmaccy, Pezzuto et al. (Eds.), Chapman and Hall, New York, 1993.
Juillerat-Jeanneret et al., *Lab. Invest.*, 80:973-80, 2000.
Juillerat-Jeanneret et al., *Cell Tissue Res.*, 311:53-59, 2003.
Kifor and Dzau, *Circ. Res.*, 60:422-428, 1987.
Koivunen et al. *Methods Mol. Biol.*, 129:3-17, 1999b.
Koivunen et al., *Nat. Biotechnol.*, 17:768-774, 1999.
Koivunen et al., *Nature Biotechnol.*, 17:768-774, 1999a
Landenranta et al., *Proc. Natl. Acad. Sci. USA*, 98:10368-10373, 2001.
Le Gal La Salle et al., *Science*, 259:988-990, 1993.
Le-Noble et al., *J. Vasa Res.* 33:480-488, 1996.
Levrero et al., *Gene*, 101:195-202, 1991.
Li et al., *Tissue Antigens*, 42:488-496, 1993.
Lin et al., *J. Immunol.*, 160:4681-4687, 1998.
Look, *J. Clin. Invest.*, 83:1299-1307, 1989.
Mann et al., *Cell*, 33:153-159, 1983.
McCarty et al., *Int. J. Oncol.*, 21:5-10, 2002.
Mentzel et al., *Kidney Int.*, 55:1335-1347, 1999.
Merrifield, *Science*, 232: 341-347, 1986.
Monton et al., *J. Am. Soc. Nephrol.*, 9:969-974, 1998.
Morikawa et al., *Am. J. Pathol.*, 160:985-1000, 2002.
Murphy et al., *J. Cell Physiol.*, 157:351-358, 1993.
Mustonen and Alitalo, *J. Cell Biol.*, 129:895-898, 1995.
Nadal et al., *Am. J. Physiol. Heart Circ. Physiol.*, 282:739-748, 2002.
Nanus et al., *Proc. Natl. Acad. Sci. USA*, 90:7069-7073, 1993.
Nicolas and Rubinstein, In: *Vectors: A survey of molecular cloning vectors and their uses*, Rodriguez and Denhardt, eds., Stoneham: Butterworth, pp. 494-513, 1988.
Nicolau et al., *Methods Enzymol.*, 149:157-176, 1987.
Paskind et al., *Virology*, 67:242-248, 1975.
Pasqualini and Ruoslahti, *Nature*, 380:364-366, 1996.
Pasqualini et al., *Cancer Res.*, 60:722-727, 2000.
Pasqualini et al., *Nature Biotechnol.*, 15:542-546, 1997.
Pasqualini, *J. Nucl. Med.*, 43:159-162, 1999.
PCT Appln. US01/28124
PCT Appln. US01/28044
Physicians Desk Reference
Ragot et al., *Nature*, 361:647-650, 1993.
Rajotte and Ruoslahti, *J. Biol. Chem.*, 274:11593-11598, 1999.
Rajotte et al., *J. Clin. Invest.*, 102:430-437, 1998.
Remington's Pharmaceutical Sciences, 15$^{th}$ ed., pages 1035-1038 and 1570-1580, Mack Publishing Company, Easton, Pa., 1980.
Remington's Pharmaceutical Sciences, 18$^{th}$ Ed., Mack Printing Co., 1289-1329, 1990.
Ribatti et al., *J. Vasc. Res.*, 34:455-463, 1997.
Ridgeway, In: *Vectors: A Survey of Molecular Cloning Vectors and Their Uses*, Rodriguez et al., eds., Stoneham: Butterworth, pp. 467-492, 1988.
Rosenfeld et al., *Cell*, 68:143-155, 1992.
Rosenfeld et al., *Science*, 252:431-434, 1991.
Sang, *Cell Res.*, 8:171-177, 1998.
Schlingemann et al., *Am. J. Pathol.*, 138:1335-1347, 1991.
Schlingemann et al., *J. Pathol.*, 179:436-442, 1996.
Schlingemann et al., *Lab. Invest.*, 52:71-76, 1985.
Smith and Scott, *Meth. Enzymol.*, 21:228-257, 1993.
Smith and Scott, *Science* 228,1315-1317, 1985.
Smith et al., *Invest. Opthalmol. Vis. Sci.*, 35:101-111, 1994.
Stewart and Young, *Solid Phase Peptide Synthesis*, 2d. ed., Pierce Chemical Co., 1984.
Tam et al., *J. Am. Chem. Soc.*, 105:6442, 1983.
Temin, In: *Gene Transfer*, Kucherlapati R, ed., New York, Plenum Press, pp. 149-188, 1986.
Tsujimoto and Croce, *Proc. Natl. Acad. Sci. USA*, 83(14):5214-5218, 1986.
Tsujimoto et al., *Science*, 228(4706):1440-1443, 1985.
Volpert et al., *J. Clin. Invest.*, 98:671-679, 1996.
Walsh et al., *Br. J. Pharmacol.*, 120:1302-1311, 1997.
Watson et al., *Science*, 268:447-448, 1995.
Wesseling et al., *J. Neuropathol. Exp. Neurol.*, 54:304-310, 1995.
Wickham et al., *Cancer Immunol. Immunother.*, 45:149-151, 1997c.
Wong et al., *Gene*, 10:87-94, 1980.
Wu et al., *Proc. Natl. Acad. Sci. USA*, 87:993-997, 1990.
Yoshiji et al., *Clin. Cancer Res.*, 7:1073-1078, 2001.
Zempo et al., *Arterioscler. Thromb. Vasc. Biol.*, 16:28-33, 1996.

What is claimed is:

1. A method of delivering a peptide to a cell population expressing aminopeptidase A, the method comprising
   a). obtaining a peptide of 50 amino acids or less in length that comprises the peptide sequence selected from the group consisting of SEQ ID NO: 1, SEQ ID NO: 2, SEQ ID NO: 3, SEQ ID NO: 4, SEQ ID NO: 5 and SEQ ID NO: 6, wherein said peptide selectively binds aminopeptidase A and
   b). contacting a cell population with said peptide, wherein at least some of the cells of the cell population express aminopeptidase A.

2. The method of claim 1, wherein said peptide inhibits the activity of aminopeptidase A.

3. The method of claim 1, wherein the peptide comprises SEQ ID NO:1.

4. The method of claim 1, wherein the peptide comprises SEQ ID NO:2.

5. The method of claim 1, wherein the peptide comprises SEQ ID NO:3.

6. The method of claim 1, wherein the peptide comprises SEQ ID NO:4.

7. The method of claim 1, wherein the peptide comprises SEQ ID NO:5.

8. The method of claim 1, wherein the peptide comprises SEQ ID NO:6.

9. The method of claim 1, wherein the peptide is 40 amino acids or less in length.

10. The method of claim 9, wherein the peptide comprising the sequence of SEQ ID NO: 2, SEQ ID NO: 3, SEQ ID NO: 4, SEQ ID NO: 5 or SEQ ID NO: 6, and is 30 amino acids or less in length.

11. The method of claim 10, wherein the peptide is 20 amino acids or less in length.

12. The method of claim 11, wherein the peptide is 10 amino acids or less in length.

13. The method of claim 1, wherein said peptide is attached to a macromolecular complex.

14. The method of claim 13, wherein said complex is a virus, a bacteriophage, a bacterium, a liposome, a microparticle, a nanoparticle, a magnetic bead, a radioisotope, a paramagnetic ion or a cell.

15. The method of claim 14, wherein said complex is a virus or a bacteriophage.

16. The method of claim 15, wherein said virus is selected from the group consisting of adenovirus, retrovirus and adeno-associated virus.

17. The method of claim 15, wherein said virus is further defined as containing a gene therapy vector.

18. The method of claim 14, wherein said peptide is attached to a eukaryotic expression vector.

19. The method of claim 18, wherein said vector is a gene therapy vector.

20. The method of claim 2, wherein said peptide is selected from the group consisting of SEQ ID NO:1, SEQ ID NO:2, or SEQ ID NO:3.

21. The method of claim 1, wherein said cell population is in a mammal and the peptide is administered into the mammal.

22. The method of claim 21, wherein said mammal is a human.

23. The method of claim 22, wherein said peptide is administered in a pharmaceutically acceptable carrier.

24. The method of claim 22, further comprising administering a second therapeutic agent to said human.

25. The method of claim 1, wherein said peptide is coupled or fused to an agent to be delivered to a cell expressing aminopeptidase A.

26. The method of claim 25, wherein the agent is a therapeutic agent.

27. The method of claim 26, wherein said therapeutic agent is a drug, a chemotherapeutic agent, a radioisotope, a pro-apoptosis agent, an anti-angiogenic agent, a hormone, a cytokine, a cytotoxic agent, a cytocidal agent, a cytostatic agent, a peptide, a protein, an antibiotic, an antibody, a Fab fragment of an antibody, a hormone antagonist, a nucleic acid or an antigen.

28. The method of claim 27, wherein the anti-angiogenic agent is selected from the group consisting of thrombospondin, angiostatin 5, pigment epithelium-derived factor, angiotensin, laminin peptides, fibronectin peptides, plasminogen activator inhibitors, tissue metalloproteinase inhibitors, interferons, interleukin 12, platelet factor 4, IP-10, Gro-β, thrombospondin, 2-methoxyoestradiol, proliferin-related protein, carboxiamidotriazole, CM101, Marimastat, pentosan polysulphate, angiopoietin 2, interferon-alpha, herbimycin A, PNU145156E, 16K prolactin fragment, Linomide, thalidomide, pentoxifylline, genistein, TNP-470, endostatin, paclitaxel, Docetaxel, polyamines, a proteasome inhibitor, a kinase inhibitor, a signaling peptide, accutin, cidofovir, vincristine, bleomycin, AGM-1470, platelet factor 4 and minocycline.

29. The method of claim 27, wherein said pro-apoptosis agent is selected from the group consisting of etoposide, ceramide sphingomyelin, Bax, Bid, Bik, Bad, caspase-3, caspase-8, caspase-9, fas, fas ligand, fadd, fap-1, tradd, faf, rip, reaper, apoptin, interleukin-2 converting enzyme, annexin V, gramicidin, magainin, mellitin, defensin, cecropin, (KLAKLAK)2 (SEQ ID NO: 15), (KLAKKLA)2 (SEQ ID NO: 16), (KAAKKAA)2 (SEQ ID NO: 17) or (KLGKKLG)3 (SEQ ID NO: 18).

30. The method of claim 27, wherein said cytokine is selected from the group consisting of interleukin 1 (IL-1), IL-2, IL-5, IL-10, IL-11, IL-12, IL-18, interferon-γ (IF-γ), IF-α, IF-β, tumor necrosis factor-α (TNF-α), or GM-CSF (granulocyte macrophage colony stimulating factor).

31. The method of claim 25, wherein said method is further defined as a diagnostic method and said agent is a diagnostic agent.

32. The method of claim 31, wherein the diagnostic agent is an imaging agent.

33. The method of claim 32, wherein the imaging agent comprises chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) erbium (III), lanthanum (III), gold (III), lead (II), or bismuth (III).

34. The method of claim 32, wherein the agent is a radioisotope, and the radioisotope is astatine$^{211}$, $^{14}$-carbon, $^{51}$chromium, $^{36}$-chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ or yttrium$^{90}$.

35. The method of claim 32 or claim 14, wherein the complex comprises a radioisotope, and the radioisotope is astatine$^{211}$, $^{14}$-carbon, $^{51}$chromium, $^{36}$-chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ or yttrium$^{90}$.

36. The method of claim 1, further defined as a therapeutic method.

37. The method of claim 36, wherein the method is a method of treating cancer cells that express aminopeptidase A.

38. The method of claim 36, wherein the method is a method of treating a retinal cell of diabetic retinopathy, wherein the cell expresses aminopeptidase A.

* * * * *

UNITED STATES PATENT AND TRADEMARK OFFICE
CERTIFICATE OF CORRECTION

| | | |
|---|---|---|
| PATENT NO. | : 7,914,780 B1 | Page 1 of 1 |
| APPLICATION NO. | : 12/186208 | |
| DATED | : March 29, 2011 | |
| INVENTOR(S) | : Wadih Arap et al. | |

It is certified that error appears in the above-identified patent and that said Letters Patent is hereby corrected as shown below:

In claim 31, column 58, lines 1-2, delete "further defined as".

In claim 35, column 58, line 18, delete "claim 32 or".

Signed and Sealed this
Fifth Day of July, 2011

David J. Kappos
*Director of the United States Patent and Trademark Office*